US008575368B2

(12) United States Patent
Nagamine

(10) Patent No.: US 8,575,368 B2
(45) Date of Patent: Nov. 5, 2013

(54) PROANTHOCYANIDIN OF CASHEW APPLE, COMPOSITION CONTAINING PROANTHOCYANIDIN, AND APPLICATION THEREOF

(75) Inventor: Kenichi Nagamine, Tokyo (JP)

(73) Assignee: Nichirei Biosciences, Inc., Tokyo (JP)

( * ) Notice: Subject to any disclaimer, the term of this patent is extended or adjusted under 35 U.S.C. 154(b) by 0 days.

(21) Appl. No.: 13/142,238

(22) PCT Filed: Jun. 25, 2009

(86) PCT No.: PCT/JP2009/061639
§ 371 (c)(1),
(2), (4) Date: Jun. 24, 2011

(87) PCT Pub. No.: WO2010/073757
PCT Pub. Date: Jul. 1, 2010

(65) Prior Publication Data
US 2011/0263698 A1    Oct. 27, 2011

(30) Foreign Application Priority Data

Dec. 26, 2008  (WO) .................. PCT/JP2008/073843

(51) Int. Cl.
*C07D 311/76* (2006.01)
*A61K 31/353* (2006.01)
(52) U.S. Cl.
USPC .......................................... 549/400; 514/456
(58) Field of Classification Search
USPC ................... 514/456; 549/399, 400; 435/132
See application file for complete search history.

(56) References Cited

U.S. PATENT DOCUMENTS

| 6,294,190 B1 | 9/2001 | Nakahara et al. |
| 2005/0010040 A1 | 1/2005 | Gourdin et al. |
| 2008/0306284 A1 | 12/2008 | Nakai et al. |

FOREIGN PATENT DOCUMENTS

| EP | 0815857 A1 | 1/1998 |
| EP | 1676572 A1 | 7/2006 |
| EP | 1783127 A1 | 5/2007 |
| JP | 9-291039 A | 11/1997 |
| JP | 2000-044472 A | 2/2000 |
| JP | 2002-179586 A | 6/2002 |
| JP | 2004-115466 A | 4/2004 |
| JP | 2004-189656 A | 7/2004 |
| JP | 2005-053891 A | 3/2005 |
| JP | 2005-314316 A | 11/2005 |
| JP | 2006-001909 A | 1/2006 |
| JP | 2006-016367 A | 1/2006 |
| JP | 2006-151944 A | 6/2006 |
| JP | 2006-213633 A | 8/2006 |
| JP | 2007-518812 A | 7/2007 |
| JP | 2008-019180 A | 1/2008 |
| JP | 2008-138129 A | 6/2008 |
| WO | 2005/030200 A1 | 4/2005 |

OTHER PUBLICATIONS

Michodjehoun-Mestres et al, 2009, Food Chemistry, vol. 114, p. 989-995.*
Lowor et al, 2009, American Journal of Food Technology, vol. 4, p. 154-161.*
Cavalcante et al, 2003, Environmental and Molecular Mutagenesis, vol. 41, p. 360-369.*
Gu, 2004, J. Nutr., vol. 134, p. 613-617.*
Gu, Liwei, et al., "Fractionation of Polymeric Procyanidins from Lowbush Blueberry and Quantification of Procyanidins in Selected Foods with an Optimized Normal-Phase HPLC-MS Fluorescent Detection Method", J. Agric. Food Chem., 2002, pp. 4852-4860, vol. 50.
Gu, Liwei, et al., "Screening of Foods Containing Proanthocyanidins and Their Structural Characterization Using LC-MS/MS and Thiolytic Degradation", J. Agric. Food Chem., 2003, pp. 7513-7521, vol. 51.
Lee, Young A., et al., "Inhibitory Activities of Proanthocyanidins from Persimmon against Oxidative Stress and Digestive Enzymes Related to Diabetes", J. Nutr. Sci. Vitaminol., 2007, pp. 287-292, vol. 53, No. 3.
Loo, Alvin Eng Kiat, et al., "Assay-guided Fractionation Study of α-Amylase Inhibitors from *Garcinia mangostana* Pericarp", J. Agric. Food. Chem., 2007, pp. 9805-9810, vol. 55.
McDougall, Gordon J., et al., "Different Polyphenolic Components of Soft Fruits Inhibit α-Amylase and α-Glucosidase", J. Agric. Food Chem., 2005, pp. 2760-2766, vol. 53.
Melo, Enayde De Almeida, et al., "Polyphenol, Ascorbic Acid in Total Carotenoid Contents in Common Fruits and Vegetables", Braz. J. Food Technol., Jun. 2006, pp. 89-94, vol. 9, No. 2.
Michodjehoun-Mestres, Laetitia, et al., "Characterisation of highly polymerised prodelphinidins from skin and flesh of four cashew apple (*Anacardium occidentale* L.) genotypes", Food Chemistry, 2009, pp. 989-995, vol. 114.
Sugiyama, Hiroshi, et al., "Oligomeric Procyanidins in Apple Polyphenol Are Main Active Components for Inhibition of Pancreatic Lipase and Triglyceride Absorption", J. Agric. Food. Chem., 2007, pp. 4604-4608, vol. 55.
Uehara, Shizuka, et al., "Inhibitory Effects of Proanthocyanidin-rich Extract from Grape Seeds on Melanogenesis", Koushou Kaishi (Journal of Cosmetic Science Society), 2003, pp. 247-256, vol. 27, No. 4.

* cited by examiner

*Primary Examiner* — Young Chu
*Assistant Examiner* — Karen Cheng
(74) *Attorney, Agent, or Firm* — Sughrue Mion, PLLC

(57) ABSTRACT

This invention provides useful applications of cashew apple. This invention also provides a naturally occurring active ingredient having useful activities, such as alpha-amylase inhibitory activity, lipase inhibitory activity, and antibacterial activity against *Propionibacterium acnes*. The invention also provides a composition containing cashew apple-derived proanthocyanidin having excellent alpha-amylase inhibitory activity, lipase inhibitory activity, and antibacterial activity against *Propionibacterium acnes*, which is prepared by allowing a plant fiber-degrading enzyme (e.g., pectinase) to react with a cashew apple and concentrating the resultant with the use of an ultrafiltration membrane. Further, the invention provides a proanthocyanidin compound having a novel structure.

10 Claims, 37 Drawing Sheets

Elemental composition calculator

Target m/z:      +459.0922      amu
Tolerance:       +20.0000       ppm
Result type: Elemental
Max num of results: 20
Min DBE:         -0.5000        Max DBE:    +50.0000
Electron state:  Even
Num of charges:  1
Add water:       N/A
Add proton:      N/A
File Name:       20B02 (recalibrated).wiff

|   | Elements | Min Number | Max Number |
|---|---|---|---|
| 1 | C | 1 | 50 |
| 2 | H | 1 | 50 |
| 3 | O | 5 | 12 |
| 4 | S | 0 | 2 |

Fig. 16-4

| | Formula | Calculated m/z (amu) | mDa Error | PPM Error | DBE |
|---|---|---|---|---|---|
| 1 | C22 H19 O11 | 459.0921 | 0.0117 | 0.0256 | 13.5 |
| 2 | C23 H23 O6 S2 | 459.0930 | -0.8587 | -1.8706 | 12.5 |
| 3 | C26 H19 O6 S | 459.0896 | 2.5131 | 5.4742 | 17.5 |
| 4 | C19 H23 O11 S | 459.0955 | -3.3601 | -7.3191 | 8.5 |
| 5 | C29 H15 O6 | 459.0863 | 5.8851 | 12.8190 | 22.5 |
| 6 | C16 H27 O11 S2 | 459.0989 | -6.7321 | -14.6640 | 3.5 |

Fig. 17-3

Elemental composition calculator

Target m/z:      +413.1041      amu
Tolerance:       +20.0000       ppm
Result type:     Elemental
Max num of results: 20
Min DBE:         -0.5000        Max DBE:    +50.0000
Electron state:  Even
Num of charges:  1
Add water:       N/A
Add proton:      N/A
File Name:       20B02 (recalibrated)-2.wiff

| | Elements | Min Number | Max Number |
|---|---|---|---|
| 1 | C | 1 | 50 |
| 2 | H | 1 | 50 |
| 3 | O | 5 | 12 |
| 4 | S | 0 | 2 |

Fig. 17-4

| | Formula | Calculated m/z (amu) | mDa Error | PPM Error | DBE |
|---|---|---|---|---|---|
| 1 | C22 H21 O6 S | 413.1053 | -1.2368 | -2.9941 | 12.5 |
| 2 | C25 H17 O6 | 413.1019 | 2.1350 | 5.1683 | 17.5 |
| 3 | C18 H21 O11 | 413.1078 | -3.7382 | -9.0492 | 8.5 |
| 4 | C19 H25 O6 S2 | 413.1087 | -4.6088 | -11.1566 | 7.5 |
| 5 | C15 H25 O11 S | 413.1112 | -7.1102 | -17.2117 | 3.5 |

Fig. 18-3

Elemental composition calculator

Target m/z:      +565.1229    amu
Tolerance:       +20.0000     ppm
Result type:     Elemental
Max num of results: 20
Min DBE:         -0.5000      Max DBE:    +50.0000
Electron state:  Even
Num of charges:  1
Add water:       N/A
Add proton:      N/A
File Name:       20B02 (recalibrated)-2.wiff

|   | Elements | Min Number | Max Number |
|---|----------|------------|------------|
| 1 | C        | 1          | 50         |
| 2 | H        | 1          | 50         |
| 3 | O        | 5          | 12         |
| 4 | S        | 0          | 2          |

Fig. 18-4

| | Formula | Calculated m/z (amu) | mDa Error | PPM Error | DBE |
|---|---|---|---|---|---|
| 1 | C26 H29 O10 S2 | 565.1196 | 3.2324 | 5.7198 | 12.5 |
| 2 | C36 H21 O7 | 565.1281 | -5.2797 | -9.3426 | 26.5 |
| 3 | C29 H25 O10 S | 565.1162 | 6.6043 | 11.6866 | 17.5 |
| 4 | C33 H25 O7 S | 565.1315 | -8.6516 | -15.3093 | 21.5 |
| 5 | C33 H25 O5 S2 | 565.1137 | 9.1057 | 16.1129 | 21.5 |
| 6 | C32 H21 O10 | 565.1129 | 9.9763 | 17.6533 | 22.5 |
| 7 | C29 H25 O12 | 565.1340 | -11.1531 | -19.7356 | 17.5 |

PROANTHOCYANIDIN OF CASHEW APPLE, COMPOSITION CONTAINING PROANTHOCYANIDIN, AND APPLICATION THEREOF

CROSS REFERENCE TO RELATED APPLICATIONS

This application is a National Stage of International Application No. PCT/JP2009/061639, filed Jun. 25, 2009, which claims priority from International Patent Application No. PCT/JP2008/073843, filed Dec. 26, 2008, the contents of all of which are incorporated herein by reference in their entirety.

TECHNICAL FIELD

The present invention provides proanthocyanidin polymers derived from the cashew apple, a processed cashew apple product containing the same, and applications thereof.

BACKGROUND ART

*Anacardium occidentale* is a tall evergreen tree of Anacardiaceae that originated in Brazil, and yellow pear-shaped stalks thereof, when swollen to a size of 5 to 6 cm, are referred to as "cashew apples." The cashew apple smells like an apple and it is occasionally processed so as to be consumed fresh or in the form of juice beverage. Fruits covered with husks having the size of 2 to 3 cm and the curved and comma-shaped form are generated at the ends of swollen stalks. Kernels in the husks are cashew nuts. Cashew nuts are extensively used as food all over the world.

The term "anthocyanidin" refers to a type of colored aglycon belonging to the group of flavonoids and obtained via hydrolysis of anthocyanin. Anthocyanidin is roughly classified into three types (i.e., delphinidin, cyanidin, and pelargonidin types) depending on the number of hydroxyl bonds. The term "proanthocyanidin" refers to an ingredient that produces anthocyanidin when heated under acidic conditions, and it is a condensed tannin; i.e., compounds resulting from condensation or polymerization of flavan-3-ol or flavan-3,4-diol, as a constitutional unit. Proanthocyanidin, which generates delphinidin when heated under acidic conditions, is referred to as "prodelphinidin." Proanthocyanidin, which generates cyanidin, is referred to as "procyanidin," and proanthocyanidin, which generates pelargonidin, is referred to as "propelargonidin." Polymers of gallocatechin, epigallocatechin, gallocatechin gallate, and epigallocatechin gallate are known as prodelphinidins, and polymers of catechin, epicatechin, catechin gallate, and epicatechin gallate are known as procyanidins.

The cashew apple is known to contain anacardic acid and the like, although the existence of proanthocyanidin has not been reported.

Patent Document 1 (JP Patent Publication (Kokai) No. H09-291039 A (1997)) discloses an anti-obesity drug comprising, as an active ingredient, 2-mer to 80-mer procyanidin obtained from a tamarind seed coat extract. Patent Document 2 (JP Patent Publication (Kokai) No. 2006-151944 A) describes drugs for regulating neutral fat metabolism containing apple-derived polyphenol, including a procyanidin. Regarding the lipase inhibitory activity of procyanidin, Non-Patent Document 2 (J. Agric. Food Chem. 2007, 55, 4604-4609) describes that apple-derived procyanidins are precisely purified in accordance with degrees of polymerization, and lipase inhibitory activities are examined. In Non-Patent Document 2, the lipase inhibitory activity ($IC_{50}$) of 9-mer or higher procyanidin was given as 0.9 µg/ml, and that of chlorogenic acid, which was simultaneously measured, was given as 59.8 µg/ml. Alpha-amylase inhibitory activity and lipase inhibitory activity of prodelphinidin polymers are not known.

The following report has been made regarding prodelphinidin polymers. Patent Document 3 (JP Patent Publication (Kokai) No. 2008-138129 A) reports, as an "amylase inhibitor," an alpha-amylase inhibitor comprising a polymer of catechins selected from the group consisting of epicatechin, epicatechin gallate, epigallocatechin gallate, and epigallocatechin. This polymer was artificially synthesized via an enzyme reaction, and the claims of the above patent document describe that the number average molecular weight thereof is 10,000 or lower and the degree of polymerization is 2 to 20. All the examples describe the results of synthesis of a polymer of epigallocatechin gallate and a polycondensation product of epigallocatechin gallate and aldehyde. It can be inferred based on Patent Document 3 that prodelphinidin which is a polymer of epigallocatechin gallates has alpha-amylase inhibitory activity. However, the polymer described in Patent Document 3 is a compound obtained via an artificial reaction, many structural features remain unknown, and safety thereof when consumed also remains problematic.

Examples of patent documents regarding prodelphinidin include the following. Patent Document 4 (JP Patent Publication (Kokai) No. 2006-16367 A) describes lipase inhibitory activity of prodelphinidin having a plurality of dimers as molecular structures. Patent Document 5 (JP Patent Publication (Kokai) No. 2006-1909 A) describes a novel compound having lipase inhibitory activity. According to these patent documents, the lipase inhibitory activities ($IC_{50}$) of epigallocatechin gallate ((−)-epigallocatechin 3-O-gallate) are 0.284 µM and 0.349 µM (0.16 µg/ml), respectively. Non-Patent Document 1 (J. Agric. Food Chem, 2003, 51, 7513-7521) describes the results of analysis of constituents of a plurality of plant proanthocyanidins. This document, however, does not describe proanthocyanidins having average degrees of polymerization (mDP) of 50 or greater, and it does not report those comprising epigallocatechin gallate as constituents. While Non-Patent Document 1 teaches that "cashew", listed as one of nuts, contains proanthocyanidin in the form of an (epi)catechin dimer, the cashew apple is not mentioned.

Examples of patent documents regarding grape-derived proanthocyanidin include the following. Patent Document 6 (JP Patent Publication (Kokai) No. 2000-44472 A) describes that a proanthocyanidin oligomer (2- to 30-mer, preferably 2- to 10-mer) obtained from seeds, seed vessels, or the like of grapes has effects of inhibiting elevation in blood glucose levels and is effective as a therapeutic agent for diabetes as "a preventive or therapeutic agent for diabetic complications." While Patent Document 6 does not describe amylase inhibitory activity, it reports examples of blood glucose levels of diabetic rats that have been lowered with procyanidin B-3 (a dimer) and proanthocyanidin (a proanthocyanidin oligomer of a grape seed extract). Proanthocyanidin in such grape seed extract is considered to be procyanidin (an (epi) catechin polymer) (see Non-Patent Document 4 (*Koushou Kaishi* (Journal of Japanese Cosmetic Science Society), Vol. 27, No. 4, 2003) and Non-Patent Document 1 (J. Agric. Food Chem., 2003, 51, 7513-7521)).

A variety of active ingredients are known as lipase inhibitors.

Patent Document 7 (JP Patent Publication (Kokai) No. 2008-19180 A) describes the results of experimentation in which the lipase inhibitory activity of a *Bergenia ciliata* extract was compared with ibuprofenpiconol and tetracycline hydrochloride as positive controls.

Patent Document 8 (JP Patent Publication (Kokai) No. 2005-53891 A) discloses an invention intended to provide a lipase inhibitor having excellent pancreatic lipase or bacterial lipase inhibitory effects, contained in many plant species, excellent in safety, and effective when used for a tendency for obesity, pimples, or dermatitis. The examples of Patent Document 8 describe that caffeic acid (caffeine acid or 3,4-dihydroxycinnamic acid), gallic acid, and rosmarinic acid are effective as lipase inhibitors, and the examples also provide measured values thereof.

Patent Document 9 (JP Patent Publication (Kokai) No. 2004-115466 A) discloses an external skin preparation having effects of preventing and treating pimples containing proanthocyanidin. According to the claims of Patent Document 9, proanthocyanidin is derived from pine bark, grapes, blueberries, strawberries, avocados, false acacia, fruit or seeds of cowberries, barley, wheat, soybeans, black soybeans, cacao, peanut membranes, or *Ginkgo biloba* leaves. The examples do not describe lipase inhibitory activity, but the examples describe the results of an experiment regarding minimal growth inhibition of *Propionibacterium acnes* using a pine bark extract.

Patent Document 10 (JP Patent No. 3966689 B) describes a skin-disease-ameliorating agent for pimples containing an extract of rose root (*Rhodiola rosea*) and/or golden root (*Rhodiola sacra*) belonging to Crassulaceae. In the examples of Patent Document 10, a plurality of plant extracts are examined regarding lipase inhibitory activity derived from bovine pancreas. Among such plant extracts, patents have been granted for rose root and golden root extracts having lipase inhibitory activity ($IC_{50}$) of 40 µg/ml.

Pimples are developed mainly on the faces of adolescent boys and girls. The increased sebum secretion, inflammation caused by fatty acid generated by lipase of the epidermis or *Propionibacterium acnes*, abnormal multiplication of *Propionibacterium acnes*, and the like are considered to be the causes thereof. Prevention and treatment of pimples have heretofore involved the use of antibacterial agents (e.g., Patent Documents 11 and 12). However, such prevention and treatment techniques disadvantageously involve side effects caused by an antibacterial agent, development of bacteria resistant to an antibacterial agent, excessive disinfection of resident microbiota of the skin by an antibacterial agent, and other problems. Accordingly, development of highly safe pharmaceutical preparations capable of inhibiting excessive growth of *Propionibacterium acnes* has been awaited.

[Patent Document 1] JP Patent Publication (Kokai) No. H09-291039 A (1997)
[Patent Document 2] JP Patent Publication (Kokai) No. 2006-151944 A
[Patent Document 3] JP Patent Publication (Kokai) No. 2008-138129 A
[Patent Document 4] JP Patent Publication (Kokai) No. 2006-16367 A
[Patent Document 5] JP Patent Publication (Kokai) No. 2006-1909 A
[Patent Document 6] JP Patent Publication (Kokai) No. 2000-44472 A
[Patent Document 7] JP Patent Publication (Kokai) No. 2008-19180 A
[Patent Document 8] JP Patent Publication (Kokai) No. 2005-53891 A
[Patent Document 9] JP Patent Publication (Kokai) No. 2004-115466 A
[Patent Document 10] JP Patent No. 3966689 B
[Patent Document 11] JP Patent Publication (Kokai) No. 2004-189656 A
[Patent Document 12] JP Patent Publication (Kokai) No. 2006-213633 A
[Non-Patent Document 1] J. Agric. Food Chem, 2003, 51, 7513-7521
[Non-Patent Document 2] J. Agric. Food Chem. 2007, 55, 4604-4609
[Non-Patent Document 3] J. Agric. Food Chem., 2002, 50, 4852-4860
[Non-Patent Document 4] *Koushou Kaishi* (Journal of Japanese Cosmetic Science Society), Vol. 27, No. 4, 2003

DISCLOSURE OF THE INVENTION

Objects to be Attained by the Invention

The cashew apple is often wasted when cashew nuts are harvested. Accordingly, effective use of the cashew apple is desired.

It is an object of the present invention to provide useful applications of cashew apple.

It is another object of the present invention to provide naturally occurring active ingredients having useful activities, such as alpha-amylase inhibitory activity, lipase inhibitory activity, and antibacterial activity against *Propionibacterium acnes*.

Means for Attaining the Objects

The present invention provides the following as means for attaining the above objects.

(1) A composition containing cashew apple-derived proanthocyanidin, which is prepared by a method comprising a step of allowing a plant fiber-degrading enzyme to react with a cashew apple and a step of concentrating the enzyme-degraded product obtained by the former step with the use of an ultrafiltration membrane with a molecular-weight cut-off of 10,000 or greater.

(2) The composition according to (1), wherein the method further comprises a step of concentrating or separating polyphenol, following the step of allowing a plant fiber-degrading enzyme to react with a cashew apple.

(3) The composition according to (1) or (2), wherein the method further comprises a step of concentrating or separating proanthocyanidin, following the step of allowing a plant fiber-degrading enzyme to react with a cashew apple.

(4) The composition according to any of (1) to (3), wherein the proanthocyanidin contains prodelphinidin.

(5) A food or beverage composition, cosmetic composition, or pharmaceutical composition comprising the composition according to any of (1) to (4).

(6) Proanthocyanidin, which is a polymer comprising, as a constitutional unit, at least (epi)gallocatechin and (epi)gallocatechin gallate and having an average degree of polymerization of at least 20.

(7) The proanthocyanidin according to (6), which contains 50% to 80% by mole (epi)gallocatechin and 20% to 50% by mole (epi)gallocatechin gallate as constitutional units.

(8) The proanthocyanidin according to (6) or (7), which further contains epicatechin and epicatechin gallate as constitutional units.

(9) The proanthocyanidin according to any of (6) to (8), wherein at least one end of the polymer is epigallocatechin gallate.

(10) The proanthocyanidin according to any of (6) to (9), which is separated from a concentrate obtained by allowing a plant fiber-degrading enzyme to react with a cashew apple and concentrating the obtained enzyme-degraded product with the use of an ultrafiltration membrane with a molecular-weight cut-off of 10,000 or greater.

(11) A food or beverage composition, cosmetic composition, or pharmaceutical composition comprising the proanthocyanidin according to any of (6) to (10).

(12) An alpha-amylase inhibitor comprising, as an active ingredient, the composition according to any of (1) to (4).

(13) A preventive or therapeutic agent for a condition or disease that is prevented or improved via inhibition of alpha-amylase activity comprising, as an active ingredient, the composition according to any of (1) to (4).

(14) A lipase inhibitor comprising, as an active ingredient, the composition according to any of (1) to (4).

(15) A preventive or therapeutic agent for a condition or disease that is prevented or improved via inhibition of lipase activity comprising, as an active ingredient, the composition according to any of (1) to (4).

(16) An inhibitor of lipid deterioration comprising, as an active ingredient, the composition according to any of (1) to (4).

(17) An antibacterial agent against *Propionibacterium acnes* comprising, as an active ingredient, the composition according to any of (1) to (4).

(18) A preventive or therapeutic agent for a condition or disease that is prevented or improved via inhibition of the growth of *Propionibacterium acnes* comprising, as an active ingredient, the composition according to any of (1) to (4).

(19) An alpha-amylase inhibitor comprising, as an active ingredient, the proanthocyanidin according to any of (6) to (10).

(20) A preventive or therapeutic agent for a condition or disease that is prevented or improved via inhibition of alpha-amylase activity comprising, as an active ingredient, the proanthocyanidin according to any of (6) to (10).

(21) A lipase inhibitor comprising, as an active ingredient, the proanthocyanidin according to any of (6) to (10).

(22) A preventive or therapeutic agent for a condition or disease that is prevented or improved via inhibition of lipase activity comprising, as an active ingredient, the proanthocyanidin according to any of (6) to (10).

(23) An inhibitor of lipid deterioration comprising, as an active ingredient, the proanthocyanidin according to any of (6) to (10).

(24) An antibacterial agent against *Propionibacterium acnes* comprising, as an active ingredient, the proanthocyanidin according to any of (6) to (10).

(25) A preventive or therapeutic agent for a condition or disease that is prevented or improved via inhibition of the growth of *Propionibacterium acnes* comprising, as an active ingredient, the proanthocyanidin according to any of (6) to (10).

The present invention can also be described as follows.

A food or beverage composition, cosmetic composition, or pharmaceutical composition containing the proanthocyanidin in an amount of 0.025% by weight or more, and preferably 0.05% by weight or more, based on the total weight of the composition.

A food or beverage composition, cosmetic composition, or pharmaceutical composition containing no cashew apple-derived proanthocyanidin that passes through an ultrafiltration membrane with a molecular-weight cut-off of 10,000 or greater, and containing cashew apple-derived proanthocyanidin that does not pass through an ultrafiltration membrane with a molecular-weight cut-off of 10,000 or greater.

A method for inhibiting alpha-amylase by applying the proanthocyanidin-containing composition or the proanthocyanidin in vivo or in vitro.

A method for inhibiting alpha-amylase by applying the proanthocyanidin-containing composition or the proanthocyanidin to an in vivo or in vitro environment in which alpha-amylase exists.

The proanthocyanidin-containing composition or the proanthocyanidin used for an alpha-amylase inhibitor for in vivo or in vitro use.

Use of the proanthocyanidin-containing composition or the proanthocyanidin in the preparation of an alpha-amylase inhibitor in vivo or in vitro.

A method for preventing or treating a condition or disease that is prevented or improved via inhibition of alpha-amylase comprising administering the proanthocyanidin-containing composition or the proanthocyanidin to a patient (e.g., a human). An effective amount of the proanthocyanidin-containing composition or the proanthocyanidin for the prevention or treatment of such condition or disease is administered to a patient who needs to prevent or treat such condition or disease. Oral administration is preferable.

The proanthocyanidin-containing composition or the proanthocyanidin used for a preventive or therapeutic agent for a condition or disease that is prevented or improved via inhibition of alpha-amylase.

Use of the proanthocyanidin-containing composition or the proanthocyanidin in the preparation of a preventive or therapeutic agent for a condition or disease that is prevented or improved via inhibition of alpha-amylase.

Non-medical use of a sufficient amount of the proanthocyanidin-containing composition or the proanthocyanidin for inhibiting alpha-amylase for a food or beverage composition used for inhibiting alpha-amylase. The food or beverage composition is typically used for reducing the risk of developing a condition or disease that is prevented or improved via inhibition of alpha-amylase or inducing physiological effects that can serve as bases for prevention or treatment of such condition or disease in a person who has ingested such composition.

Use of a sufficient amount of the proanthocyanidin-containing composition or the proanthocyanidin for inhibiting alpha-amylase in the preparation of a medical food or beverage composition for inhibiting alpha-amylase. The medical food or beverage composition is typically used for preventing or treating a condition or disease that is prevented or improved via inhibition of alpha-amylase in a person who has ingested such composition.

A method for inhibiting lipase by applying the proanthocyanidin-containing composition or the proanthocyanidin in vivo or in vitro.

A method for inhibiting lipase by applying the proanthocyanidin-containing composition or the proanthocyanidin to an in vivo or in vitro environment in which lipase exists.

The proanthocyanidin-containing composition or the proanthocyanidin for using as a lipase inhibitor in vivo or in vitro.

Use of the proanthocyanidin-containing composition or the proanthocyanidin in the preparation of a lipase inhibitor in vivo or in vitro.

A method for preventing or treating a condition or disease that is prevented or improved via inhibition of lipase comprising administering the proanthocyanidin-containing composition or the proanthocyanidin to a patient (e.g., a human). An effective amount of the proanthocyanidin-containing composition or the proanthocyanidin for the prevention or treatment of such condition or disease is administered to a patient who needs to prevent or treat such condition or disease. Oral or percutaneous administration is preferable.

The proanthocyanidin-containing composition or the proanthocyanidin used for a preventive or therapeutic agent for a condition or disease that is prevented or improved via inhibition of lipase.

Use of the proanthocyanidin-containing composition or the proanthocyanidin in the preparation of a preventive or therapeutic agent for a condition or disease that is prevented or improved via inhibition of lipase.

An inhibitor of lipid deterioration comprising the proanthocyanidin-containing composition or the proanthocyanidin.

A method for inhibiting lipid deterioration by applying the proanthocyanidin-containing composition or the proanthocyanidin to an in vivo or in vitro environment in which lipids exist (e.g., the skin or a lipid-containing composition).

Use of the proanthocyanidin-containing composition or the proanthocyanidin for inhibiting lipid deterioration.

Non-medical use of a sufficient amount of the proanthocyanidin-containing composition or the proanthocyanidin for inhibiting lipase for a food or beverage composition used for inhibiting lipase. The food or beverage composition is typically used for reducing the risk of developing a condition or disease that is prevented or improved via inhibition of lipase or inducing physiological effects that can serve as bases for prevention or treatment of said condition or disease in a person who has ingested such composition.

Use of a sufficient amount of the proanthocyanidin-containing composition or the proanthocyanidin for inhibiting lipase in the preparation of a medical food or beverage composition for inhibiting lipase. The medical food or beverage composition is typically used for preventing or treating a condition or disease that is prevented or improved via inhibition of lipase in a person who has ingested such composition.

Non-medical use of a sufficient amount of the proanthocyanidin-containing composition or the proanthocyanidin for inhibiting lipase for a cosmetic composition used for inhibiting lipase. The cosmetic composition is typically used for reducing the risk of developing a condition or disease that is prevented or improved via inhibition of lipase or inducing physiological effects that can serve as bases for prevention or treatment of said condition or disease in a person who is administered such composition.

Use of a sufficient amount of the proanthocyanidin-containing composition or the proanthocyanidin for inhibiting lipase in the preparation of a medical cosmetic composition for inhibiting lipase. The medical cosmetic composition is typically used for preventing or treating a condition or disease that is prevented or improved via inhibition of lipase in a person who is administered such composition.

The proanthocyanidin-containing composition or the proanthocyanidin used for an antibacterial agent against *Propionibacterium acnes* in vivo or in vitro.

Use of the proanthocyanidin-containing composition or the proanthocyanidin in the preparation of the antibacterial agent against *Propionibacterium acnes* in vivo or in vitro.

A method for preventing or treating a condition or disease that is prevented or improved via inhibition of the growth of *Propionibacterium acnes* comprising administering the proanthocyanidin-containing composition or the proanthocyanidin to a patient (e.g., a human). An effective amount of the proanthocyanidin-containing composition or proanthocyanidin for the prevention or treatment of such condition or disease is administered to a patient who needs to prevent or treat such condition or disease. Percutaneous administration is preferable.

The proanthocyanidin-containing composition or the proanthocyanidin used for a preventive or therapeutic agent for a condition or disease that is prevented or improved via inhibition of the growth of *Propionibacterium acnes*.

Use of the proanthocyanidin-containing composition or the proanthocyanidin in the preparation of a preventive or therapeutic agent for a condition or disease that is prevented or improved via inhibition of the growth of *Propionibacterium acnes*.

Non-medical use of a sufficient amount of the proanthocyanidin-containing composition or the proanthocyanidin for inhibiting the growth of *Propionibacterium acnes* for a cosmetic composition used for inhibiting the growth of *Propionibacterium acnes*. The cosmetic composition is typically used for reducing the risk of developing a condition or disease that is prevented or improved via inhibition of the growth of *Propionibacterium acnes* or inducing physiological effects that can serve as bases for prevention or treatment of said condition or disease in a person who is administered such composition.

Use of a sufficient amount of the proanthocyanidin-containing composition or the proanthocyanidin for inhibiting the growth of *Propionibacterium acnes* in the preparation of a medical cosmetic composition for inhibiting the growth of *Propionibacterium acnes*. The medical cosmetic composition is typically used for preventing or treating a condition or disease that is prevented or improved via inhibition of the growth of *Propionibacterium acnes* in a person who is administered such composition.

The proanthocyanidin-containing composition or the proanthocyanidin used for a medicine.

Effects of the Invention

The present invention enables effective use of cashew apples, which have been often wasted in the past.

In addition, the present invention provides naturally occurring, highly safe active ingredients having useful activities such as alpha-amylase inhibitory activity, lipase inhibitory activity, and antibacterial activity against *Propionibacterium acnes*.

BRIEF DESCRIPTION OF THE DRAWINGS

FIG. 4-1 shows the $^1$H NMR spectra of the thiol-degraded and purified NBP (peak 1).

FIG. 4-2 shows the $^1$H NMR spectra of the thiol-degraded and purified NBP (peak 1) (continuation of FIG. 4-1).

FIG. 5-1 shows the $^1$H NMR spectra of the thiol-degraded and purified NBP (peak 1) (enlarged diagram).

FIG. 5-2 shows the $^1$H NMR spectra of the thiol-degraded and purified NBP (peak 1) (enlarged diagram) (continuation of FIG. 5-1).

FIG. 6-1 shows the $^{13}$C NMR spectra of the thiol-degraded and purified NBP (peak 1).

FIG. 6-2 shows the $^{13}$C NMR spectra of the thiol-degraded and purified NBP (peak 1) (continuation of FIG. 6-1).

FIG. 7-1 shows the $^{13}$C NMR spectra of the thiol-degraded and purified NBP (peak 1) (enlarged diagram).

FIG. 7-2 shows the $^{13}$C NMR spectra of the thiol-degraded and purified NBP (peak 1) (enlarged diagram) (continuation of FIG. 7-1).

FIG. 9-1 shows the $^1$H NMR spectra of the thiol-degraded and purified NBP (peak 2).

FIG. 9-2 shows the $^1$H NMR spectra of the thiol-degraded and purified NBP (peak 2) (continuation of FIG. 9-1).

FIG. 10-1 shows the $^1$H NMR spectra of the thiol-degraded and purified NBP (peak 2) (enlarged diagram).

FIG. 10-2 shows the $^1$H NMR spectra of the thiol-degraded and purified NBP (peak 2) (enlarged diagram) (continuation of FIG. 10-1).

FIG. 11-1 shows the $^{13}$C NMR spectra of the thiol-degraded and purified NBP (peak 2).

FIG. 11-2 shows the $^{13}$C NMR spectra of the thiol-degraded and purified NBP (peak 2) (continuation of FIG. 11-1).

FIG. 12-1 shows the $^{13}$C NMR spectra of the thiol-degraded and purified NBP (peak 2) (enlarged diagram 1).

FIG. 12-2 shows the $^{13}$C NMR spectra of the thiol-degraded and purified NBP (peak 2) (enlarged diagram 1) (continuation of FIG. 12-1).

FIG. 13-1 shows the $^{13}$C NMR spectra of the thiol-degraded and purified NBP (peak 2) (enlarged diagram 2).

FIG. 13-2 shows the $^{13}$C NMR spectra of the thiol-degraded and purified NBP (peak 2) (enlarged diagram 2) (continuation of FIG. 13-1).

FIG. 16-1 shows the results of LC-MS assay of peak (1) of a solution of the thiol-degraded 10K NBP-A fraction.

FIG. 16-2 shows the accurate mass spectra of peak (1) of a solution of the thiol-degraded 10K NBP-A fraction.

FIG. 16-3 shows the results of calculation of the peak (1) (m/z 459.0922) composition of a solution of the thiol-degraded 10K NBP-A fraction.

FIG. 16-4 shows the results of calculation of the peak (1) (m/z 459.0922) composition of a solution of the thiol-degraded 10K NBP-A fraction (continuation of FIG. 16-3).

FIG. 17-1 shows the results of LC-MS assay of peak (2) of a solution of the thiol-degraded 10K NBP-A fraction.

FIG. 17-2 shows the accurate mass spectra of peak (2) of a solution of the thiol-degraded 10K NBP-A fraction.

FIG. 17-3 shows the results of calculation of the peak (2) (m/z 413.1041) composition of a solution of the thiol-degraded 10K NBP-A fraction.

FIG. 17-4 shows the results of calculation of the peak (2) (m/z 413.1041) composition of a solution of the thiol-degraded 10K NBP-A fraction (continuation of FIG. 17-3).

FIG. 18-1 shows the results of LC-MS assay of peak (3) of a solution of the thiol-degraded 10K NBP-A fraction.

FIG. 18-2 shows the accurate mass spectra of peak (3) of a solution of the thiol-degraded 10K NBP-A fraction.

FIG. 18-3 shows the results of calculation of the peak (3) (m/z 565.1229) composition of a solution of the thiol-degraded 10K NBP-A fraction.

FIG. 18-4 shows the results of calculation of the peak (3) (m/z 565.1229) composition of a solution of the thiol-degraded 10K NBP-A fraction (continuation of FIG. 18-3)

Figure 1:
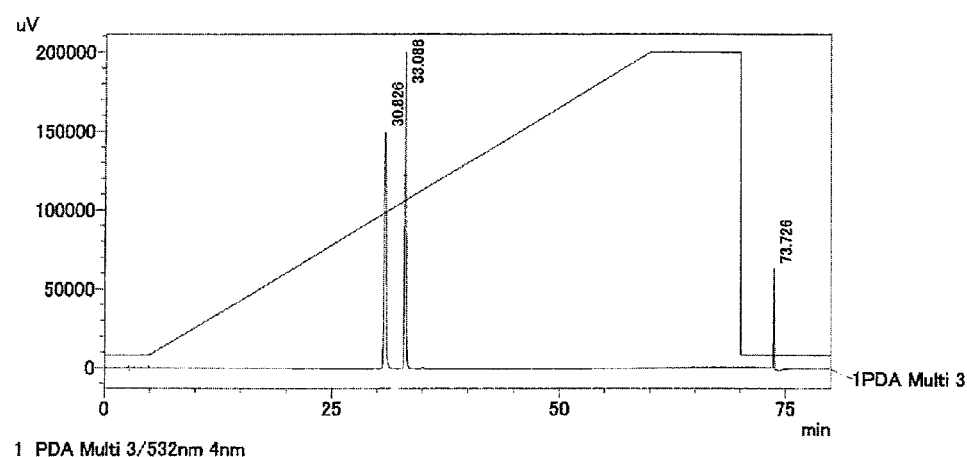
FIG. 1 shows the results of HPLC analysis of cashew apple-derived proanthocyanidin heated under acidic conditions.
Figure 1:
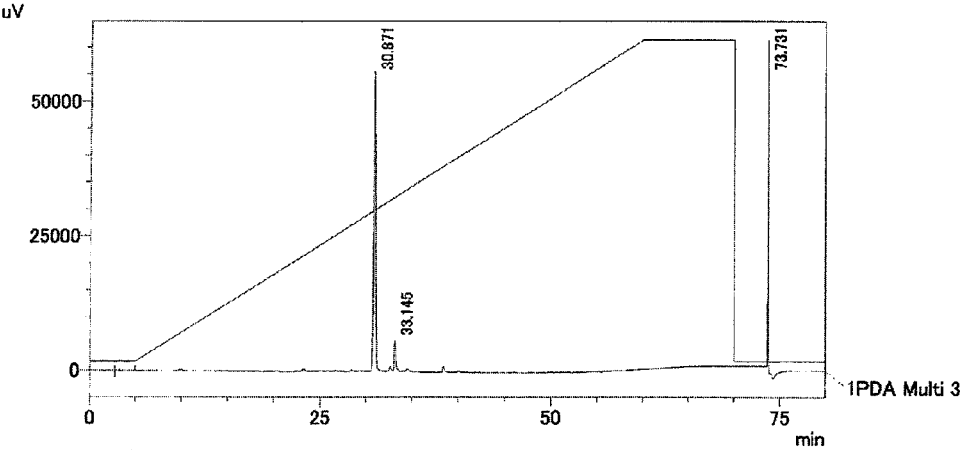
Figure 1:
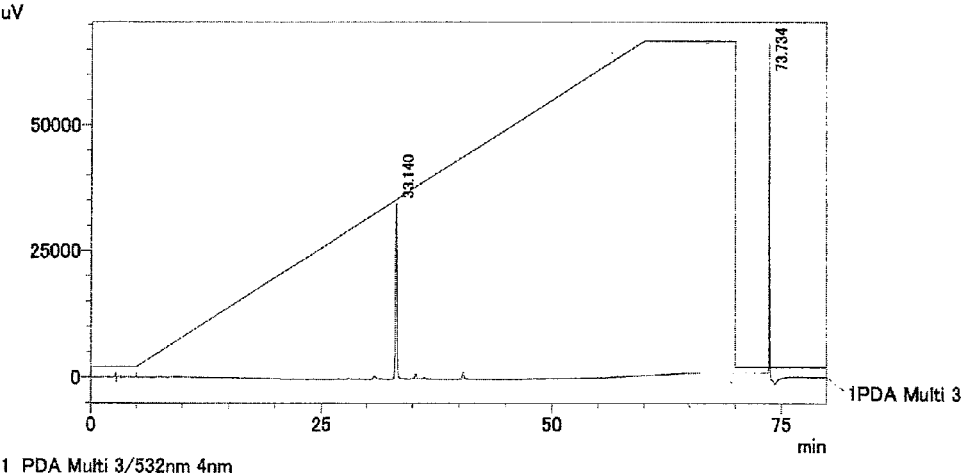

This description includes part or all of the contents as disclosed in the description and/or drawings of the International Application PCT/JP2008/073843, which is a priority document of the present application.

BEST MODES FOR CARRYING OUT THE INVENTION

1. Cashew Apple

In the present invention, a yellow pear-shaped region, which is a swollen stalk of *Anacardium occidentale*, can be used as a cashew apple. Cashew nuts and husks thereof generated at the ends thereof are removed.

In the present invention, the term "cashew apple(s)" refers not only to those retaining the original shape of cashew apple but also physically processed forms of cashew apple, such as ground products, puree, fruit juice, and squeezed residue of cashew apple fruit juice. The cashew apple puree is particularly preferable for the application of the present invention. Puree is obtained by grinding a husked ripe cashew apple with a grinder, blender, or other means and liquefying the ground product. A ripe cashew apple has a very soft fruit and thus can be easily liquefied.

High-molecular-weight proanthocyanidin can be separated from a water-insoluble ingredient such as pectin by allowing a plant fiber-degrading enzyme such as pectinase to react with a cashew apple. When a plant fiber-degrading enzyme is allowed to react, accordingly, water-insoluble cashew apple ingredients, such as squeezed residue of fruit juice, can be used as "cashew apple."

2. Processed Product of Cashew Apple

The present inventors found that a product obtained by degrading cashew apple using a plant fiber-degrading enzyme has satisfactorily high alpha-amylase inhibitory activity, lipase inhibitory activity, and antibacterial activity against *Propionibacterium acnes*. They deduced that high-molecular-weight proanthocyanidin having a novel structure would be associated with such types of activity. Accordingly, a proanthocyanidin-containing composition, such as a product of cashew apple degraded by a plant fiber-degrading enzyme, and proanthocyanidin are described below in detail.

2.1. Composition Containing Cashew Apple-Derived Proanthocyanidin

In the present invention, the term "proanthocyanidin-containing composition" or "composition containing proanthocyanidin" refers to a concentrate containing proanthocyanidin in such a manner that it is capable of functioning, which is obtained by allowing a plant fiber-degrading enzyme to react with a cashew apple (including ground products, puree, fruit juice, and water-insoluble ingredients (squeezed residue of fruit juice)) to obtain a product degraded by a plant fiber-degrading enzyme, and further concentrating the product with the use of an ultrafiltration membrane, and a processed cashew-apple product, which is obtained by further processing the concentrated product (for example, by purifying it), containing cashew-apple-derived proanthocyanidin.

Cashew apple-derived proanthocyanidin comprises prodelphinidin as a main ingredient. Typically, prodelphinidin ((epi)gallocatechin and (epi)gallocatechin gallate) account for 70% to 100% by mole of the constitutional units of cashew apple-derived proanthocyanidin.

As "a plant fiber-degrading enzyme," pectinase, cellulase, hemicellulase, β-amylase, an enzyme having two or more of the activities of the aforementioned enzymes, or a mixture of such enzymes is preferable, with pectinase being particularly preferable. Pectinase is known to have effects of clarifying fruit juice. In the present invention, a commercially available enzyme preparation can be used as a plant fiber-degrading enzyme. In addition to an enzyme preparation that is commercialized as pectinase, an enzyme preparation that is commercialized as an enzyme having another type of activity, such as a cellulase, but can be used as pectinase can also be used as pectinase in the present invention.

Conditions for treatment with a plant fiber-degrading enzyme may be adequately determined in accordance with the type of enzyme preparation to be used and the concentration thereof, and the relevant conditions are not particularly limited. It is preferable that enzyme treatment be carried out until the solid component of the enzyme-processed product can be easily precipitated via centrifugation or other means or easily separated via filtration. For example, enzyme treatment can be carried out at a pH of 3 to 5 at 50° C. to 60° C. for 1 to 24 hours.

A plant fiber-degrading enzyme is preferably allowed to react with puree or a water-insoluble ingredient of cashew apple. Cashew apple puree may further be diluted with a solvent, such as water. Use of a water-insoluble ingredient, such as squeezed residue of fruit juice, is preferable from the viewpoint of effective use of waste.

The enzyme-degraded product obtained by the process of a plant fiber-degrading enzyme reaction can be further subjected to the subsequent processes in that state. Since proanthocyanidin is eluted into a liquid portion, a liquid portion may be selectively separated via a common separation means, such as centrifugation or filtration, and then subjected to subsequent processes.

Further, it is preferable that the enzyme-degraded product obtained by the process of a plant fiber-degrading enzyme reaction be subjected to treatment, such as concentration through an ultrafiltration membrane (hereafter, it may be referred to as "the process of ultrafiltration"), concentration or separation of polyphenol (hereafter, it may be referred to as "the process of polyphenol separation"), or concentration or separation of proanthocyanidin (hereafter, it may be referred to as "the process of proanthocyanidin separation").

By the process of concentration through an ultrafiltration membrane, monosaccharides and disaccharides, such as fructose and glucose, contained in cashew apple can be removed, and calories and sweetness of a cashew apple product degraded by a plant fiber-degrading enzyme can be suppressed. Since a polymeric component concentrated via concentration through an ultrafiltration membrane contains high-molecular-weight proanthocyanidin, a concentrate obtained by such processing has high alpha-amylase inhibitory activity, lipase inhibitory activity, and antibacterial activity against *Propionibacterium acnes*.

An ultrafiltration membrane generally blocks particles or polymers of 0.1 μm to 2 nm (a molecular weight of several hundreds to several millions). In the present invention, use of an ultrafiltration membrane having a molecular weight cut-off that is capable of removing monosaccharides and disaccharides is preferable. A nominal molecular weight cut-off for a membrane is preferably 10,000 or greater, more preferably 30,000 or greater, and further preferably 50,000 or greater. For example, a membrane having a nominal molecular weight cut-off of 10,000 to 200,000 or 10,000 to 100,000 can be used.

Ultrafiltration conditions are not particularly limited. Materials that constitute an ultrafiltration membrane are not particularly limited, and a polyethersulfone- or cellulose-based membrane can be preferably used.

A concentrate obtained through an ultrafiltration membrane can be used for the applications of the present invention in that state or after further concentration or dehydration.

Concentration or separation of polyphenol can be carried out with the use of a synthetic adsorbent that adsorbs polyphenol by concentrating or separating polyphenol in the enzyme-degraded product obtained by the process of a plant fiber-degrading enzyme reaction or the concentrate obtained by the process of ultrafiltration. It is particularly preferable that the concentrate obtained by the process of ultrafiltration be subjected to concentration or separation of polyphenol. An example of a synthetic adsorbent that can be used is a microporous resin having an insoluble, three-dimensional, and crosslinked polymeric structure, a high specific surface area, and an aromatic chemical composition (e.g., styrene-divinylbenzene). Specific examples of commercially available products include Diaion®/Sepabeads® HP-20 (Mitsubishi Chemical Corporation). In addition, a product resulting from chemical modification of the aforementioned aromatic resin or a product resulting from alteration of micropore sizes can be preferably used. Further, concentration or separation of polyphenol can be carried out with the use of a resin obtained by introducing octadecyl (C18) or octyl (C8) into bonded silica gel as a functional group.

A procedure of concentration or separation of polyphenol using a synthetic adsorbent is not particularly limited. For example, the enzyme-degraded product obtained by the process of a plant fiber-degrading enzyme reaction or the concentrate obtained by the process of ultrafiltration is allowed to pass through a column filled with a synthetic adsorbent, the content of the column is washed with a wash solution such as water, and polyphenol is eluted with the use of an eluate such as acetone or an aqueous alcohol solution. Thus, concentration or separation of polyphenol can be carried out. The eluted substance can be adequately concentrated or dehydrated. The thus-obtained polyphenol component contains proanthocyanidin (described below) as a roughly purified product.

Concentration or separation of proanthocyanidin can be carried out with the use of a synthetic adsorbent that adsorbs proanthocyanidin by concentrating or separating proanthocyanidin in the enzyme-degraded product obtained by the process of a plant fiber-degrading enzyme reaction, the concentrate obtained by the process of ultrafiltration, or the concentrated or separated polyphenol obtained by the process of polyphenol separation. It is particularly preferable that the concentrated or separated polyphenol be subjected to concentration or separation of proanthocyanidin. An example of a synthetic adsorbent that can be used is a resin prepared from hydroxypropylated dextran. A substance having a particle diameter of 18 to 111 μm on a dry basis and 27 to 163 μm when swollen with methanol and stability in water, a salt solution, an organic solvent, and a denaturing agent is preferable. A specific example of a commercial product is Sephadex LH-20 resin (GE Healthcare).

Procedures for concentration or separation of proanthocyanidin using a synthetic adsorbent are not particularly limited. For example, the enzyme-degraded product obtained by the process of a plant fiber-degrading enzyme reaction, the concentrate obtained by the process of ultrafiltration, or the concentrated or separated polyphenol obtained by the process of polyphenol separation is allowed to pass through a column filled with a synthetic adsorbent, the content of the column is washed with a wash solution such as water, and proanthocyanidin is eluted with the use of an eluate such as acetone or alcohol. Thus, concentration or separation of proanthocyanidin can be carried out. The eluted substance can be adequately concentrated or dehydrated. The thus-obtained proanthocyanidin component contains proanthocyanidin (described below) in a substantially purified state. Such substantially purified proanthocyanidin is within the scope of the "composition containing proanthocyanidin" of the present invention.

The concentrated or separated polyphenol or the concentrated or separated proanthocyanidin obtained through the above procedures can be further fractionated in accordance with the molecular weight through an ultrafiltration membrane. In such case, the ultrafiltration membrane and the ultrafiltration conditions as described above can be adopted.

The cashew apple-derived proanthocyanidin-containing composition obtained through the above procedure is a novel composition that did not exist in the past, and this composition has advantages such as high alpha-amylase inhibitory activity, high lipase inhibitory activity, and high antibacterial activity against *Propionibacterium acnes*.

The proanthocyanidin-containing composition of the present invention is prepared by a method comprising a process of allowing a plant fiber-degrading enzyme to react with a cashew apple (i.e., the process of a plant fiber-degrading enzyme reaction) and a process of concentrating the enzyme-degraded product obtained by the process of a plant fiber-degrading enzyme reaction through the ultrafiltration membrane (i.e., the process of ultrafiltration). It is preferable that cashew apple used for the process of a plant fiber-degrading enzyme reaction at least comprise a water-insoluble ingredient, such as pectin.

More preferably, the proanthocyanidin-containing composition of the present invention is prepared by a method comprising the process of a plant fiber-degrading enzyme reaction, the process of ultrafiltration, and a process of concentrating or separating polyphenol from the concentrate obtained by the process of ultrafiltration (i.e., the process of polyphenol separation).

More preferably, the proanthocyanidin-containing composition of the present invention is prepared by a method comprising the process of a plant fiber-degrading enzyme reaction, the process of ultrafiltration, and a process of concentrating or separating proanthocyanidin from the concentrate obtained by the process of ultrafiltration (i.e., the process of proanthocyanidin separation).

More preferably, the proanthocyanidin-containing composition of the present invention is prepared by a method comprising the process of a plant fiber-degrading enzyme reaction, the process of ultrafiltration, the process of polyphenol separation for concentrating or separating polyphenol from the concentrate obtained by the process of ultrafiltration, and the process of proanthocyanidin separation for concentrating or separating proanthocyanidin from a polyphenol-containing composition obtained by the process of polyphenol separation.

The product degraded by the plant fiber-degrading enzyme obtained by the process of a plant fiber-degrading enzyme reaction is considered to contain cashew apple-derived proanthocyanidin in such a manner that the activity thereof can be exerted.

The composition obtained through the process of ultrafiltration is considered to contain proanthocyanidin with an increased amount of a high-molecular-weight component that is not filtered through an ultrafiltration membrane.

The composition obtained through the process of polyphenol separation is considered to contain proanthocyanidin with other polyphenol fractions. Such composition is equivalent to roughly purified proanthocyanidin.

The composition obtained through the process of proanthocyanidin separation is considered to contain proanthocyanidin at a further elevated concentration. Such composition is equivalent to purified proanthocyanidin.

2.2. Proanthocyanidin

Proanthocyanidin separated from a product of cashew apple degraded by a plant fiber-degrading enzyme prepared by a method comprising a step of allowing a plant fiber-degrading enzyme to react with a cashew apple is a novel compound. Such proanthocyanidin has advantages such as high alpha-amylase inhibitory activity, high lipase inhibitory activity, and high antibacterial activity against *Propionibacterium acnes*, as described in the examples. Specifically, the present invention also provides a novel form of proanthocyanidin.

The proanthocyanidin of the present invention is a polymer with an average degree of polymerization of at least 20, which at least contains, as constitutional units, gallocatechin or epigallocatechin (referred to as "(epi)gallocatechin" herein) and gallocatechin gallate or epigallocatechin gallate (referred to as "(epi)gallocatechin gallate" herein). The average degree of polymerization is preferably at least 25, more preferably 25 to 100, and particularly preferably 25 to 75. It is preferable that the proanthocyanidin of the present invention further contain epicatechin and epicatechin gallate as constitutional units.

The proanthocyanidin of the present invention contains preferably 50% to 80% by mole (epi)gallocatechin and 20% to 50% by mole (epi)gallocatechin gallate, and more preferably 50% to 75% by mole (epi)gallocatechin, 20% to 45% by mole (epi)gallocatechin gallate, 3% to 10% by mole epicatechin, and 0.5% to 5% by mole epicatechin gallate as constitutional units. The proanthocyanidin of the present invention contains (epi)gallocatechin and (epi)gallocatechin gallate as main ingredients. Accordingly, it may be referred to as "prodelphinidin" herein.

The constitutional unit (the repeat unit) of the proanthocyanidin of the present invention is represented by the following formula 1:

[Chemical formula 1]

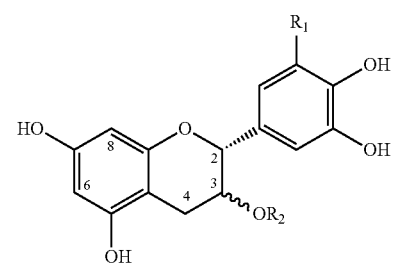

wherein $R_1$ represents a hydroxyl group, $R_2$ represents a hydrogen atom, and a substituent at position 2 and a $—OR_2$ group at position 3 on the chroman ring are in a cis or trans configuration in the case of (epi)gallocatechin;

$R_1$ represents a hydroxyl group, $R_2$ represents a group represented by formula 2 (gallate group):

[Chemical formula 2]

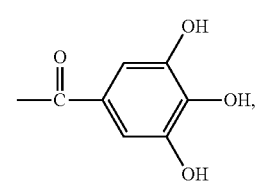

and a substituent at position 2 and a $—OR_2$ group at position 3 on the chroman ring are in a cis or trans configuration in the case of (epi)gallocatechin gallate;

$R_1$ represents a hydrogen atom, $R_2$ represents a hydrogen atom, and a substituent at position 2 and a —$OR_2$ group at position 3 on the chroman ring are in a cis configuration in the case of epicatechin; and $R_1$ represents a hydrogen atom, $R_2$ represents the gallate group, and a substituent at position 2 and a —$OR_2$ group at position 3 on the chroman ring are in a cis configuration in the case of epicatechin gallate.

The proanthocyanidin of the present invention is polymerized via a covalent bond between carbon at position 4 on the chroman ring of the flavonoid skeleton as a constitutional unit and another site of the adjacent constitutional unit (deduced to be carbon at position 8 or 6 on the chroman ring). In a cashew apple, the repeat unit at the end of carbon at position 4 of proanthocyanidin (i.e., the lower end unit) is epigallocatechin gallate. Specifically, the structure of the proanthocyanidin of the present invention is deduced to be as follows:

[Chemical formula 3]

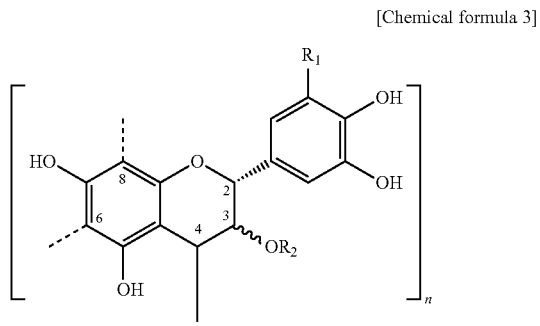

wherein a broken line on carbon at position 8 and a broken line on carbon at position 6 each represent a bond to carbon at position 4 of the adjacent repeat unit, another broken line represents hydrogen, the configuration of $R_1$, $R_2$, and the —$OR_2$ group are as defined above, $R_1$ represents a hydroxyl group, $R_2$ represents a gallate group, and a substituent at position 2 and a —$OR_2$ group at position 3 on the chroman ring are in a cis configuration in the lower end unit, and the number of repeat units (n) (i.e., the degree of polymerization) is preferably 20 or more, more preferably 25 or more, further preferably 25 to 100, and particularly preferably 25 to 75.

In the present invention, the proportion and the average degree of polymerization for constitutional units can be calculated based on the types of constitutional units contained in a degradation product and molar concentrations of the constitutional units determined by a thiol degradation method. The thiol degradation method comprises a step of thiol degradation comprising allowing proanthocyanidin to react with benzyl mercaptan under acidic conditions to degrade proanthocyanidin with thiol, and a step of instrumental analysis analyzing the types of constitutional units contained in the degradation product and molar concentrations of the constitutional units with the use of an instrument such as high-performance liquid chromatography (HPLC), mass analysis, and the like (see Non-Patent Document 3 and Example 5). A constitutional unit that does not form a benzyl thioether derivative in the degraded product is determined to be a constitutional unit constituting the lower end unit.

The proanthocyanidin of the present invention can be prepared from cashew apple by a method comprising the process of a plant fiber-degrading enzyme reaction, the process of ultrafiltration, the process of polyphenol separation, and the process of proanthocyanidin separation.

3. Applications

Hereafter, advantageous activities of cashew apple-derived proanthocyanidin and applications utilizing such activities are described.

3.1. Alpha-Amylase Inhibitory Activity

Cashew apple-derived proanthocyanidin has alpha-amylase inhibitory activity. By inhibiting alpha-amylase, postprandial rapid elevation in blood glucose levels can be reduced. Accordingly, cashew apple-derived proanthocyanidin can be used as an active ingredient of a preventive or therapeutic agent for a condition or disease (e.g., inhibitor of elevation in blood glucose levels, diabetes, or obesity) that is prevented or improved via inhibition of alpha-amylase.

The alpha-amylase inhibitor and the preventive or therapeutic agent for a condition or disease that is prevented or improved via inhibition of alpha-amylase according to the present invention may be in any form, such as in the form of a pharmaceutical or food product. Specifically, the present invention provides a food or beverage composition or pharmaceutical composition having alpha-amylase inhibitory activity, activity of preventing or treating a condition or disease that is prevented or improved via inhibition of alpha-amylase, activity of lowering the risk of developing such condition or disease, or activity of inducing physiological effects that can serve as bases for the prevention or treatment of such condition or disease. It is preferable that the amylase inhibitor or preventive or therapeutic agent be provided in the form of a food or beverage composition or a pharmaceutical composition to be orally administered.

For example, a plant fiber-degrading enzyme is allowed to react with puree or a water-insoluble ingredient of cashew apple, and a product thereof obtained via concentration through an ultrafiltration membrane can be used as a food or beverage composition or pharmaceutical composition having alpha-amylase inhibitory activity or activity associated therewith.

A food or beverage composition containing cashew apple-derived proanthocyanidin in such a manner that 2.2 mg or more, preferably 7.5 mg or more, more preferably 25 mg or more, and particularly preferably 50 mg or more thereof can be ingested per meal is useful as a food or beverage composition having alpha-amylase inhibitory activity or activity associated therewith. The upper limit of the amount of cashew apple-derived proanthocyanidin is not particularly limited, and it is generally 10 g or less per meal. Food or beverage composition per meal refers to, for example, a food or beverage composition of 100 g.

3.2. Lipase Inhibitory Activity

Cashew apple-derived proanthocyanidin has lipase inhibitory activity. Cashew apple-derived proanthocyanidin has more effective inhibitory activity than known active ingredients on lipase produced from bacteria, as well as on lipase derived from the pancrease. By inhibiting lipase activity, systemic absorption of lipids after ingestion thereof is suppressed. Thus, obesity or hyperlipidemia can be prevented or treated. By inhibiting lipase activity, also, lipid degradation caused by lipase produced by microorganisms when lipid-containing food or beverage products, such as food, or cosmetic products are contaminated with microorganisms is suppressed, and deterioration of lipids, such as in the case of worsening odor, can be suppressed. Further, activity of lipase produced by bacteria that are present on the skin surface can be inhibited, and skin diseases such as pimples caused by lipase activity can be prevented or treated. Thus, cashew apple-derived proanthocyanidin is useful as an active ingredient of a preventive or therapeutic agent for a condition or disease that is prevented or improved via inhibition of lipase activity, such as obesity, hyperlipidemia, or pimples, or an inhibitor of lipid deterioration.

The lipase inhibitor, the inhibitor of lipid deterioration, and the preventive or therapeutic agent for a condition or disease that is prevented or improved via inhibition of lipase of the present invention may be in any form, such as in the form of pharmaceutical, cosmetic, or food products. Specifically, the present invention provides a food or beverage composition, cosmetic composition, or pharmaceutical composition having lipase inhibitory activity, activity of suppressing lipid deterioration, activity of preventing or treating a condition or disease that is prevented or improved via inhibition of lipase, activity of reducing the risk of developing said condition or disease, or activity of inducing physiological effects that can serve as bases for prevention or treatment of said condition or disease. The lipase inhibitor, the inhibitor of lipid deterioration, and the preventive or therapeutic agent are preferably provided in the form of a food or beverage composition, a pharmaceutical or cosmetic composition applied to the skin, or a pharmaceutical composition used for oral administration.

A food or beverage composition, cosmetic composition, or pharmaceutical composition comprising cashew apple-derived proanthocyanidin in an amount of preferably 0.001% by weight to 10% by weight, more preferably 0.01% by weight to 5% by weight, further preferably 0.025% by weight to 5% by weight, and particularly preferably 0.05% by weight to 5% by weight is particularly useful as a food or beverage composition, cosmetic composition, or pharmaceutical composition having lipase inhibitory activity or activity associated therewith.

3.3. Antibacterial Activity

Cashew apple-derived proanthocyanidin exhibits antibacterial activity against *Escherichia coli, Pseudomonas aeruginosa, Staphylococcus aureus*, and *Propionibacterium acnes*, and it exhibits particularly strong growth inhibitory activity against *Propionibacterium acnes*. Accordingly, cashew apple-derived proanthocyanidin is effective for treatment or prevention of a condition or disease that is prevented or improved via inhibition of the growth of *Propionibacterium acnes*, such as pimples.

The antibacterial agent against *Propionibacterium acnes* and a preventive or therapeutic agent for a condition or disease that is prevented or improved via inhibition of the growth of *Propionibacterium acnes* of the present invention may be in any form, such as in the form of a pharmaceutical or cosmetic product. Specifically, the present invention provides a cosmetic or pharmaceutical composition having antibacterial activity against *Propionibacterium acnes*, activity of preventing or treating a condition or disease that is prevented or improved via inhibition of the growth of *Propionibacterium acnes*, activity of reducing the risk of developing said condition or disease, or activity of inducing physiological effects that can serve as bases for prevention or treatment of said condition or disease. The antibacterial agent and the preventive or therapeutic agent are preferably provided in the form of a cosmetic or pharmaceutical composition that is applied to the skin.

The amount of cashew apple-derived proanthocyanidin to be contained in the cosmetic or pharmaceutical composition varies depending on dosage form or degree of effects expected. It is generally 0.0001% by weight or more, preferably about 0.001% to 10% by weight, more preferably 0.025% by weight to 10% by weight, and particularly preferably 0.05% by weight to 10% by weight.

3.4. Form of Composition

The cashew apple-derived proanthocyanidin of the present invention or a processed cashew apple product containing the same can be incorporated into a food or beverage composition, cosmetic composition, or pharmaceutical composition.

The food or beverage composition can be in the form of, for example, a beverage product, solid food, or semi-solid food product. The food or beverage composition can be a specified health food. Specific examples of beverage products include fruit juice, soft drink, and alcohol beverage products. Beverage products may be a product to be diluted with water or the like at the time of ingestion thereof. Solid food products can exist in a variety of forms, such as tablets or sugar-coated tablets, including candies and troches, granules, powdery forms such as powdery beverages and soup powder, block-shaped confectionaries such as biscuits, capsules, and jellies. Examples of semi-solid forms of food products include pastes such as jam and gum such as chewing gum. In addition to the cashew apple-derived proanthocyanidin of the present invention or a processed cashew apple product containing the same, such food or beverage composition can contain a variety of ingredients that are generally used as food raw materials, provided that the desired effects of the present invention are maintained. Examples of other ingredients include water, an alcohol, a sweetening agent, an acidifier, a colorant, a preservative, an aroma chemical, and an excipient. Such ingredients can be used alone or in combination. The amount of cashew apple-derived proanthocyanidin contained in the food or beverage composition of the present invention is preferably an amount effective for exhibiting alpha-amylase inhibitory activity or lipase inhibitory activity upon ingestion.

A cosmetic composition can be used in general forms, such as cosmetic creams, emulsions, lotions, beauty essences, facial masks, powders, skin care cosmetics, lip balms, lipsticks, makeup bases, foundations, sun protection agents, bath agents, body washes, body lotions, washes, ointments, jelly agents, or aerosols. In addition to the cashew apple-derived proanthocyanidin of the present invention or a processed cashew apple product containing the same, for example, water, an oil, a surfactant, a lubricant, an alcohol, a water-soluble polymer, a gelling agent, a humectant, a buffer, a preservative, an anti-inflammatory agent, a thickener, an aroma chemical, a vitamin, an anti-oxidant, an ultraviolet absorber, a pigment, or a dye can be adequately added to the cosmetic composition, provided that the desired effects of the present invention are maintained. The amount of cashew apple-derived proanthocyanidin contained in the cosmetic composition of the present invention is preferably an amount effective for exhibiting lipase inhibitory activity or antibacterial activity against *Propionibacterium acnes* through the use thereof in the form of a cosmetic product.

A pharmaceutical composition prepared in any of a variety of dosage forms can be used. The dosage form is not particularly limited, and it is adequately selected according to need. In general, a pharmaceutical composition is used alone or in combination in the form of an oral preparation, such as a tablet, capsule, granule, fine grain, powder, pill, liquid, syrup, suspension, emulsion, or elixir, or a parenteral preparation, such as an injection, drop, suppository, inhalant, transmucosal absorbent, transnasal agent, enteral agent, or skin external agent (e.g., a transdermal absorbent, adhesive skin patch, or ointment), in accordance with symptoms. An alpha-amylase inhibitor is preferably in the form of an oral preparation and a lipase inhibitor is preferably in the form of an oral preparation or external skin preparation. An antibacterial agent against *Propionibacterium acnes* is preferably in the form of an external skin preparation.

The above preparations can be prepared by conventional techniques with the use of, for example, an excipient, binder, disintegrator, surfactant, lubricant, fluidizing agent, flavoring agent, colorant, or aroma chemical.

When an external skin preparation is prepared, in particular, ingredients such as a surfactant, oil and fat, wax, carbohydrate, alcohol, silicone oil, water-soluble polymer, solvent, dye, pigment, aroma chemical, anti-oxidant, humectant, vitamin, vitamin derivative, plant or animal extract, inorganic salt, pH modifier, antibacterial agent, or ultraviolet absorber can be adequately incorporated, according to need.

The amount of the preparation to be administered is determined so that it will effectively exhibit alpha-amylase inhibitory activity, lipase inhibitory activity, or antibacterial activity against *Propionibacterium acnes*, depending on the age of a patient, body weight, disease severity, or route of administration.

EXAMPLES

The present invention is described in greater detail with reference to the following examples.

Example 1

Effectiveness of Plant Fiber-Degrading Enzyme Treatment (1) Preparation of Specimens The alpha-amylase inhibitory activity of the fruit juice of cashew apple puree was compared with that of the fruit juice obtained by treating the former fruit juice with pectinase. Fruit juice without treatment was prepared by subjecting the thawed puree to centrifugation at 18,000 rpm for 20 minutes at 20° C., and filtering the supernatant thereof with the use of a 0.22-μm filter (Millex GP, Millipore). The resulting filtrate was designated as a fruit juice sample without treatment.

A pectinase-treated fruit juice sample was prepared by adding pectinase A "Amano" (Amano Enzyme Inc.) in an amount of 0.5% relative to the weight of the puree, and mixing the resultant with agitation at 50° C. for 90 minutes. The resulting enzyme-treated solution was subjected to centrifugation at 18,000 rpm for 15 minutes at 20° C., and the supernatant thereof was filtered through a 0.22-μm filter (Millex GP, Millipore). The resulting filtrate was designated as a pectinase-treated fruit juice sample. Since cashew apple puree cannot be sufficiently precipitated via centrifugation alone, cashew apple puree was treated with pectinase. This treatment facilitated filtration.

For a comparative purpose, the alpha-amylase inhibitory activity of a commercially available tea beverage (Banso Reicha®, Yakult) was also assayed. This tea beverage contains polyphenols from guava leaves containing a complex of tannin-like substances having a molecular weight ranging from 5,000 to 30,000. Carbohydrate that had entered the body as food is digested and degraded by a digestive enzyme and absorbed through the intestine in the form of glucose. Polyphenols from guava leaves have effects of suppressing the activity of a carbohydrate-degrading enzyme that degrades carbohydrates (e.g., sucrose or starch) into glucose or the like, delaying the absorption of sugar in the blood, and consequently slowing postprandial elevation in blood glucose levels. The effects and efficacy of such tea beverage were approved, and this tea beverage is approved as a specified health food product by the Ministry of Health, Labor and Welfare, Japan on Mar. 28, 2000.

(2) Assay of Alpha-Amylase Inhibitory Activity

Sample solutions of the above 3 types of specimens diluted with purified water (50 μl) were each mixed with 50 μl of porcine pancreatic alpha-amylase (SIGMA)/0.25M phosphate buffer (pH 7.0), and the resulting mixtures were preincubated at 37° C. for 10 minutes. The reaction was initiated by adding 100 μl of a 0.5% starch/phosphate buffer to the sample solutions. After incubation was carried out at 37° C. for 30 minutes, 1 ml of 0.1M hydrochloric acid was added to each test tube to terminate the enzyme reaction. These reaction solutions were thoroughly mixed, 100 μl each thereof was applied to a 96-well plate, 100 μl of a solution of 0.01M iodine was added thereto to color undegraded starch, and the absorbance at 660 nm was assayed with the use of a plate reader. Enzyme inhibition was determined by the formula shown below in comparison with a control blank solution. As blank samples, testing was carried out by altering the timing for addition of 100 μl of a 0.5% starch/phosphate buffer from after pre-incubation to after the termination of enzyme reaction by hydrochloric acid. Specifically, the enzyme solutions were mixed with the samples in the same manner, preincubation was carried out at 37° C. for 10 minutes, incubation was carried out for an additional 30 minutes, 1 ml of 0.1M hydrochloric acid was added to each test tube, and 100 μl of a 0.5% starch/phosphate buffer was added in the blank tests of the samples. In addition, the absorbance was assayed in the same manner as in the case of the test of sample solutions, except for the use of purified water that would not inhibit the enzyme activity instead of the samples (a purified water blank).

<Calculation Formula>

$$\text{Alpha-amylase inhibitory activity}(\%) = (1-(A-B)/(C-D)) \times 100$$

A: the absorption in the blank test using a sample solution
B: the absorption in the test using a sample solution
C: the absorption in the blank test using purified water
D: the absorption in the test using purified water Enzyme inhibitory activities of the sample solutions were assayed at a plurality of concentrations, and the concentration at which 50% of the alpha-amylase activity is inhibited ($IC_{50}$) was determined.

(3) Test Results

The concentrations of the cashew apple fruit juice sample without treatment, the cashew apple fruit juice sample treated with pectinase, and the tea beverage sample before dilution are each designated as 100%, and the results of comparison are shown below.

TABLE 1

| Samples | Alpha-amylase inhibitory activity ($IC_{50}$) |
|---|---|
| Cashew apple fruit juice sample without treatment | 5.4% |
| Cashew apple fruit juice sample treated with pectinase | 0.3% |
| Tea beverage sample | 2.5% |

The tea beverage sample (Banso Reicha®) inhibited 50% of alpha-amylase activity at a concentration of 2.5% (a 40-fold diluent). While $IC_{50}$ of the cashew apple fruit juice sample treated with pectinase was 0.3% (an approximately 333-fold diluent), that of the fruit juice sample without treatment was 5.4% (an approximately 18.5-fold diluent) (i.e., the inhibitory activity was very weak). The tea beverage sample used in the test is approved as a specified health food product since effects thereof for suppressing elevation in blood glucose levels in humans are approved. The alpha-amylase inhibitory activity of the cashew apple fruit juice sample treated with pectinase in terms of the $IC_{50}$ value is 8 times or more higher than that of the tea beverage sample. Accordingly, similar effects on humans can also be expected.

The cashew apple-derived proanthocyanidin of the present invention can be concentrated with the use of an ultrafiltration membrane having a molecular weight cut-off of 10,000. Thus, the cashew apple fruit juice sample treated with pectinase may be concentrated through an ultrafiltration membrane having a molecular weight cut-off of 10,000, low-molecular-weight components, such as fructose and glucose, may be removed therefrom, and the resulting concentrate may be used.

Example 2

Purification of Active Ingredient (Proanthocyanidin Polymers Derived from Cashew Apple)

Pectinase A "Amano" was added in an amount of 0.5% (23.9 g) relative to 4,773 g of cashew apple puree, and the resultant was agitated at 50° C. for 2.5 hours. The pectinase-treated solution was centrifuged at 4,200 rpm and 20° C. for 60 minutes, the supernatant was filtered through a 0.2-μm filter (SUPORLIFE® DCF, PALL), and 4,230 g of pectinase-treated fruit juice was collected. In order to mainly remove glucose and fructose from pectinase-treated fruit juice, concentration was carried out via ultrafiltration with the use of an ultrafiltration membrane having a molecular weight cut-off of 10,000 (Hydrosart®, 10 KDa, Sartorius), and 729 g of a concentrate (solid component: 26.4 g) was collected. Alpha-amylase inhibitory activity was not detected in fractions with a molecular weight of less than 10,000. In order to purify a polyphenol component from the concentrate, treatment was carried out with the use of Diaion®/Sepabeads® HP-20 (about 500 ml, Mitsubishi Chemical Corporation). Treatment was carried out in accordance with a conventional technique, the concentrate was allowed to pass through the resin filled in the column, the components were allowed to adsorb thereon, the resin was thoroughly washed with purified water, and the component of interest was then collected via elution with the use of an aqueous solution of 50% (W/W) ethanol. The eluate was dried with the use of a vacuum distillation concentrator. A solid component (3.7 g) was collected.

The component purified with the HP-20 resin (i.e., the HP-20 resin-purified product) was subjected to repurification with the use of Sephadex LH-20 resin (GE Healthcare), which is often carried out when separating proanthocyanidin. Resin (500 ml) swollen with an aqueous solution of 50% (W/W) methanol was filled in a column, the HP-20 resin-purified product dissolved in an aqueous solution of 50% (W/W) methanol was allowed to pass through the column, and the non-adsorbed component was washed with a sufficient amount of an aqueous solution of 50% (W/W) methanol. A fraction eluted with 100% methanol was dried via vacuum distillation, as a result of which 226.2 mg of NBP-M (a tentative name) was collected as an active ingredient. The resin that had been subjected to elution with methanol was further subjected to elution with an aqueous solution of 70% (V/V) acetone to collect the component of interest, and the collected component was dried via vacuum distillation, as a result of which 823.7 mg of NBP-A (a tentative name) was collected. NBP-M and NBP-A are deduced to be high-molecular-weight proanthocyanidins based on purification techniques.

Example 3

Molecular Weight and Alpha-Amylase Inhibitory Activity of Active Ingredient (1) Molecular Weight Cut-Off of Active Ingredient In order to examine the molecular size distribution of the cashew apple proanthocyanidin polymers purified with LH-20 resin (tentative name: NBP-M and NBP-A), a centrifugal ultrafiltration device (Amicon Ultra-15®, Millipore) was used to perform molecular weight cut-off treatment. In the test, NBP-M and NBP-A were dissolved in purified water, respectively, and the resulting solutions were applied to an ultrafiltration membrane (Ultracel-100K®) with a molecular weight cut-off of 100,000. The solution that had passed therethrough was further applied to an ultrafiltration membrane with a molecular weight cut-off of 50,000 (Ultracel-50K®), the solution that had passed therethrough was applied to an ultrafiltration membrane having a molecular weight cut-off of 30,000 (Ultracel-30K®), and the solution that had passed therethrough was further applied to an ultrafiltration membrane having a molecular weight cut-off of 10,000 (Ultracel-10K®) to prepare fractions. The resulting fractions were freeze-dried, and the molecular weight distributions of the molecular fractions were examined. As a result, many of proanthocyanidin polymers derived from cashew apple were found to exist in fractions of a molecular weight cut-off of 50,000 or more.

TABLE 2

Ultrafiltration fraction of cashew apple-derived proanthocyanidin polymer

| Ultrafiltration fraction (abbr.) | NBP-M weight distribution | NBP-A weight distribution |
| --- | --- | --- |
| 1) 100K or greater (100K) | 19.1% | 77.1% |
| 2) 100K to 50K (50K) | 28.4% | 11.5% |
| 3) 50K to 30K (30K) | 16.8% | 4.5% |
| 4) 30K to 10K (10K) | 35.7% | 6.9% |

(2) Alpha-Amylase Inhibitory Activity of Fraction

The distribution of each molecular fraction and the alpha-amylase inhibitory activity ($IC_{50}$) were assayed in the same manner as in Example 1 (2). The results are shown in the table below.

TABLE 3

Alpha-amylase inhibitory activity of cashew apple-derived proanthocyanidin polymer fraction

| Ultrafiltration fraction (abbr.) | Alpha-amylase inhibition $IC_{50}$ of NBP-M | Alpha-amylase inhibition $IC_{50}$ of NBP-A |
| --- | --- | --- |
| 1) 100K or greater (100K) | 1.7 μg/ml | 1.1 μg/ml |
| 2) 100K to 50K (50K) | 1.7 μg/ml | 1.5 μg/ml |
| 3) 50K to 30K (30K) | 1.9 μg/ml | 2.1 μg/ml |
| 4) 30K to 10K (10K) | 2.4 μg/ml | 3.0 μg/ml |

(3) Summary of Results

Regarding the acetone-eluted fraction (NBP-A), 88.6% of NBP-A was found to exist in a fraction having a molecular weight of 50,000 or greater, and the alpha-amylase inhibitory activity was found to be likely to be enhanced as the molecular weight was increased. However, a potent activity of 3.0 μg/ml was observed in a fraction having a molecular weight of 30 K to 10 K.

Regarding the methanol-eluted fraction (NBP-M), the alpha-amylase inhibitory activity was found to be likely to be enhanced as the molecular weight cut-off was increased, although there was no significant difference.

Example 4

Analysis of Molecular Structure of Active Ingredient 1

(1) Background

The term "proanthocyanidin" refers to a condensed tannin existing in various plants; i.e., compounds resulting from condensation or polymerization of flavan-3-ol or flavan-3,4-diol as constitutional units. That is, the term "proanthocyanidin" is a generic term of many polyphenols having different molecular structures, such as procyanidin that generates cyanidin (two groups among R1 to R3 shown in the formula below represent hydroxyl groups (OH) and a group represents hydrogen (H)), prodelphinidin that generates delphinidin (three groups of R1 to R3 shown in the formula below represent hydroxyl groups (OH)), and propelargonidin that generates pelargonidin (a group among R1 to R3 shown in the formula below represents a hydroxyl group (OH) and two groups represent hydrogen (H)) when heated under acidic conditions. Accordingly, heating in a hydrochloric acid/butanol solution and analysis of a type of the cyanidin enable deduction of the number of hydroxyl groups and a type of proanthocyanidin of R1 to R3.

[Chemical Formula 4]

Structure of repeat unit polymerized via C4→C8 bond contained in a flavan-3-ol polymer.

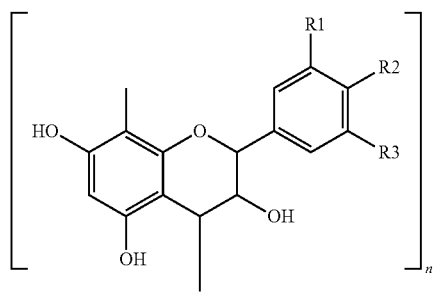

(2) Objective

A type of proanthocyanidin in NBP-A obtained from the cashew apple puree was analyzed. For a comparative purpose, grape seed-derived procyanidin composed of epicatechin and epicatechin gallate (Gravinol®, Kikkoman) was analyzed in the same manner.

(3) Method (i) Aqueous solutions of 0.1% (W/V) specimens in 50% ethanol were prepared and filtered through a 0.45-μm filter.

(ii) The resultant was mixed with the same amount of a solution of 5% (V/V) chloric acid/butanol and the mixture was heated at 95° C. for 1 hour.

(iii) The resultant was analyzed via HPLC (ODS-3 column). Analysis was carried out at the detection wavelength of 532 nm.

(iv) Specimens of the cyanidin and delphinidin reagents (Seikagaku Kogyo) at a concentration of 0.1% or lower were prepared, the resultants were subjected to HPLC under the same conditions, and the calibration curves were prepared.

(v) The amounts of anthocyanidins contained in the specimens were calculated based on the calibration curves.

(4) Results of Experiment

The results of analysis of the delphinidin and cyanidin reagents are shown in FIG. 1a. In FIG. 1a, the peak at 30.826 min indicates delphinidin and the peak at 33.088 min indicates cyanidin.

The results of analysis of NBP-A are shown in FIG. 1b. Since the peak at 30.871 min indicates delphinidin and the peak at 33.145 min indicates cyanidin, NBP-A was found to be mainly composed of prodelphinidin and to contain some procyanidins.

The results of analysis of Gravinol® (grape seeds) are shown in FIG. 1c. The peak at 33.140 min indicates cyanidin. The result is consistent with the fact that Gravinol® is procyanidin.

(5) Preparation of Delphinidin and Cyanidin from Specimens

The molecular weight cut-off fractions of NBP-M and NBP-A obtained in Example 3 were heated under acidic conditions in the same manner as in (3) above, and the delphinidin concentration and the cyanidin concentration were assayed.

The concentrations of delphinidin and cyanidin in the specimens generated under acidic conditions and the percentage of delphinidin generated (%) are shown in the table below.

TABLE 4

Results of tests of specimens

| Ultrafiltration fraction | Delphinidin concentration (%) | Cyanidin concentration (%) | Percentage of delphinidin (%) |
|---|---|---|---|
| 100K or greater NBP-M | 0.0166 | 0.0033 | 83.5 |
| 100K to 50K NBP-M | 0.0198 | 0.0036 | 84.7 |
| 50K to 30K NBP-M | 0.0165 | 0.0032 | 83.7 |
| 30K to 10K NBP-M | 0.0161 | 0.0031 | 83.7 |
| 100K or greater NBP-A | 0.0220 | 0.0035 | 86.3 |
| 100K to 50K NBP-A | 0.0211 | 0.0034 | 86.2 |
| 50K to 30K NBP-A | 0.0173 | 0.0030 | 85.0 |
| 30K to 10K NBP-A | 0.0151 | 0.0029 | 84.0 |
| Procyanidin C1* | 0 | 0.0205 | 0 |
| Gravinol ™ | 0 | 0.0104 | 0 |

*Procyanidin C1 represents an epicatechin trimer, which is a type of procyanidin.

Example 5

Analysis of Molecular Structure of Active Ingredient 2

Proanthocyanidin with a high degree of polymerization, which is composed of 6 or more flavan-3-ols bound to each other, has a complicated structure. Thus, the structure thereof cannot be analyzed via highly accurate MS or NMR analysis. Accordingly, the structure of proanthocyanidin is analyzed by a method wherein it is allowed to react with benzyl mercaptan represented by the formula below under acidic conditions to perform thiol degradation and analyzing the product thereof

[Chemical formula 5]

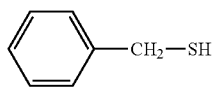

The degradation reaction is schematically shown below.

The structure of the obtained benzyl thioether derivative may be analyzed in order to analyze constitutional units of a condensed tannin.

Non-Patent Document 3 demonstrates an example in which proanthocyanidin of blueberries or the like is subjected to thiol degradation and analyzed via HPLC. According to this document, only epicatechin benzyl thioether was detected as a benzyl thioether derivative in the thiol-degraded products of proanthocyanidins from cocoa, a type of millet (brown sorghum bran), a type of wild-type blueberry (low-bush blueberry), and cranberry. This document also describes a method for calculating an average degree of polymerization of catechin and epicatechin polymers (i.e., mean DP (degree

[Chemical formula 6]

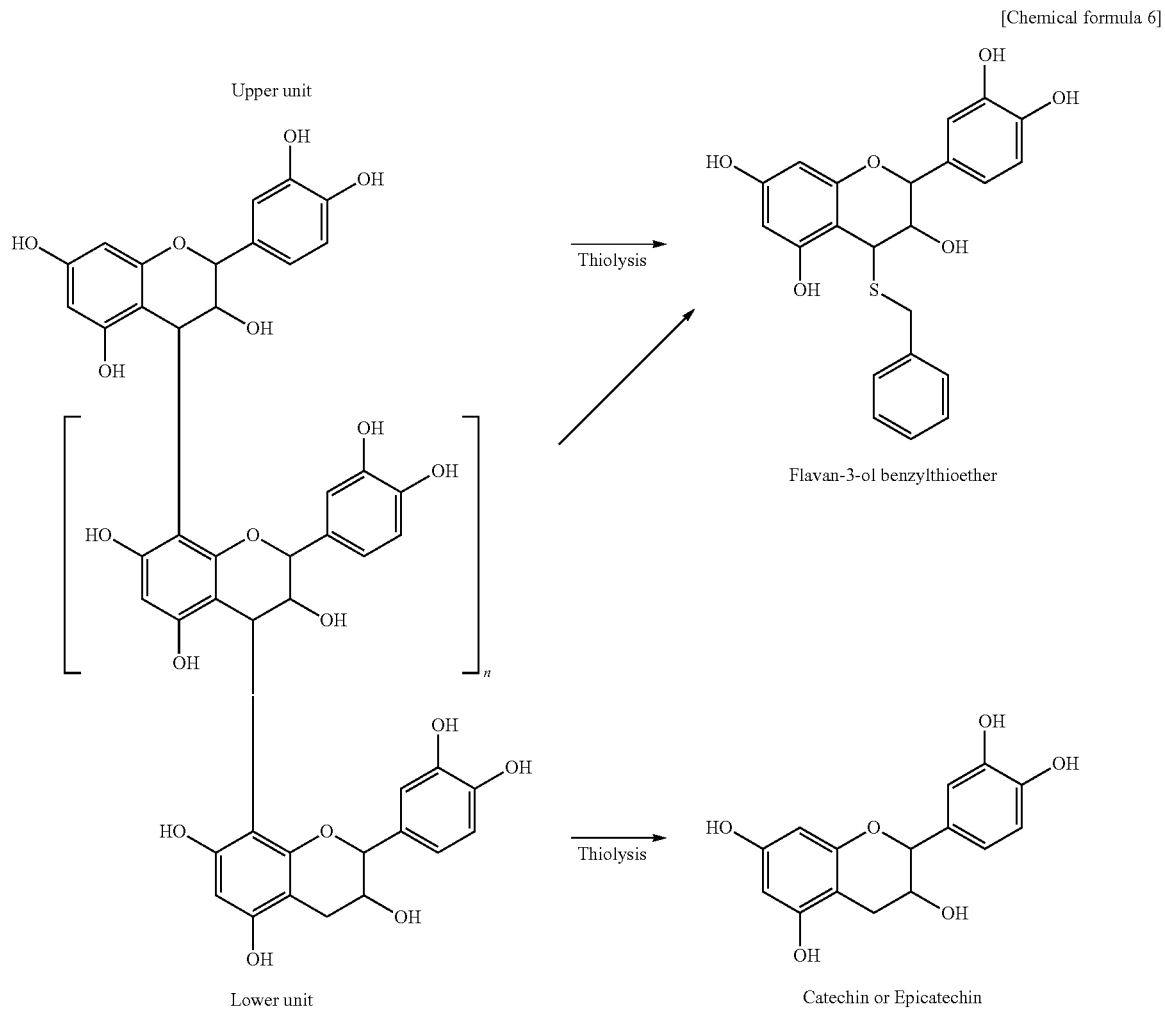

While the case in which a catechin condensate is subjected to thiol degradation is described in the above schematic diagram, a similar product is obtained when a condensate of (epi)gallocatechin or (epi)gallocatechin gallate is subjected to thiol degradation.

In the degradation reaction, the lower unit of a condensed tannin is released in that state (catechin and epicatechin: partially epimerized), and regions other than the lower unit are converted into derivatives in the form of benzyl thioether.

of polymerization)). HPLC analysis is carried out at 280 nm and the average degree of polymerization is determined based on the peak area.

mDP={total area of catechin benzyl thioether and epicatechin benzyl thioether}/{total area of catechin and epicatechin}+1

Figure 2:
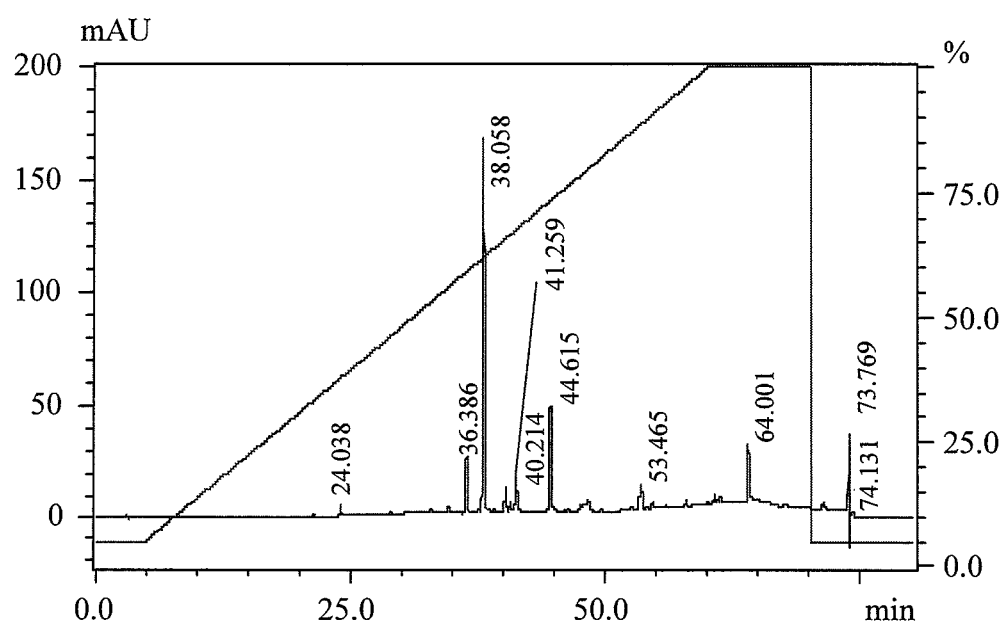
FIG. 2 shows the results of HPLC analysis of NBP-A (a 100 K or greater fraction) after thiol degradation.

(1) HPLC Analysis of Thiol-Degraded Proanthocyanidin Polymers Derived from Cashew Apple The NBP-M and NBP-A fractions obtained in Example 3 were subjected to thiol degradation, and differences in constituents were examined. Thiol degradation was carried out by mixing 250 μl of specimens dissolved in methanol at a concentration of 0.2% (W/V) with 250 μl of a 3.3% (V/V) hydrochloric acid/methanol solution, adding 500 μl of a 5% benzyl mercaptan/methanol solution thereto, heating the hermetically sealed tube at 40° C. for 30 minutes, and allowing the reaction to proceed at room temperature for 10 hours. HPLC analysis was carried out with the use of the ODS-3 column (4.6×250 mm, GL Sciences). Analysis was carried out using a linear gradient of purified water/methanol by adding 0.05% TFA at a flow rate of 1 ml/min. The results of HPLC analysis of thiol-degraded NBP-A (a 100 K or greater fraction) (detection wavelength: 280 nm) are shown in FIG. 2. A chromatogram substantially the same as that shown in FIG. 2 was obtained from NBP-M and NBP-A fractions other than the NBP-A fraction prepared in Example 3 (a 100K or greater fraction).

As a result, the thiol-degraded proanthocyanidin polymers derived from cashew apple were found to be mainly composed of 5 components (i.e., the peak at 36 min, the peak at 38 min, the peak at 24 min, the peak at 40 min, and the peak at 41 min in the chromatogram shown in FIG. 2) and to comprise, as main ingredients, components corresponding to the peak at 36 min and the peak at 38 min.

As a result of a comparison of the results of HPLC analysis of a reagent, a thiol-degraded procyanidin C1 (an epicatechin trimer), and a thiol-degraded procyanidin derived from grape seeds composed of epicatechin and epicatechin gallate (Gravinol®, Kikkoman), the peak at 36 min and the peak at 38 min were found to correspond to components that were not contained in thiol-degraded procyanidin C1 (an epicatechin trimer) or Gravinol®. Further, it was deduced that the peak at 24 min would correspond to epigallocatechin gallate, the peak at 40 min would correspond to a benzyl thioether derivative of epicatechin, and the peak at 41 min would correspond to a benzyl thioether derivative of epicatechin gallate.

(2) Structural Analysis of Major Constituents of Proanthocyanidin Polymers Derived from Cashew Apple In order to clarify the major constituents of the proanthocyanidin polymers derived from cashew apple, specimens of 100 K or greater NBP-A ultrafiltration fractions purified and separated in Example 3 were subjected to thiol degradation in the same manner as in (1) above, the component indicated by the peak at 36 min (i.e., the peak 1 component) and the component indicated by the peak at 38 min (i.e., the peak 2 component) were purified, and the structural analysis was carried out via ESI-MS and NMR.

(2-1) Analysis Sample

NBP-A (100 K or greater) that is a proanthocyanidin polymer derived from cashew apple (denoted as "NBP" in the description regarding the results of analysis and in the figures) (179 mg) was subjected to thiol degradation in the same manner as in (1) above, the resultant was diluted 5-fold with purified water, the resulting solution was applied to the C18 Cartridges (Sep-Pak Vac 35 cc, Waters), and the non-adsorbed component is washed with a sufficient amount of purified water. The component bound to the C18 resin was eluted with the aid of 50% methanol. The resultant was concentrated with a vacuum distillator and fractionated with HPLC columns for fractionation (ODS-3: 20×250 mm, GL Sciences). In the end, 29.5 mg of the peak 1 component and 27.2 mg of the peak 2 component were collected as purified products.

The obtained peak 1 and peak 2 components were subjected to the analysis described below as specimens.

(2-2) Items to be Analyzed (i) ESI-MS (ii) $^1$H NMR, $^{13}$C NMR (2-3) Method of Analysis (i) ESI-MS ESI-MS analysis was conducted under the following conditions.

TABLE 5

(ESI-MS conditions)

Apparatus: LCQ DECA XP plus-type mass spectrometer, Thermo Fisher Scientific K.K.
Method of sample introduction: direct introduction
Method of ionization: ESI(+)
Assay mode: MS
Mass range to be assayed: m/z 100 to 1,000

(ii) $^1$H NMR, $^{13}$C NMR

NMR assay was conducted under the following conditions.

TABLE 6

(NMR conditions)

Apparatus name: FT-NMR Apparatus JNM-ECA400, JEOL Ltd.
Resonance frequency: $^1$H: 400 MHz; $^{13}$C: 100 MHz
Assay mode: $^1$H NMR, $^{13}$C NMR
Solvent: deuterated acetone
Reference material: tetramethylsilane (TMS), 0 ppm (the internal standard method)
Method of sample preparation: A solvent (0.6 ml) was dissolved in the total amount of the sample.

Figure 3:
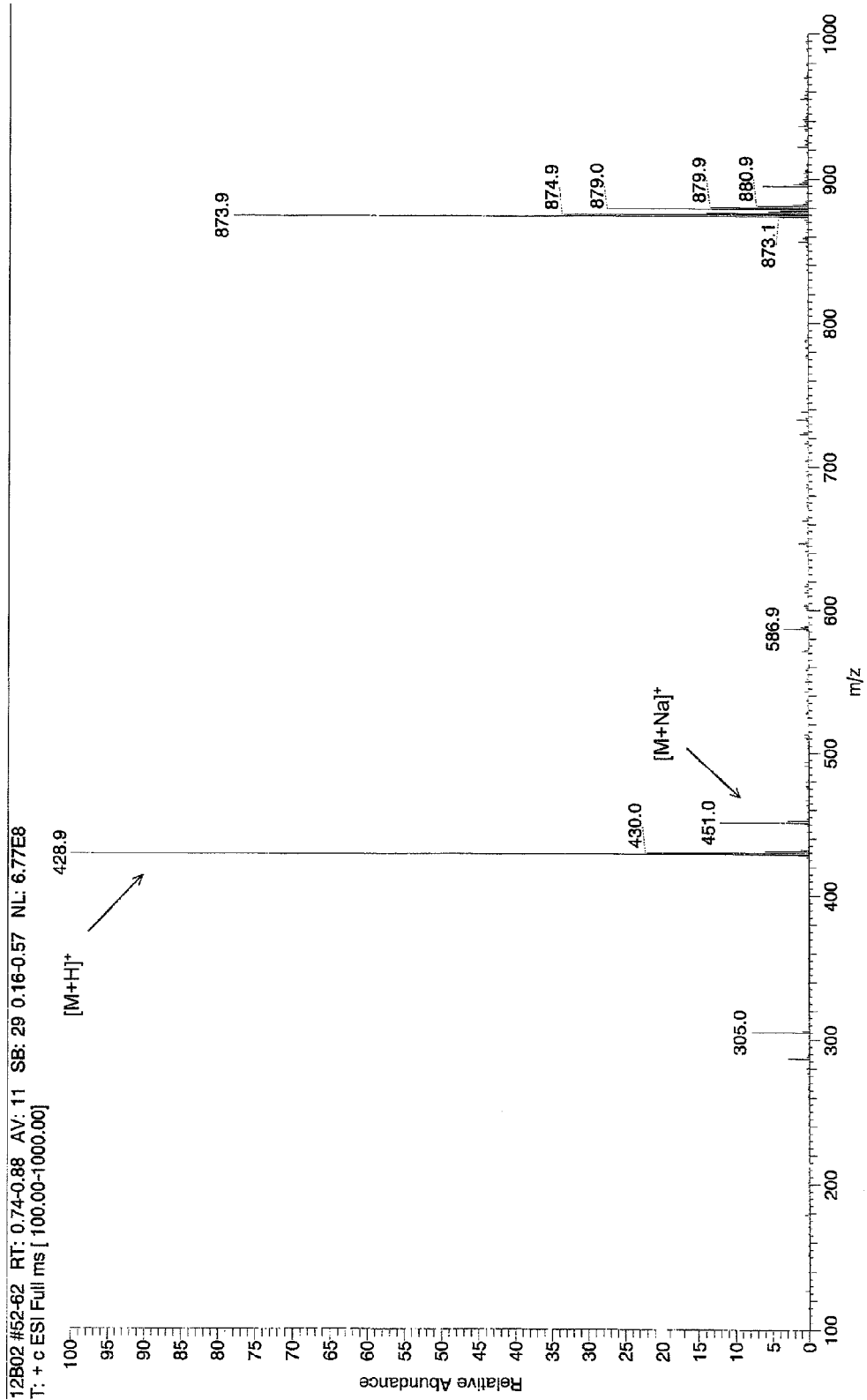
FIG. 3 shows the ESI(+)-MS spectra of the thiol-degraded and purified NBP (peak 1).
Figures 1, 4:
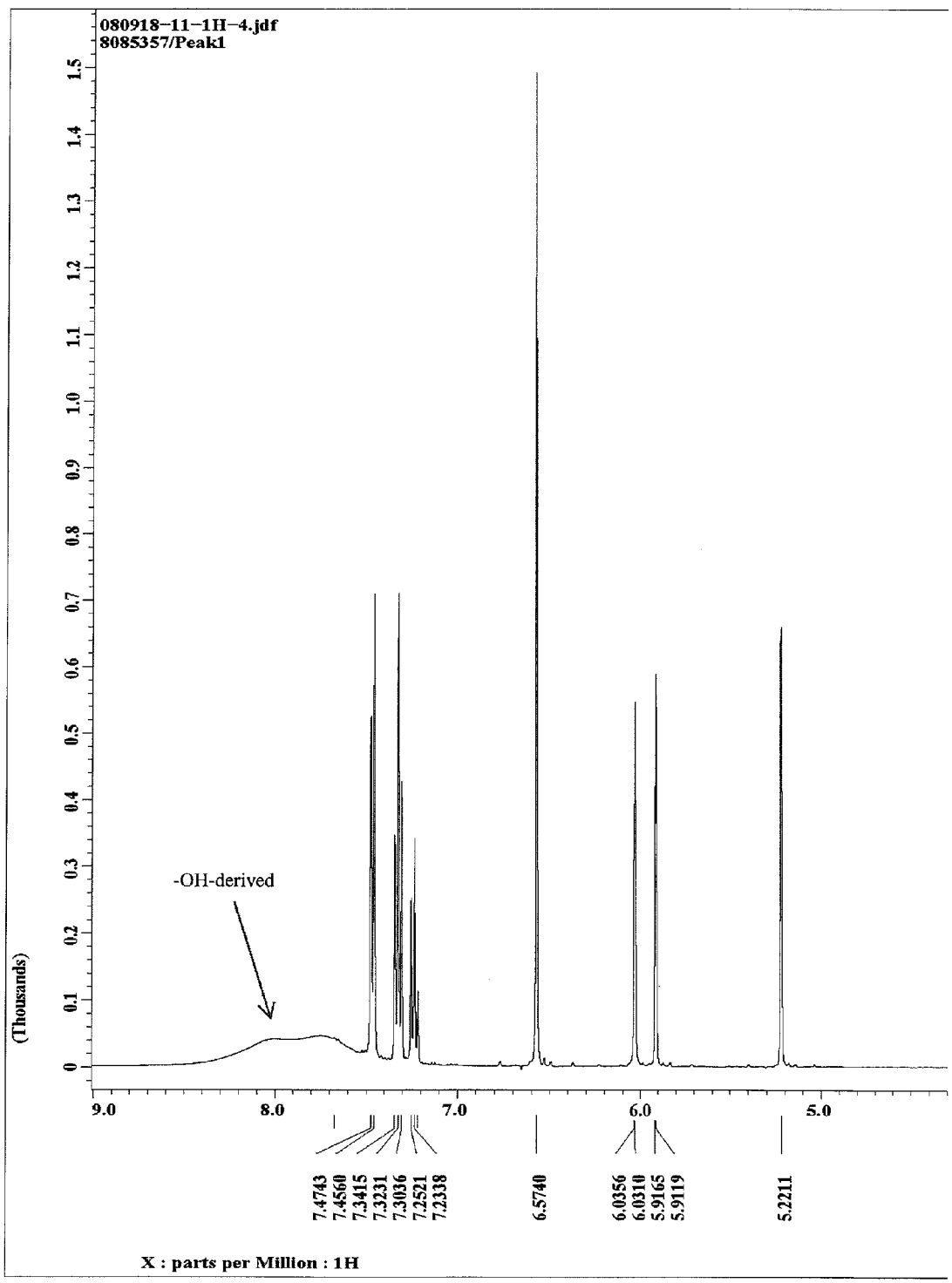
Figures 2, 4:
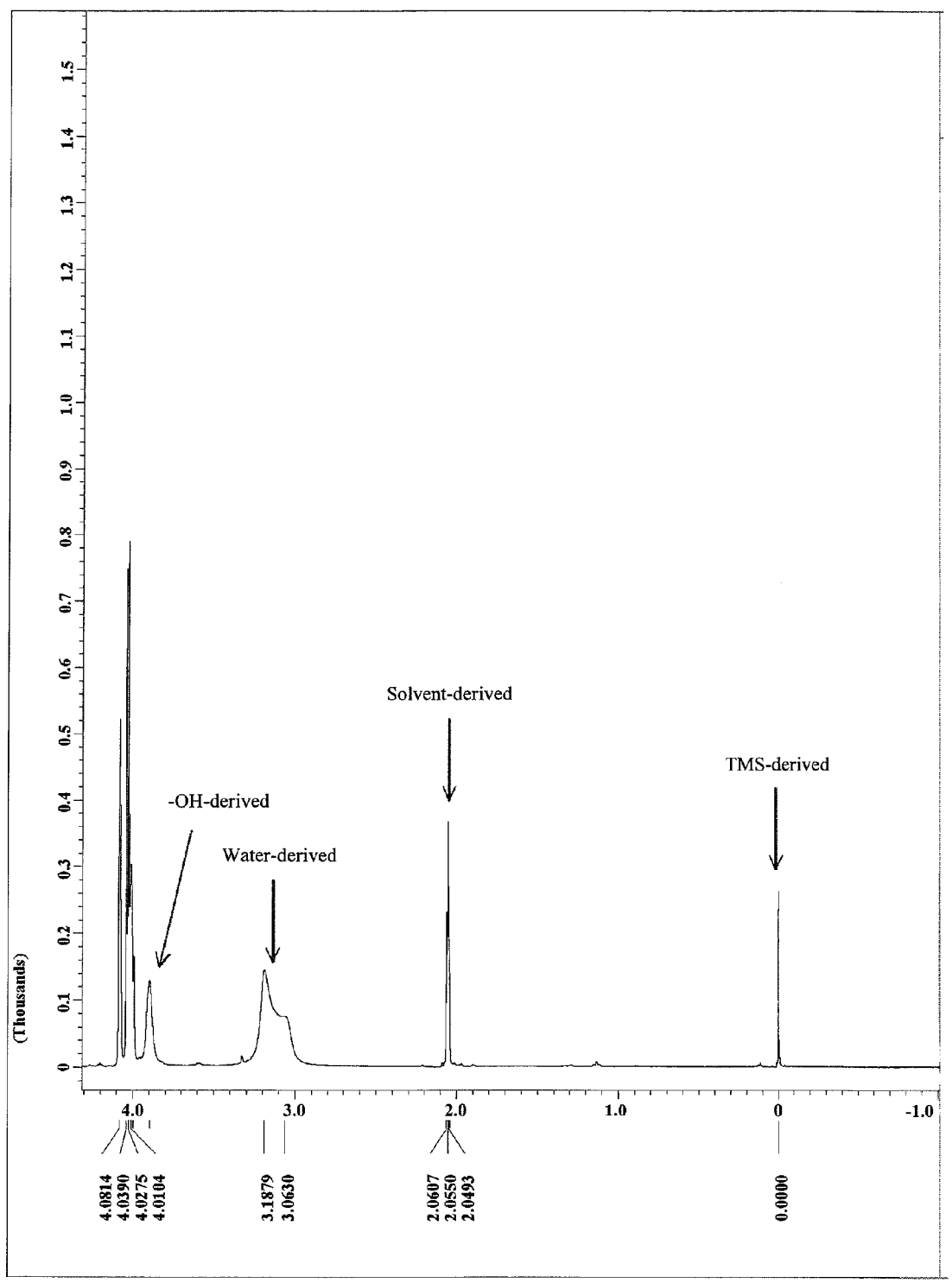
Figures 1, 5:
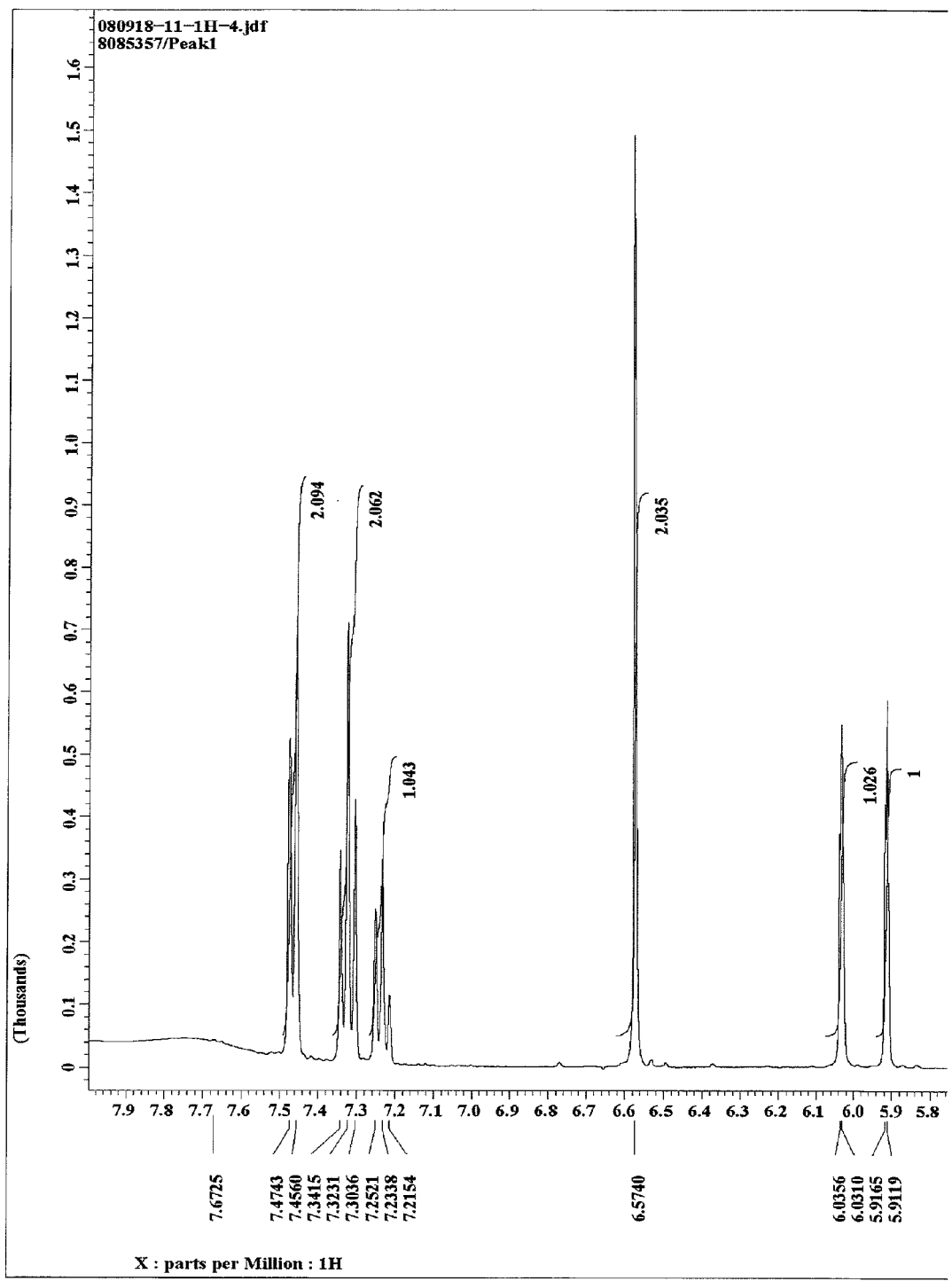
Figures 2, 5:
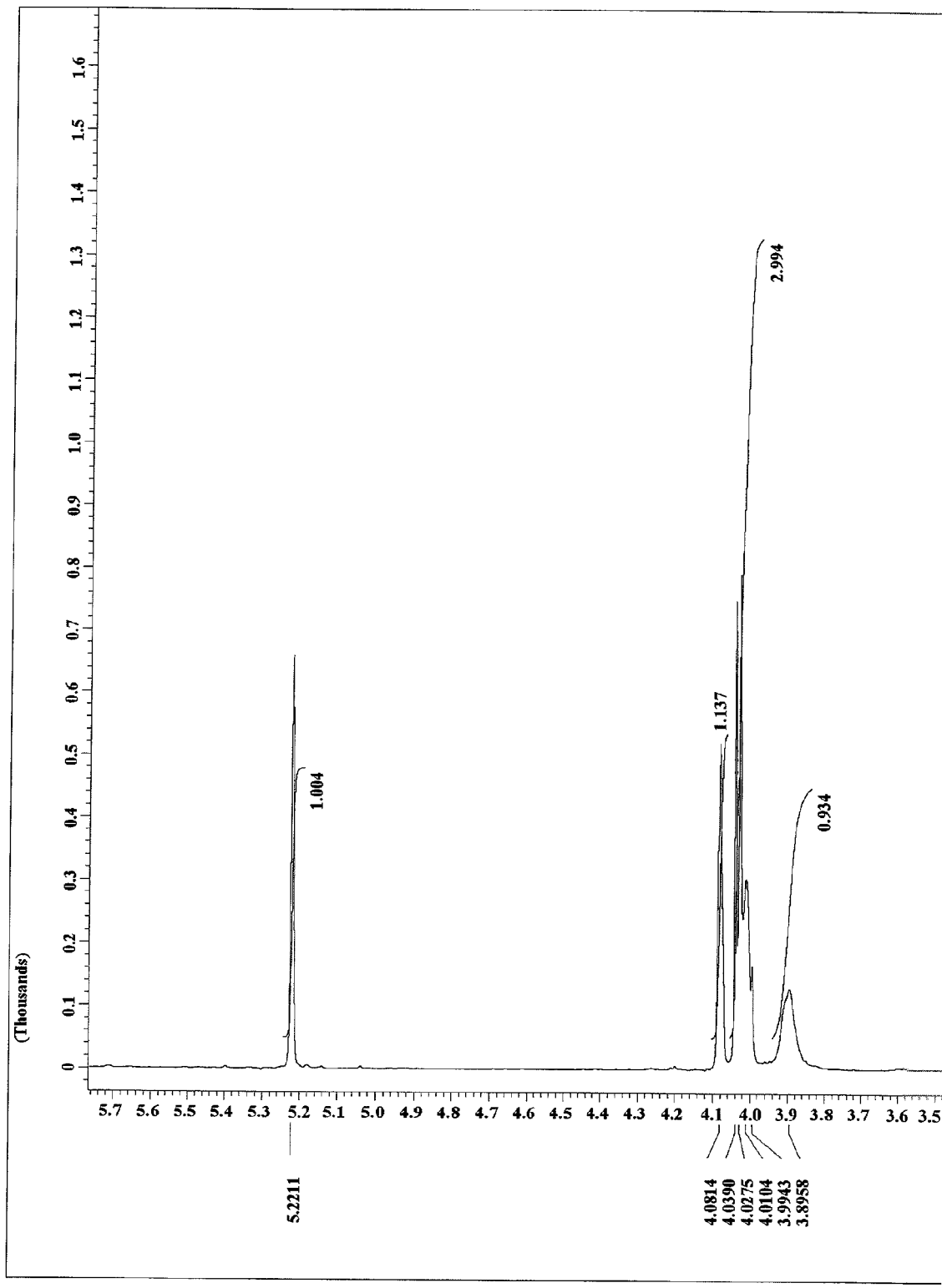
Figures 1, 6:
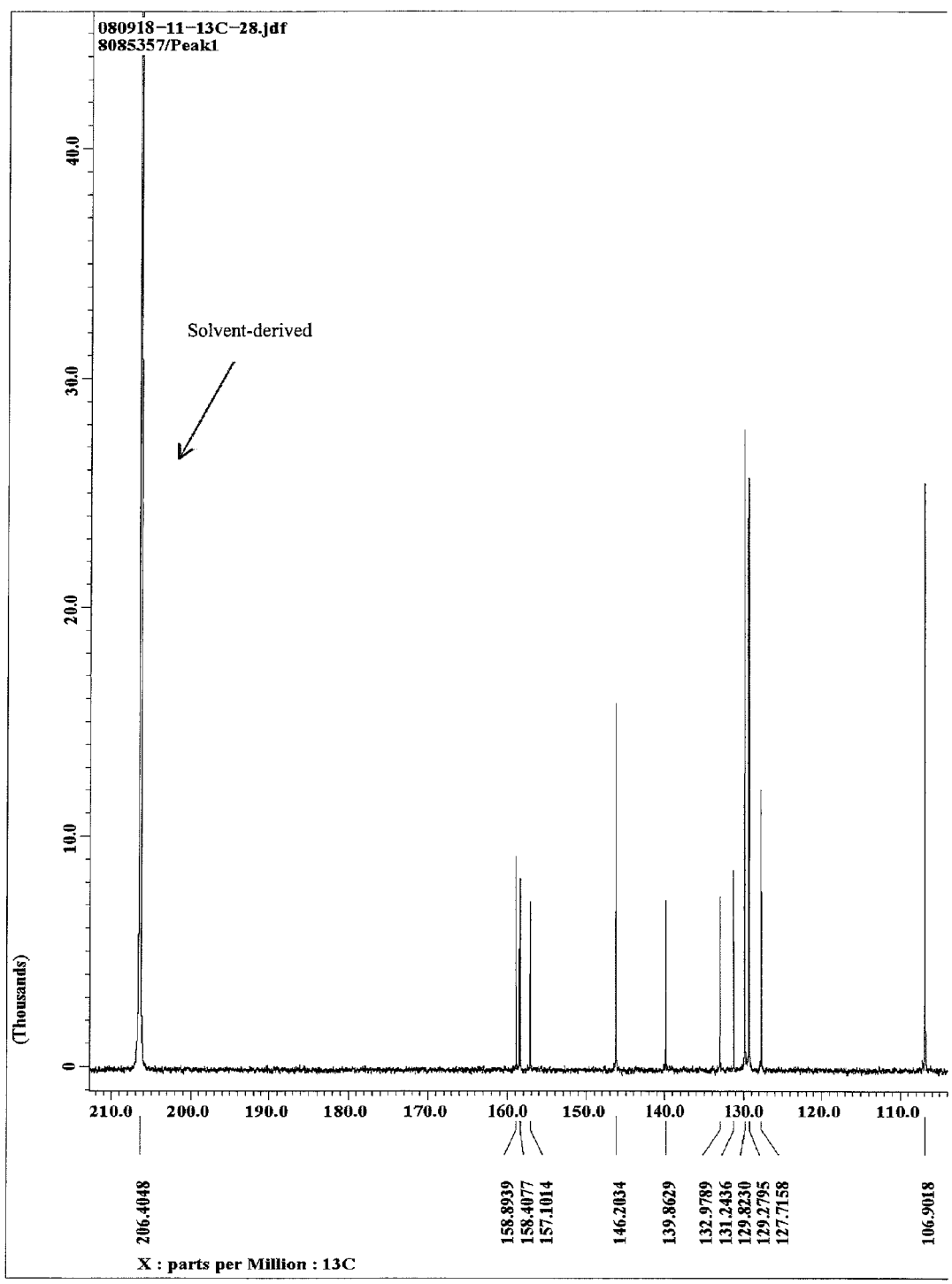
Figures 2, 6:
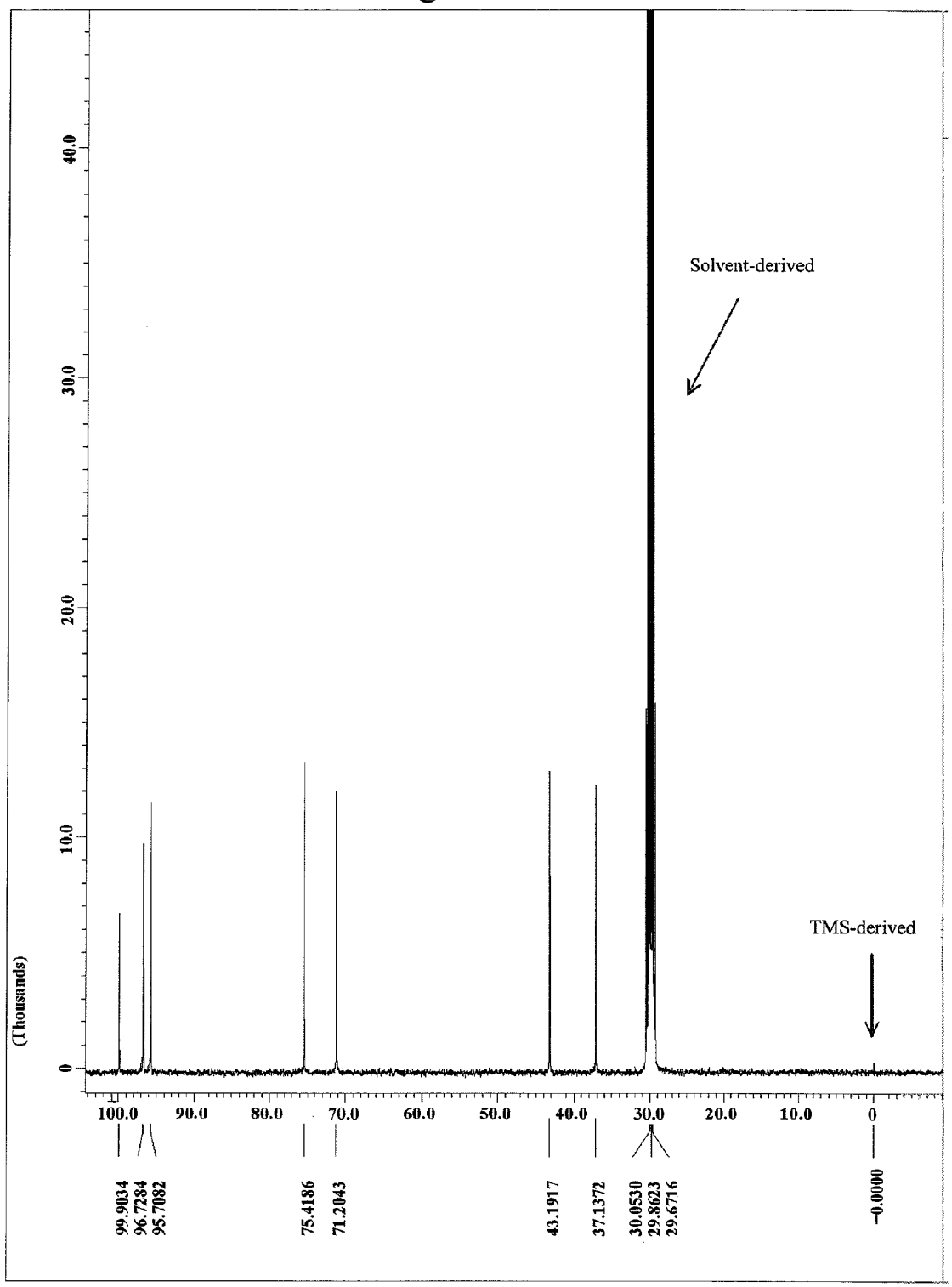
Figures 1, 7:
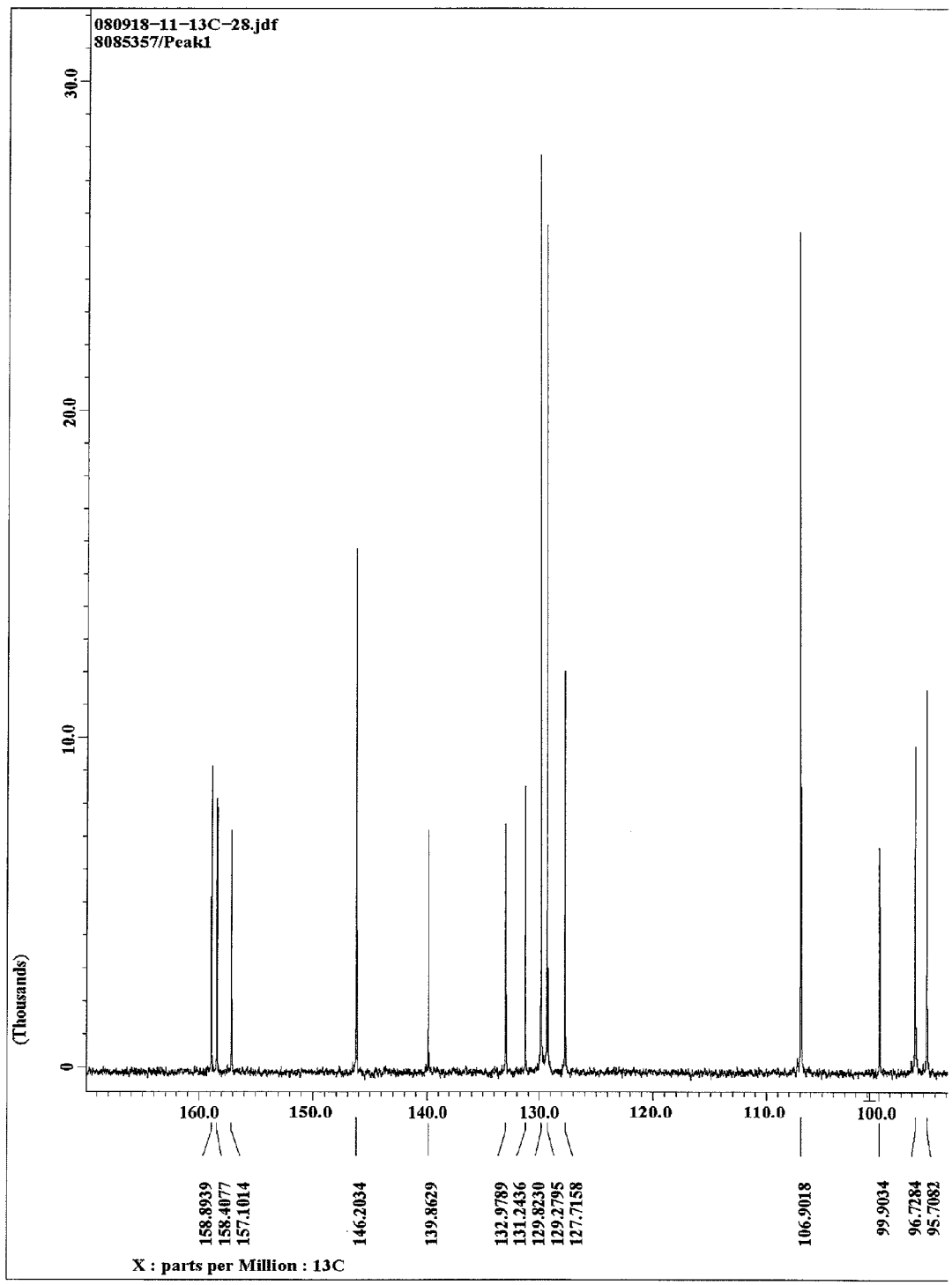
Figures 2, 7:
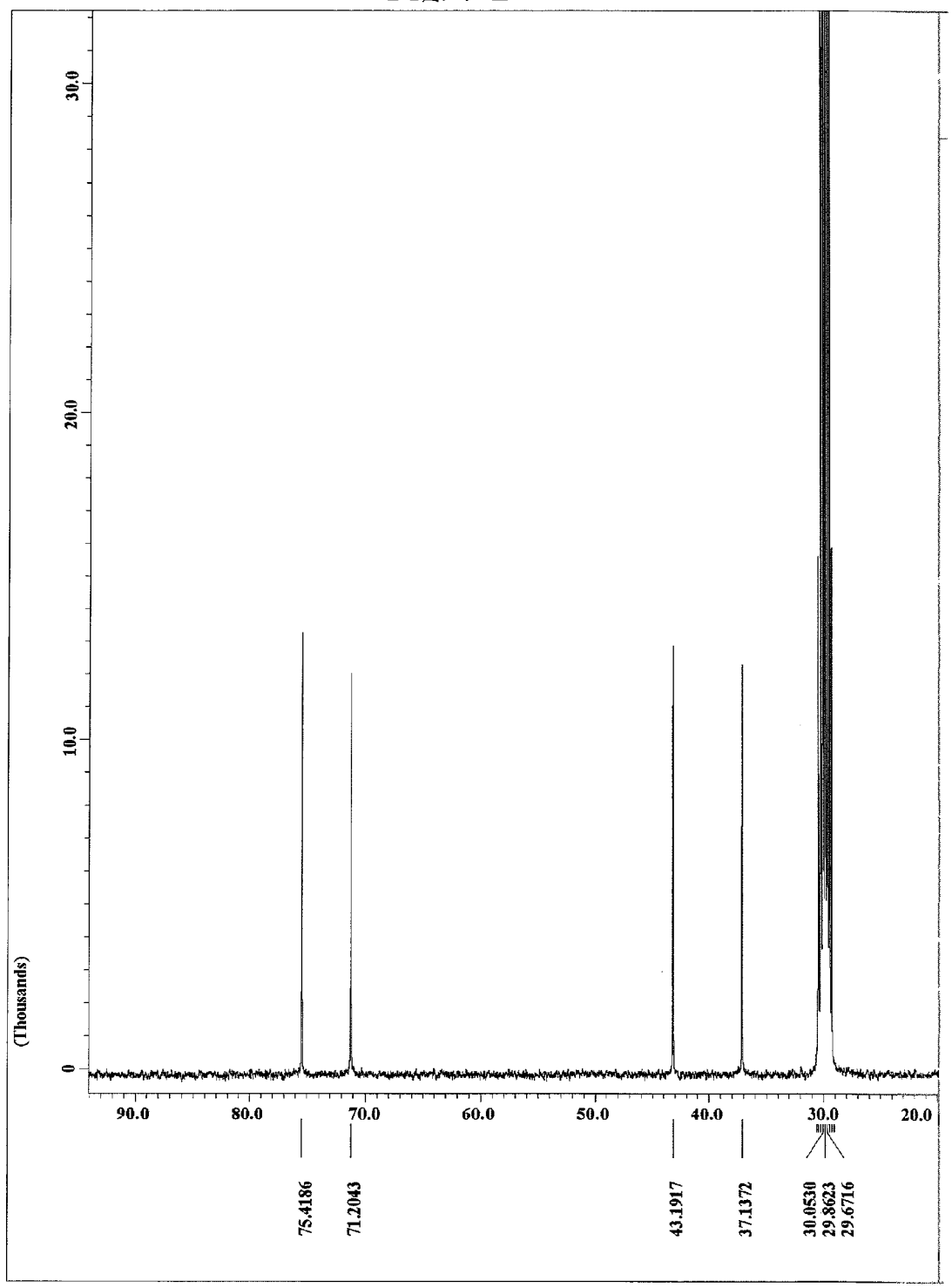

(2-4) Results of Analysis (i) FIG. 3 shows the ESI(+)-MS spectra of the thiol-degraded and purified NBP (peak 1), FIGS. 4-1 to 5-2 show the $^1$H NMR spectra, FIGS. 6-1 to 7-2 show the $^{13}$C NMR spectra, and Tables 7 to 9 and the putative structural formula 1 show the data.

TABLE 7

Results of ESI(+)-MS assay of the thiol-degraded and purified NBP (peak 1)

| Detected mass peak | Putative composition |
|---|---|
| m/z 429 [M + H]+ | $C_{22}H_{21}O_7S$ |
| m/z 451 [M + Na]+ | $C_{22}H_{20}O_7SNa$ |

TABLE 8

Results of $^1$H NMR assay of the thiol-degraded and purified NBP (peak 1)

| $^1$H | Chemical shift of $^1$H δ (ppm) | Number of protons |
|---|---|---|
| A | 3.994 to 4.039 | 3 |
| B | 4.081 | 1 |
| C | 5.221 | 1 |
| D | 5.914 | 1 |
| E | 6.033 | 1 |
| F | 6.574 | 2 |
| G | 7.234 | 1 |
| H | 7.323 | 2 |
| I | 7.465 | 2 |

TABLE 9

Results of $^{13}$C NMR assay of the thiol-degraded and purified NBP (peak 1)

| $^{13}$C | Chemical shift of $^{13}$C δc (ppm) |
|---|---|
| 1 | 37.14 |
| 2 | 43.19 |
| 3 | 71.20 |
| 4 | 75.42 |
| 5 | 95.71 |
| 6 | 96.73 |
| 7 | 99.90 |
| 8 | 106.90 |
| 9 | 127.72 |
| 10 | 129.28 |
| 11 | 129.82 |
| 12 | 131.24 |
| 13 | 132.98 |
| 14 | 139.86 |
| 15 | 146.20 |
| 16 | 157.10 |
| 17 | 158.41 |
| 18 | 158.89 |

[Chemical formula 7]

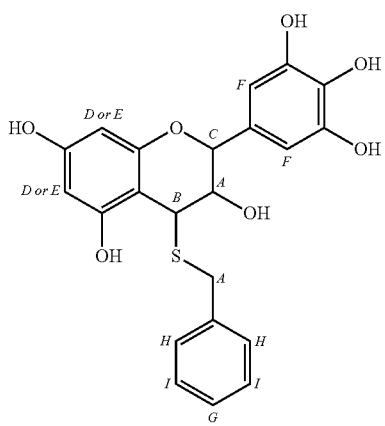

Putative structural formula 1: the thiol-degraded and purified NBP (peak 1)

Figure 8:
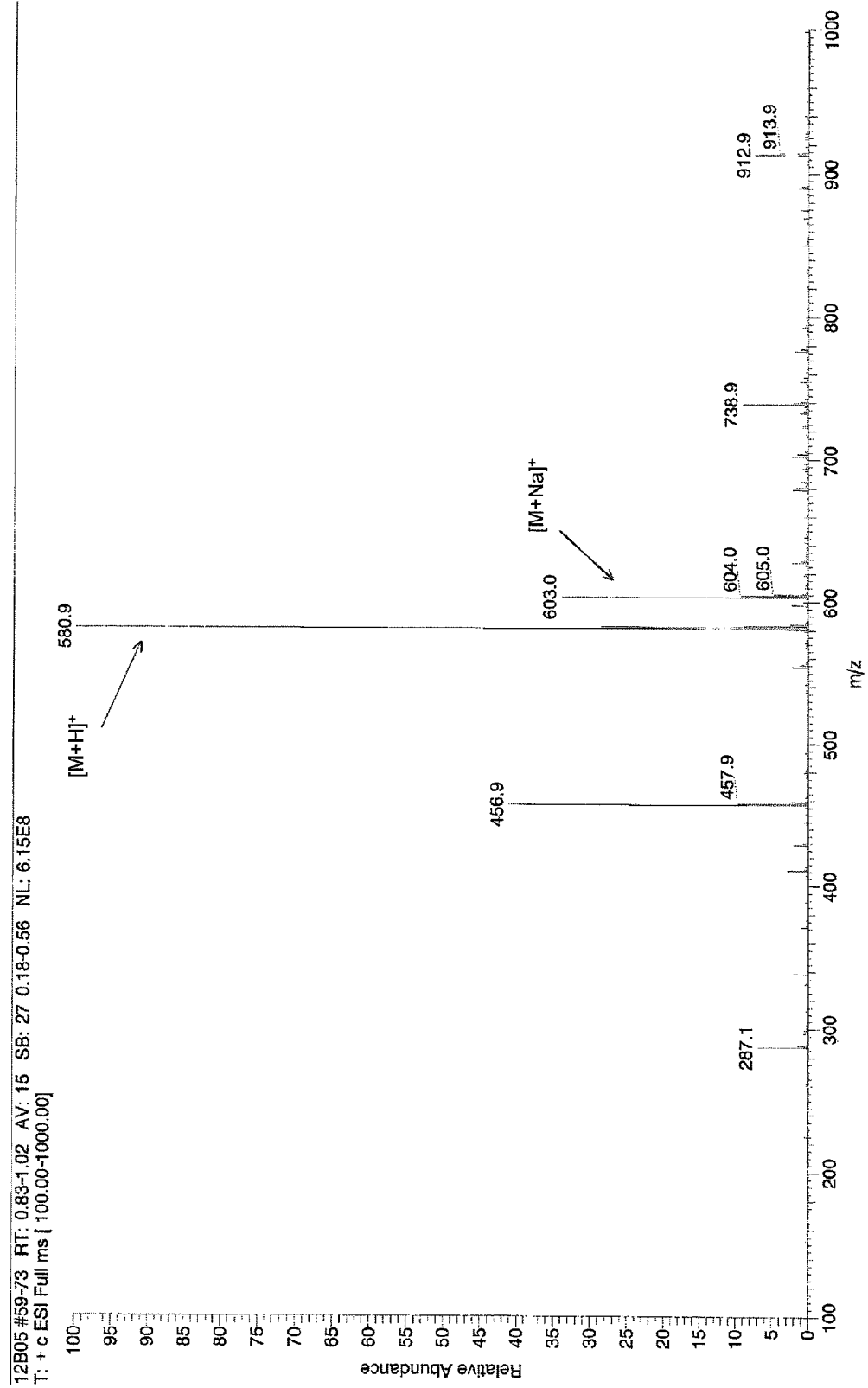
FIG. 8 shows the ESI(+)-MS spectra of the thiol-degraded and purified NBP (peak 2).
Figures 1, 9:
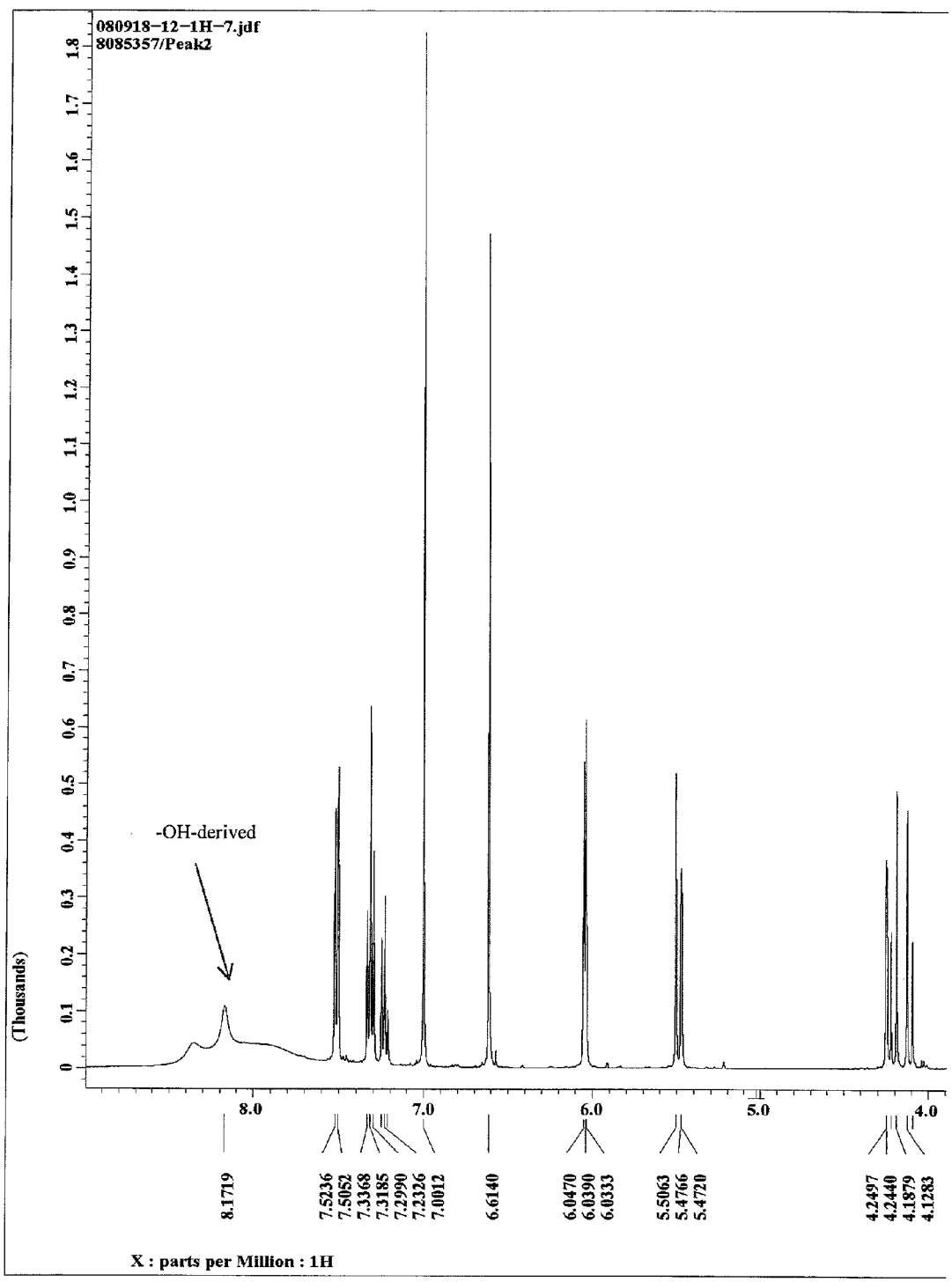
Figures 2, 9:
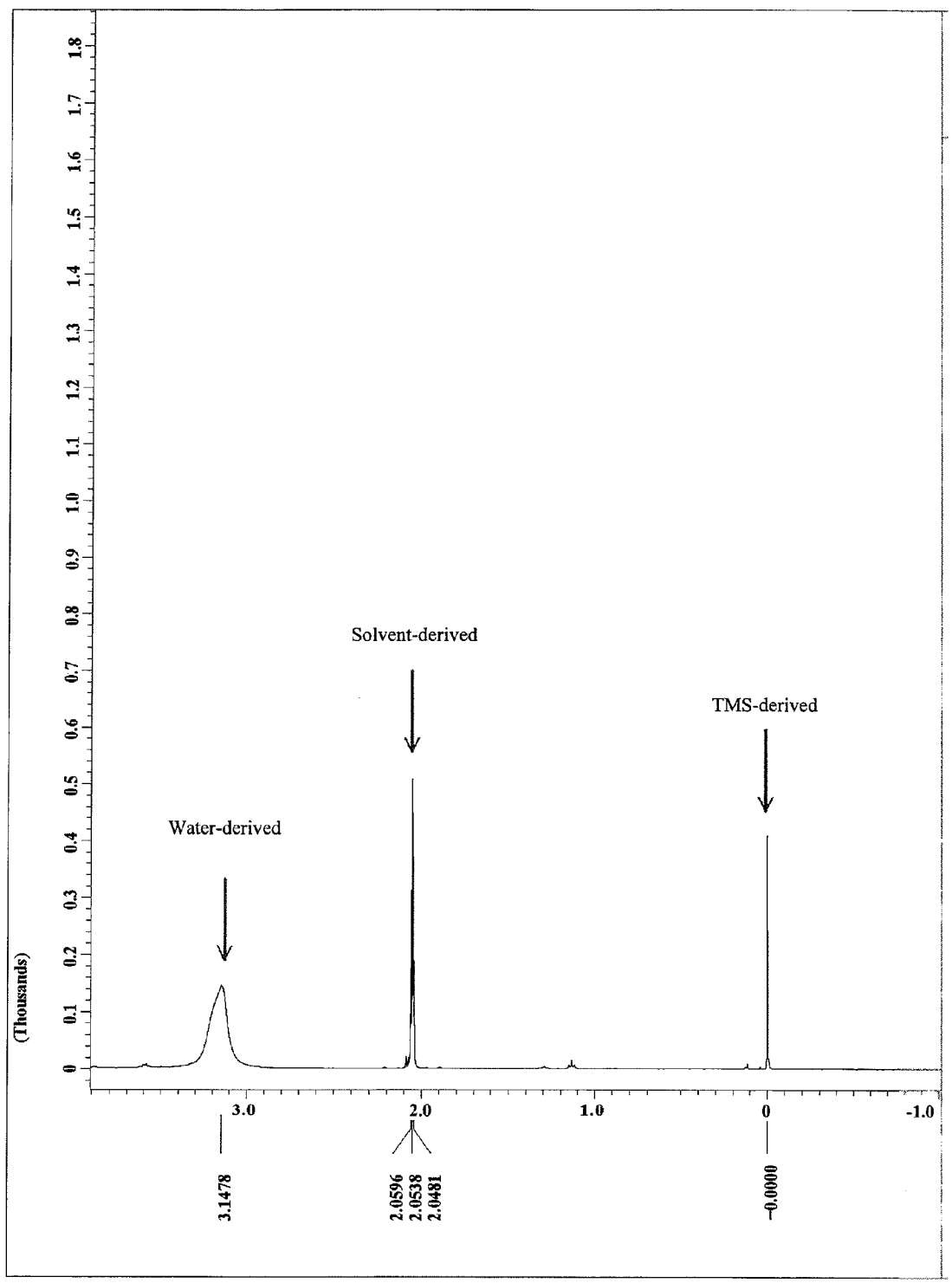
Figures 1, 10:
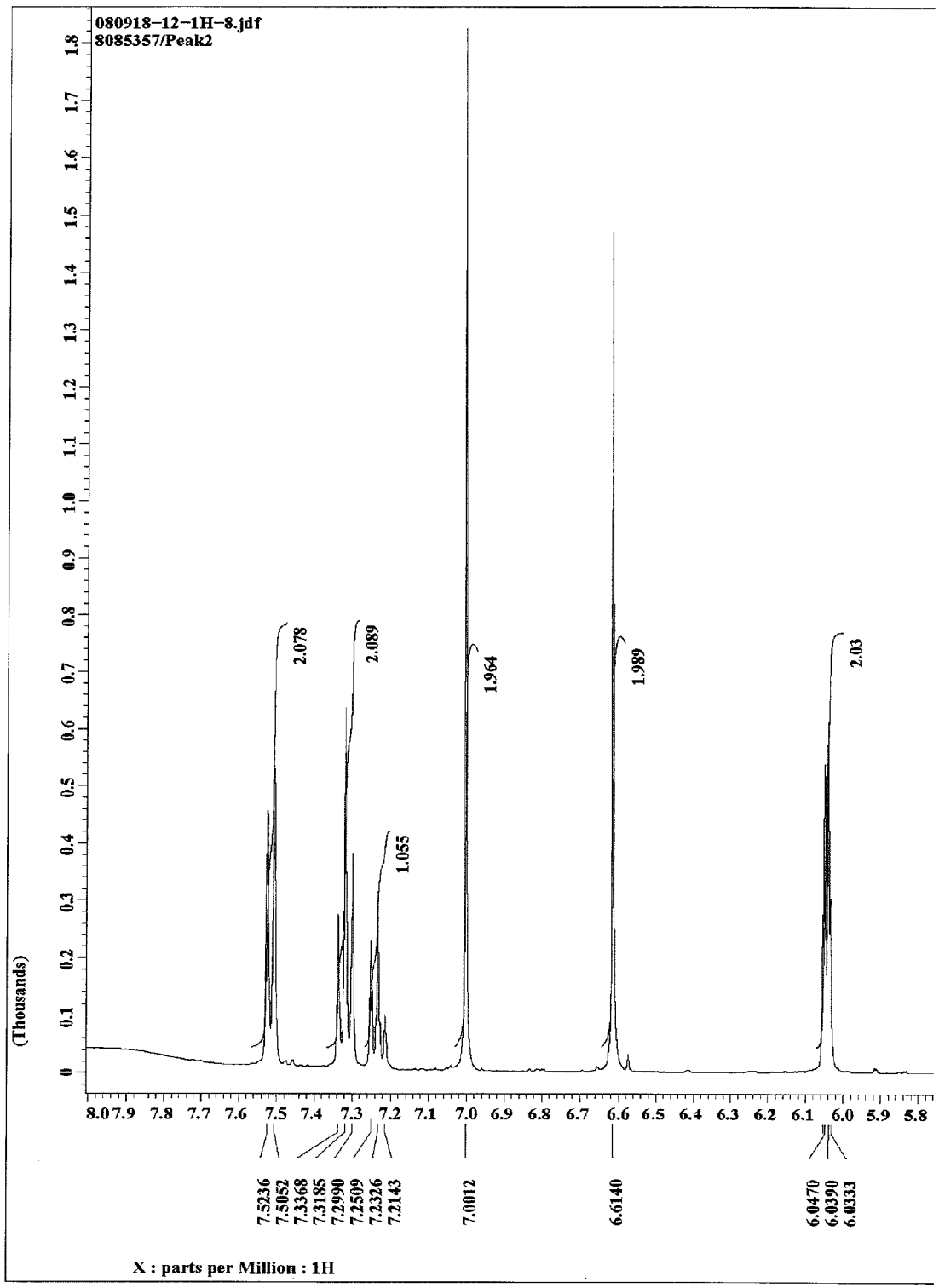
Figures 2, 10:
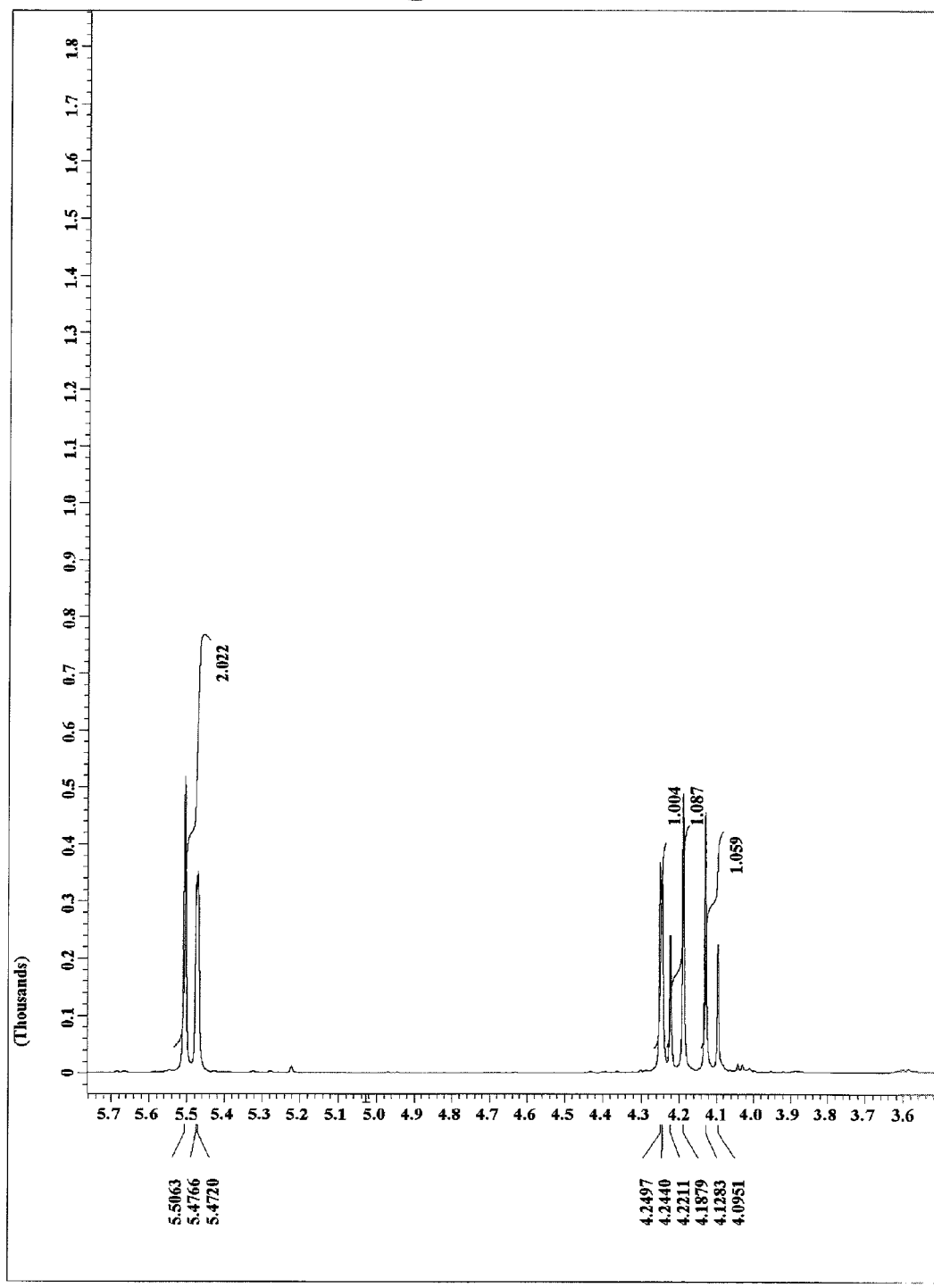
Figures 1, 11:
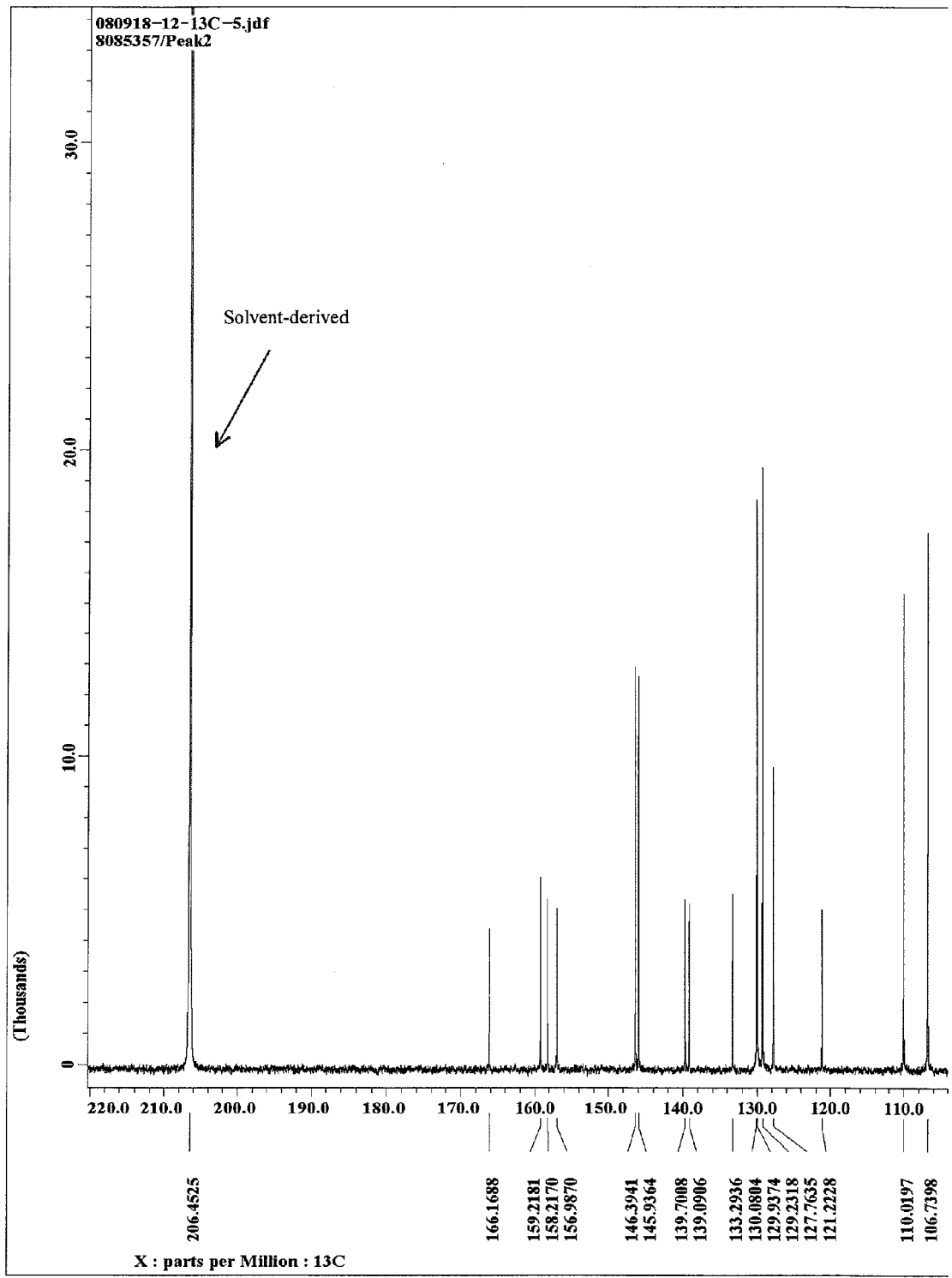
Figures 2, 11:
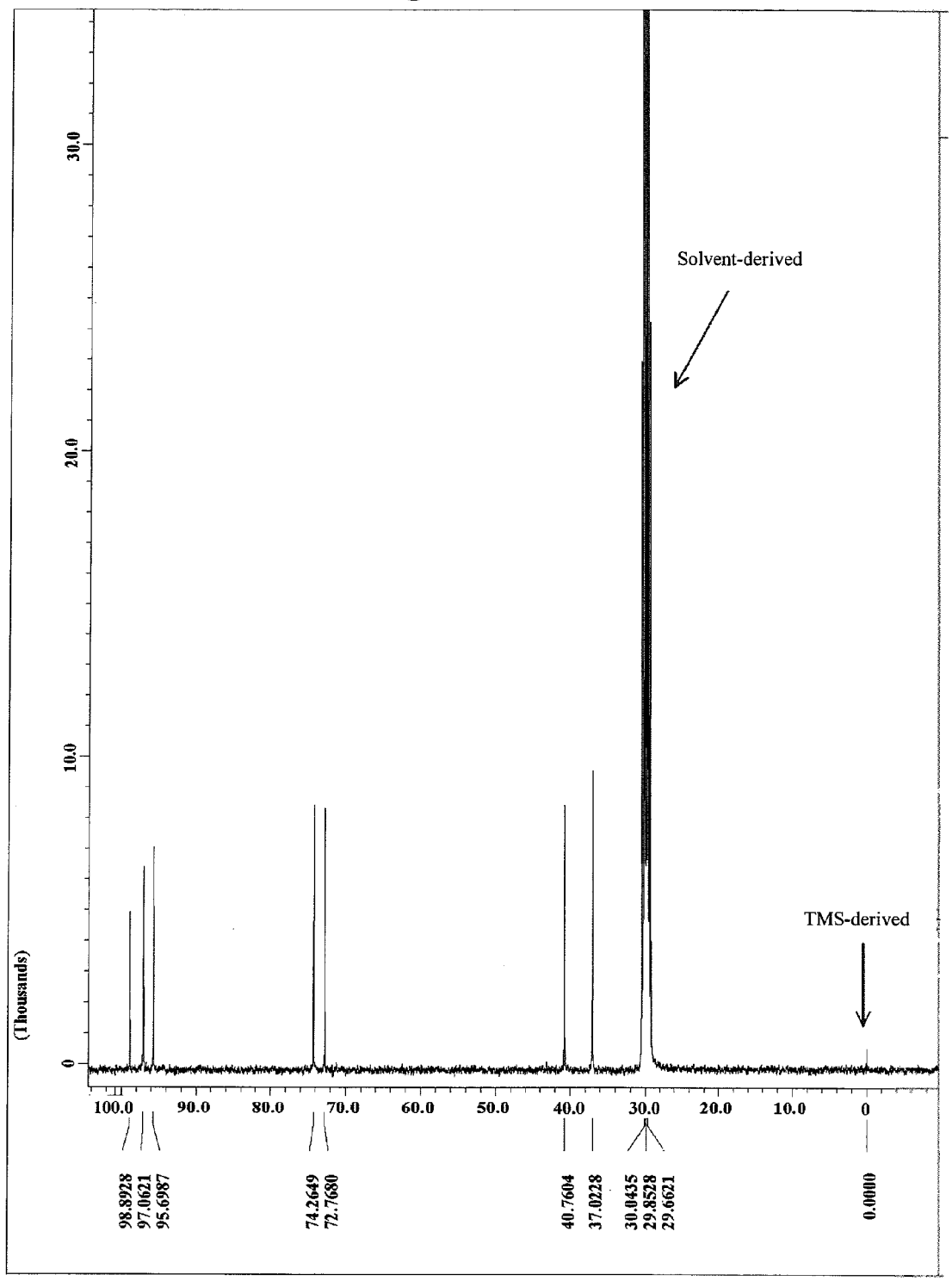
Figures 1, 12:
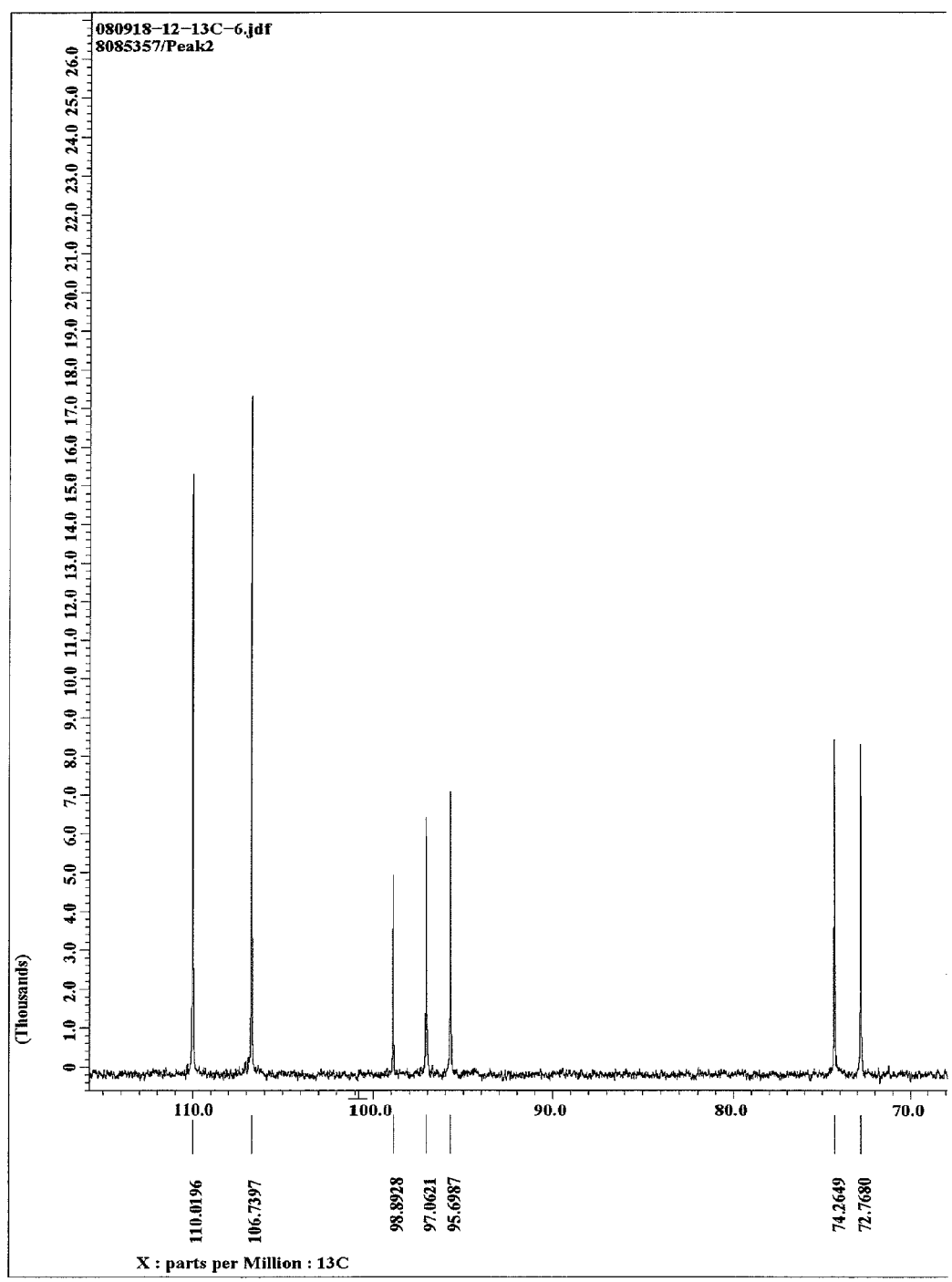
Figures 2, 12:
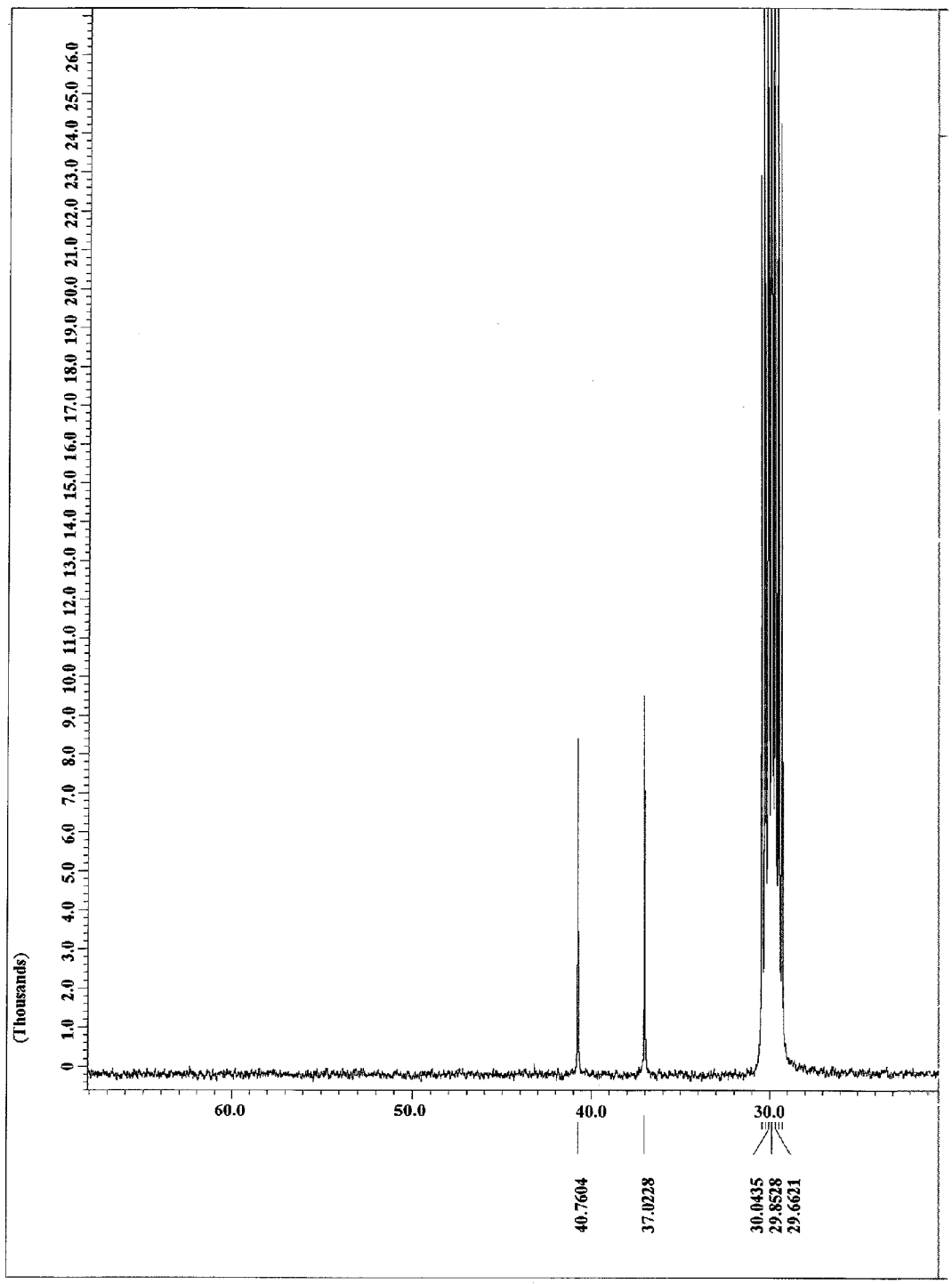
Figures 1, 13:
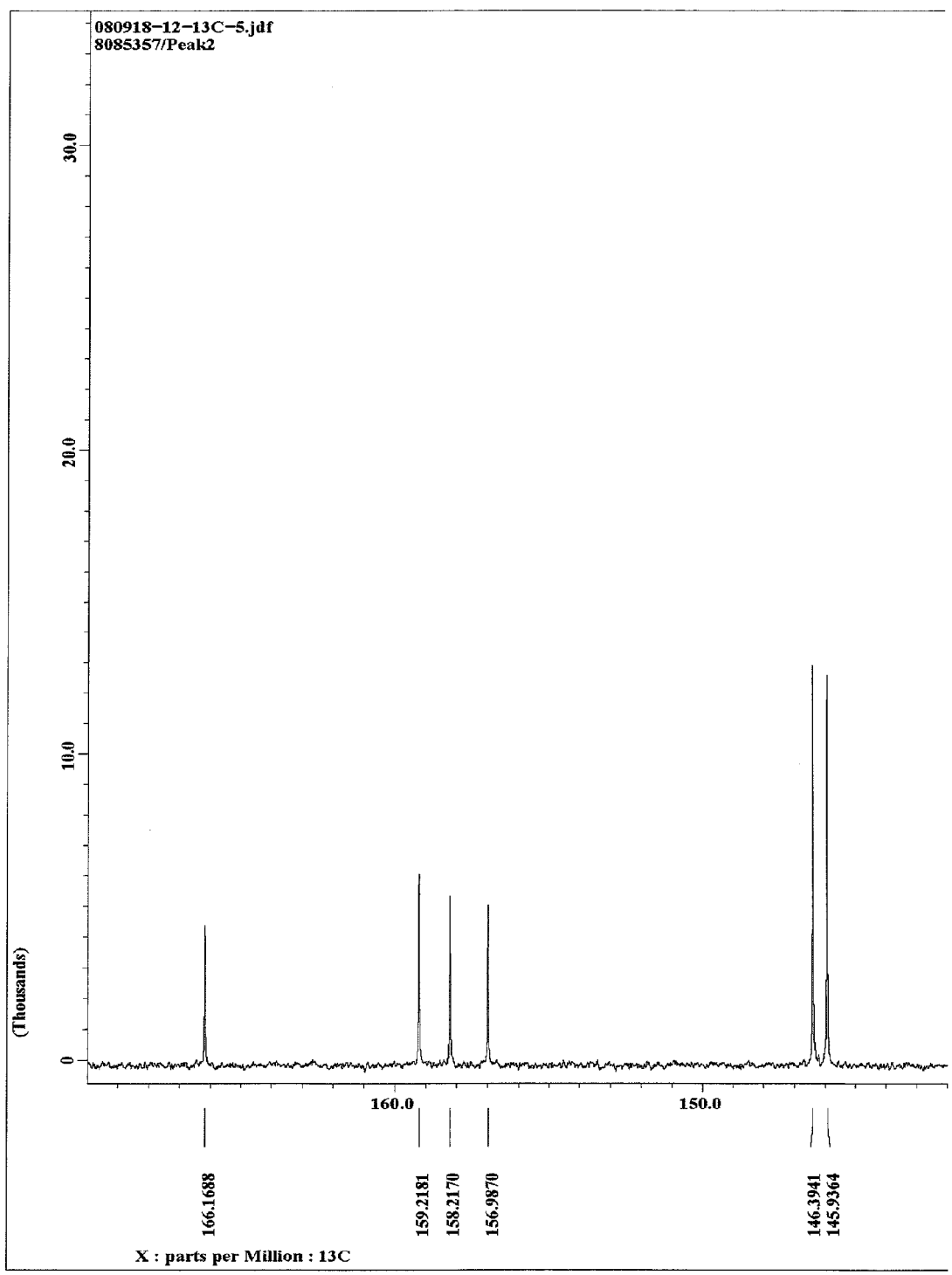
Figures 2, 13:
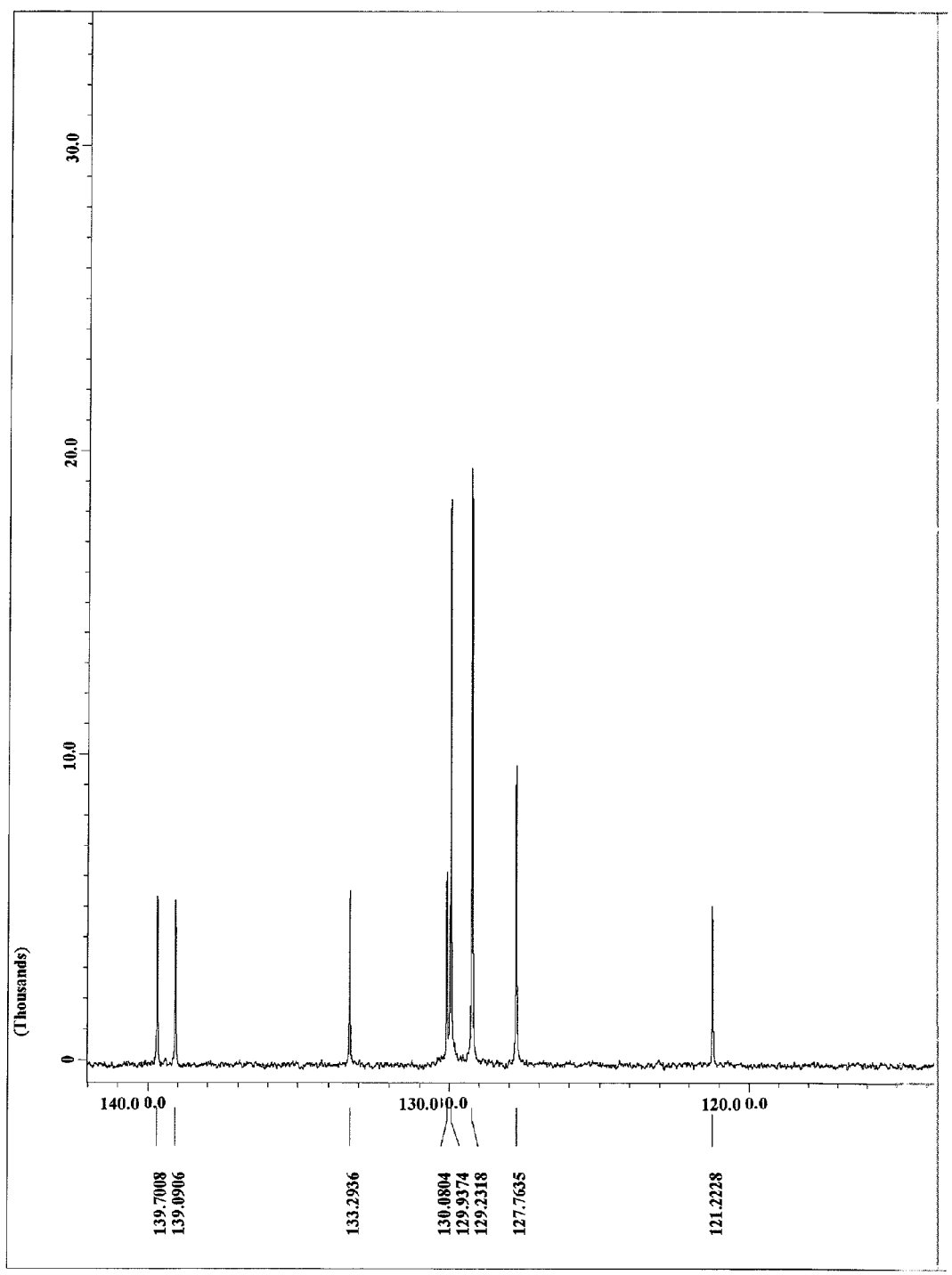
Figure 14:
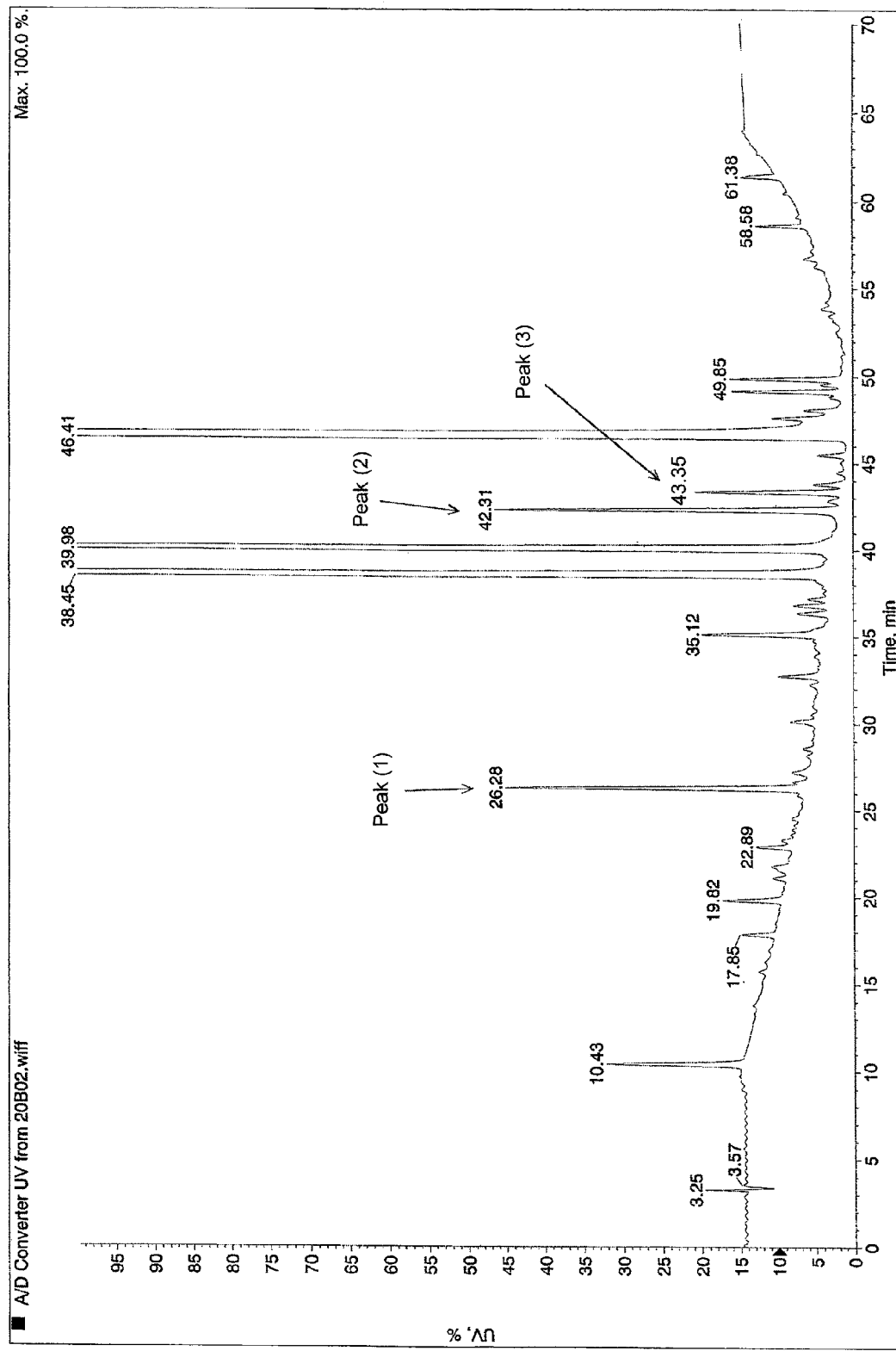
FIG. 14 shows the HPLC chromatogram of a solution of the thiol-degraded 10K NBP-A fraction.
Figure 15:
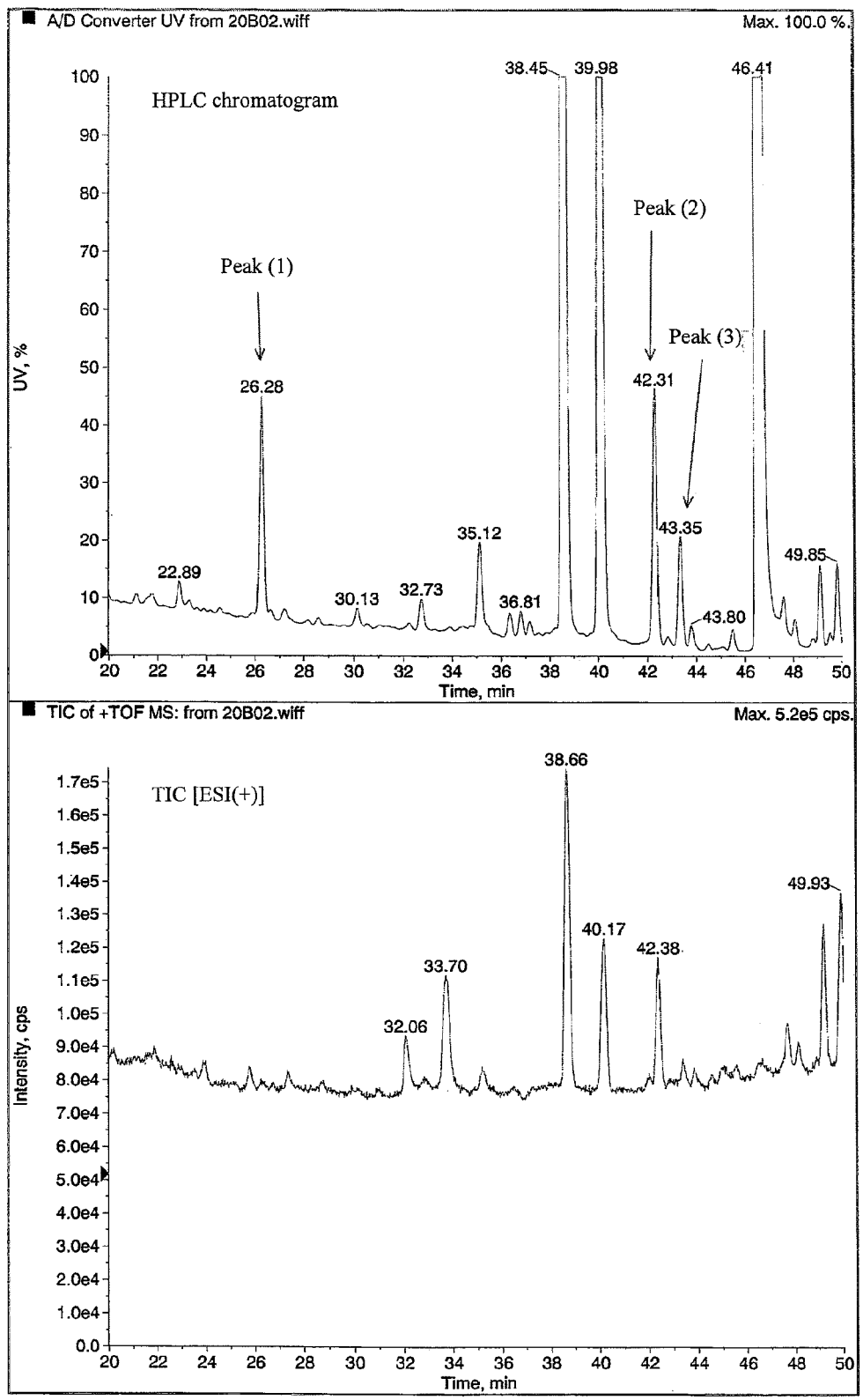
FIG. 15 shows the HPLC chromatogram and TIC [ESI(+)] of a solution of the thiol-degraded 10K NBP-A fraction.
Figures 1, 16:
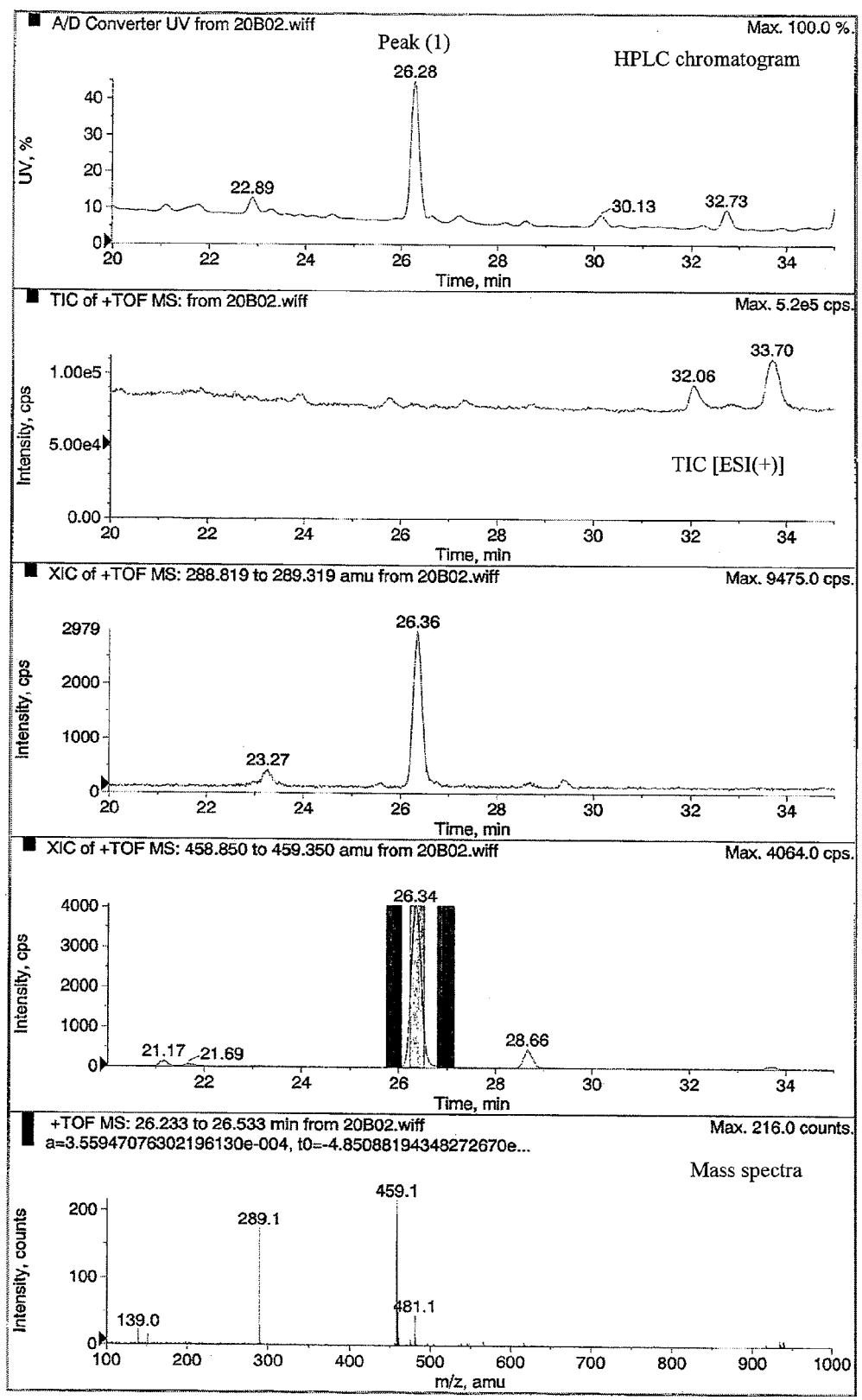
Figures 2, 16:
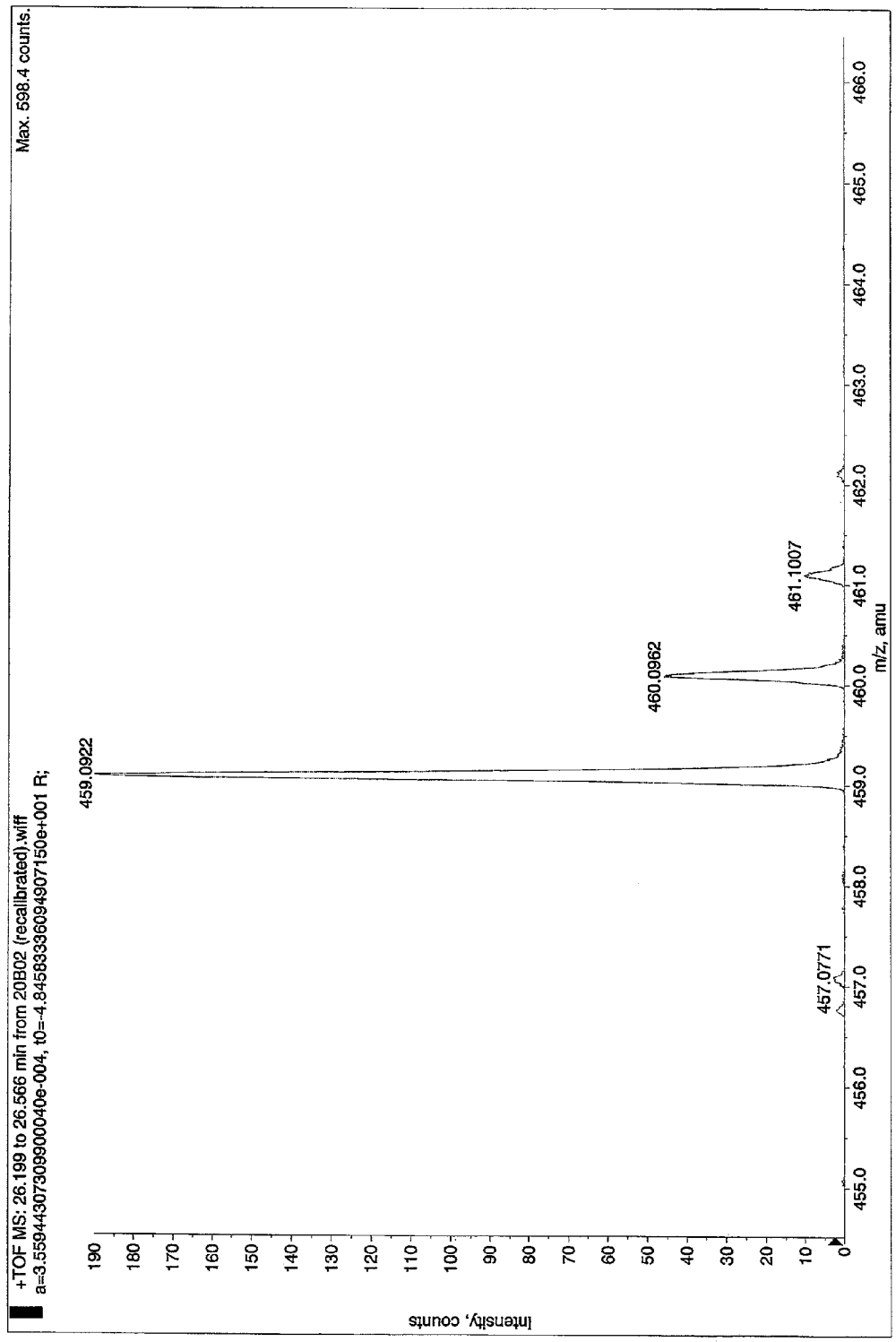
Figures 1, 17:
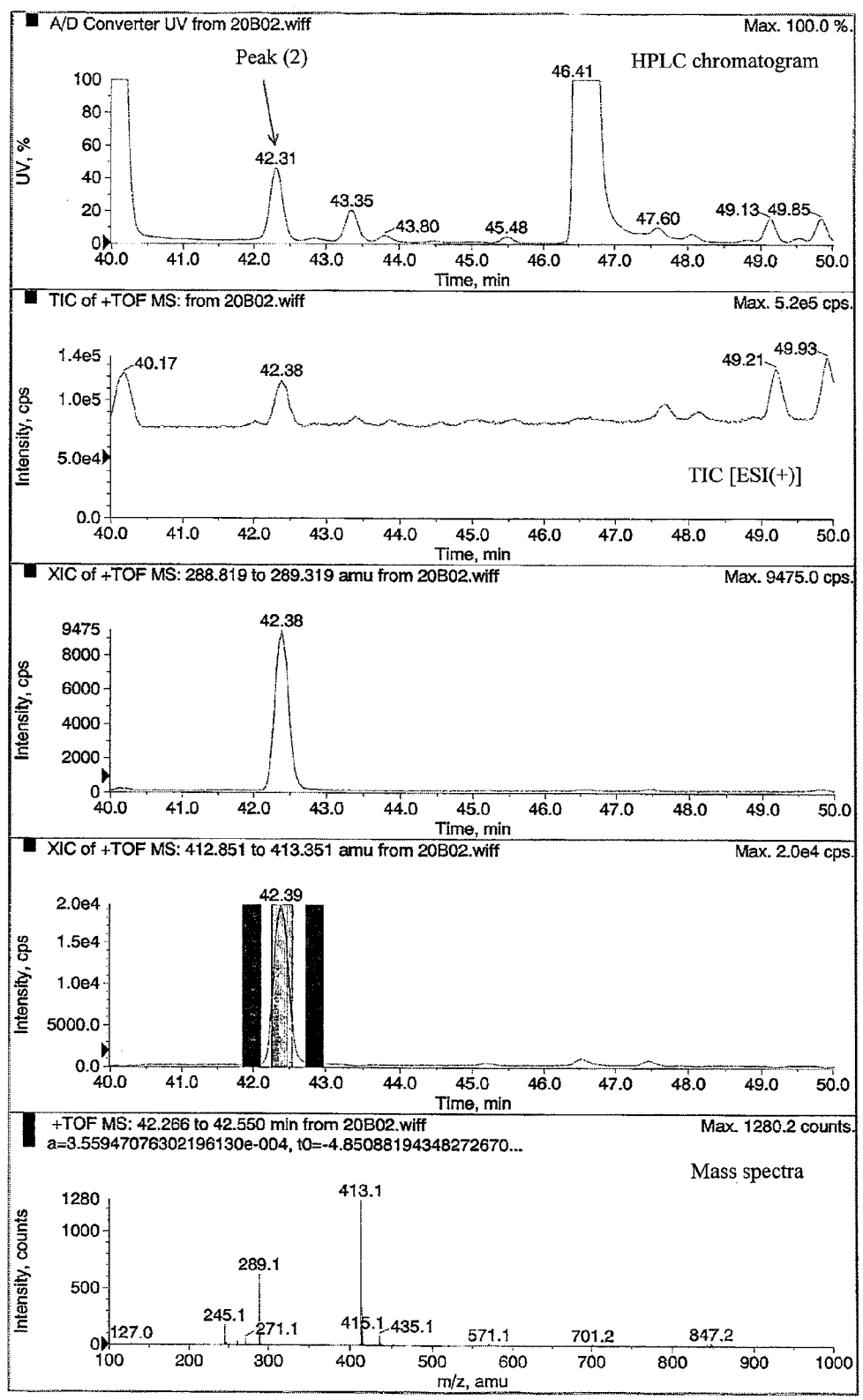
Figures 2, 17:
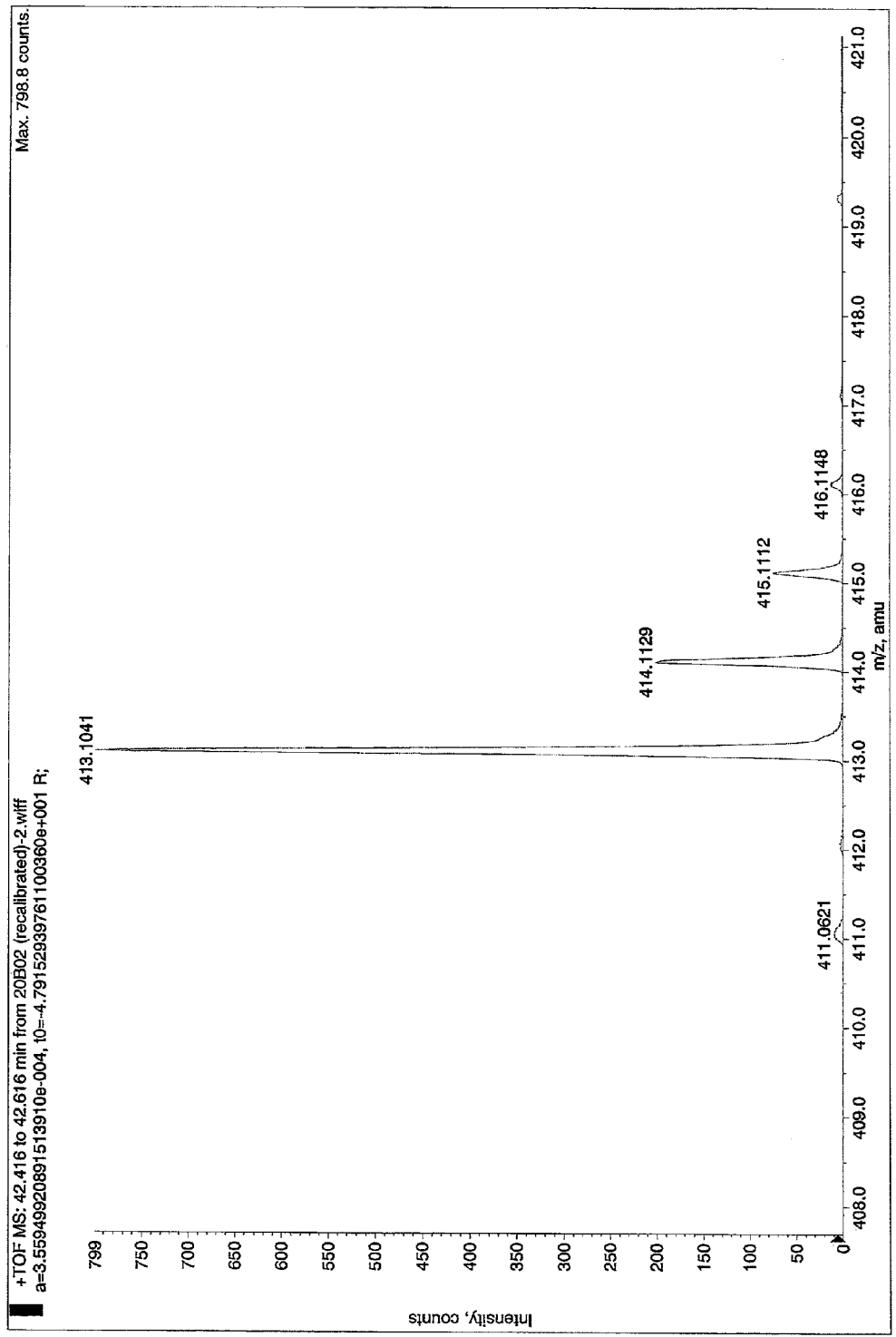
Figures 1, 18:
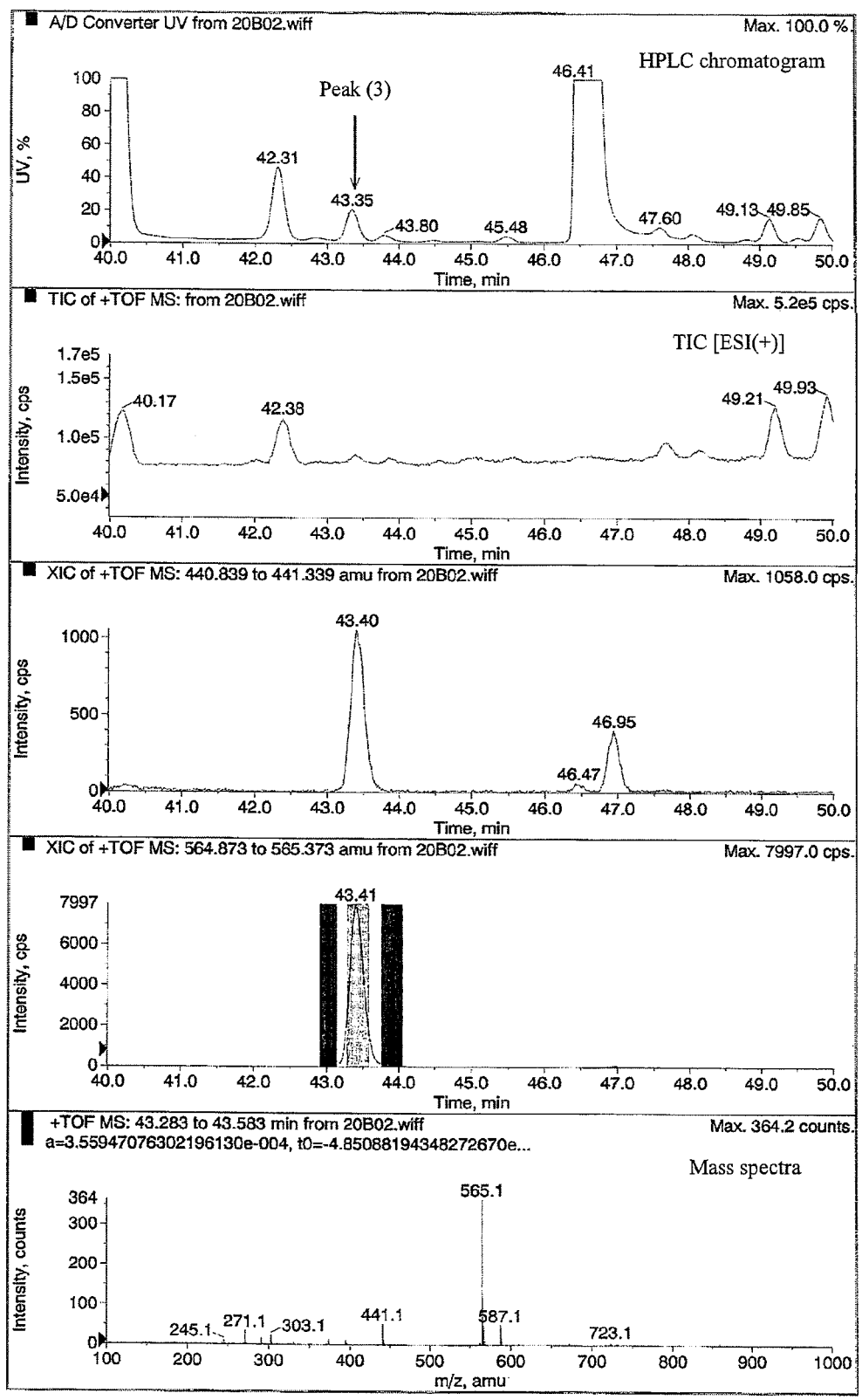
Figures 2, 18:
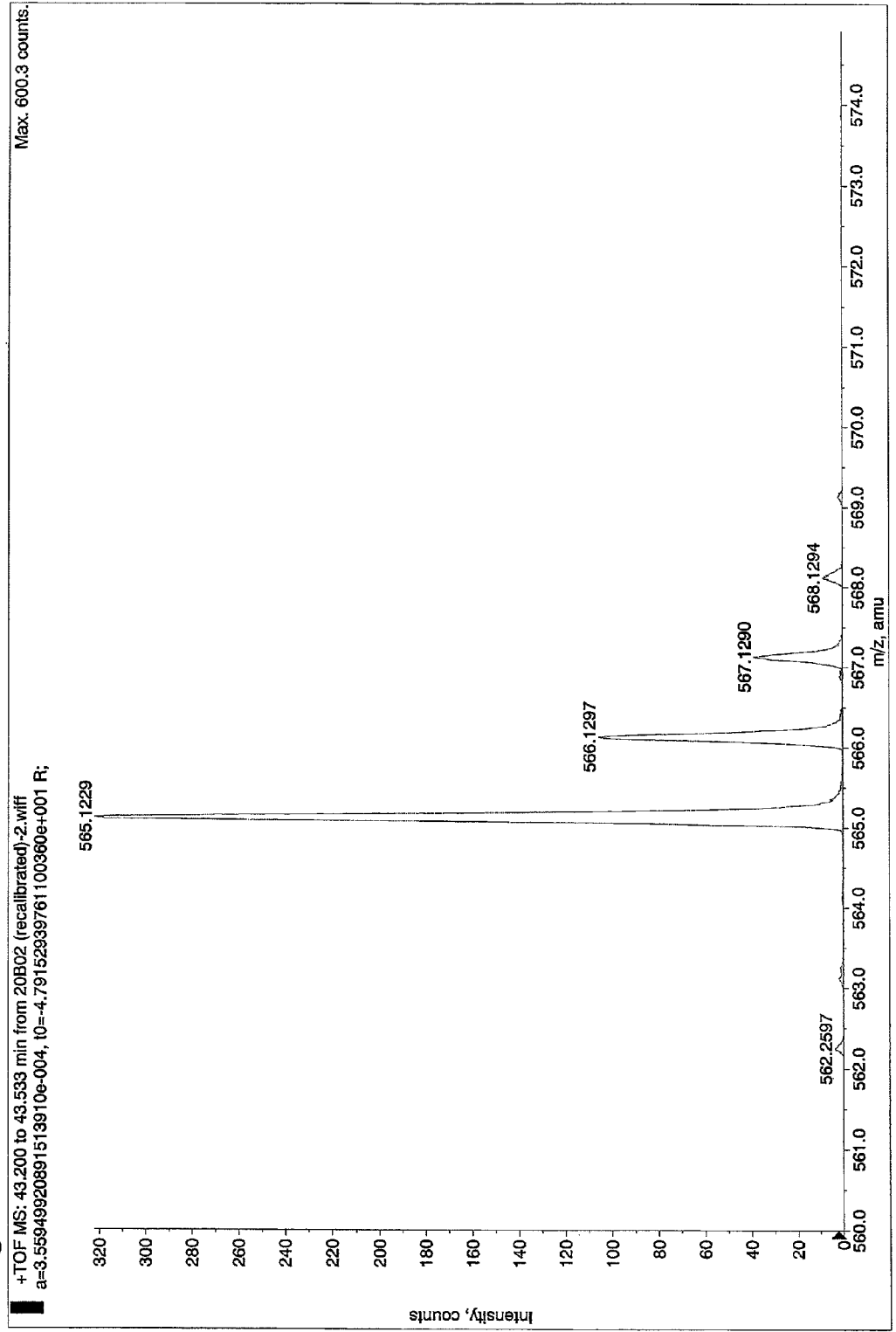

(ii) FIG. 8 shows the ESI(+)-MS spectra of the thiol-degraded and purified NBP (peak 2), FIGS. 9-1 to 10-2 show the $^1$H NMR spectra, FIGS. 11-1 to 13-2 show the $^{13}$C NMR spectra, and Tables 10 to 12 and the putative structural formula 2 show the data.

TABLE 10

Results of ESI(+)-MS assay of the thiol-degraded and purified NBP (peak 2)

| Detected mass peak | Putative composition |
|---|---|
| m/z 581 [M + H]+ | $C_{29}H_{25}O_{11}S$ |
| m/z 603 [M + Na]+ | $C_{29}H_{24}O_{11}SNa$ |

TABLE 11

Results of $^1$H NMR assay of the thiol-degraded and purified NBP (peak 2)

| $^1$H | Chemical shift of $^1$H δ (ppm) | Number of protons |
|---|---|---|
| A | 4.112 | 1 |
| B | 4.205 | 1 |
| C | 4.247 | 1 |
| D | 5.474 | 1 |
| E | 5.506 | 1 |
| F | 6.036 | 1 |
| G | 6.050 | 1 |
| H | 6.614 | 2 |
| I | 7.001 | 2 |
| J | 7.233 | 1 |
| K | 7.319 | 2 |
| L | 7.514 | 2 |

TABLE 12

Results of $^{13}$C NMR assay of the thiol-degraded and purified NBP (peak 2)

| $^{13}$C | Chemical shift of $^{13}$C δc (ppm) |
|---|---|
| 1 | 37.02 |
| 2 | 40.76 |
| 3 | 72.77 |
| 4 | 74.26 |
| 5 | 95.70 |
| 6 | 97.06 |
| 7 | 98.89 |
| 8 | 106.74 |
| 9 | 110.02 |
| 10 | 121.22 |
| 11 | 127.76 |
| 12 | 129.23 |
| 13 | 129.94 |
| 14 | 130.08 |
| 15 | 133.29 |
| 16 | 139.09 |
| 17 | 139.70 |
| 18 | 145.94 |
| 19 | 146.39 |
| 20 | 156.99 |
| 21 | 158.22 |
| 22 | 159.22 |
| 23 | 166.17 |

[Chemical formula 8]

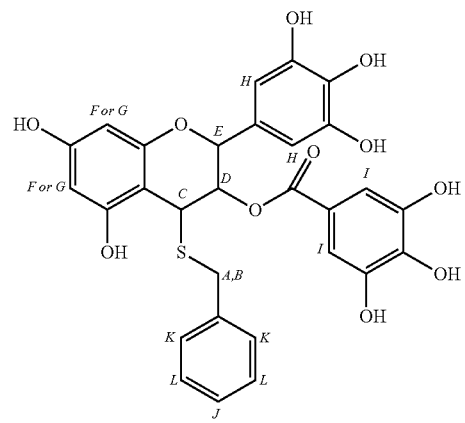

Putative structural formula 2: the thiol-degraded and purified NBP (peak 2)

(2-5) Analysis of Results (i) In the thiol-degraded and purified NBP (peak 1), pseudo-molecular ion peaks were observed at m/z 429 [(M+H)$^+$] and m/z 451 [(M+Na)$^+$] via ESI(+)-MS. Based on the data attained via ESI(+)-MS, $^1$H NMR, and $^{13}$C NMR, a molecular composition was deduced to be C$_{22}$H$_{20}$O$_7$S (Table 7). The analysis of the $^1$H NMR spectra revealed the existence of 9 aromatic protons (δ 5.914 (1H), 6.033 (1H), 6.574 (2H), 7.234 (1H), 7.323 (2H), and 7.465 (2H)) and 5 non-aromatic protons (δ 3.994 to 4.039 (3H), 4.081 (1H), and 5.221 (1H)) (Table 8). Among the 9 aromatic protons, 5 protons were found to be benzyl protons (δ 7.234 (1H), 7.323 (2H), and 7.465 (2H)). The analysis of the $^{13}$C NMR spectra revealed the existence of 14 types of aromatic carbons (δ$_c$ 95.71, 96.73, 99.90, 106.90, 127.72, 129.28, 129.82, 131.24, 132.98, 139.86, 146.20, 157.10, 158.41, and 158.89, deduced to contain 18 carbons) and 4 types of non-aromatic carbons (δ$_c$ 37.14, 43.19, 71.20, and 75.42) (Table 9). As a result of thorough analysis of the above data, the planar structure of the thiol-degraded and purified NBP (peak 1) was deduced as shown in the putative structural formula 1. Specifically, the peak 1 component was deduced to be a benzyl thioether derivative of (epi)gallocatechin. Hereafter, it may be occasionally referred to as an "(epi)gallocatechin benzyl thioether derivative" or an "(epi)gallocatechin derivative."

(ii) In the thiol-degraded and purified NBP (peak 2), pseudo-molecular ion peaks were observed at m/z 581 [(M+H)$^+$] and m/z 603 [(M+Na)$^+$] via ESI(+)-MS. Based on the data attained via ESI(+)-MS, $^1$H NMR, and $^{13}$C NMR, a molecular composition was deduced to be C$_{29}$H$_{25}$O$_{11}$S (Table 10). A comparison thereof with the thiol-degraded and purified NBP (peak 1) demonstrates that the NMR spectra thereof are similar to each other. The analysis of the $^1$H NMR spectra revealed the existence of 11 aromatic protons (δ 6.036 (1H), 6.050 (1H), 6.614 (2H), 7.001 (2H), 7.233 (1H), 7.319 (2H), and 7.514 (2H)) and 5 non-aromatic protons (δ 4.112 (1H), 4.205 (1H), 4.247 (1H), 5.474 (1H), and 5.506 (1H)) (Table 11). Further, the analysis of the $^{13}$C NMR spectra revealed the existence of 18 types of aromatic carbons (δ$_c$ 95.70, 97.06, 98.89, 106.74, 110.02, 121.22, 127.76, 129.23, 129.94, 130.08, 133.29, 139.09, 139.70, 145.94, 146.39, 156.99, 158.22, and 159.22, deduced to contain 24 carbons) and 5 types of non-aromatic carbons (δ$_c$ 37.02, 40.76, 72.77, 74.26, and 166.17) (Table 12). As a result of thorough analysis of the above data, the planar structure of the thiol-degraded and purified NBP (peak 2) was deduced as shown in the putative structural formula 2. Specifically, the peak 2 component was deduced to be a benzyl thioether derivative of (epi) gallocatechin gallate. Hereafter, it may be occasionally referred to as an "(epi)gallocatechin gallate benzyl thioether derivative" or an "(epi)gallocatechin gallate derivative."

(3) Structural Analysis of Other Constituents of NBP

As described in (1) above, it was deduced that thiol-degraded NBP comprised 3 components; epigallocatechin gallate, a benzyl thioether derivative of epicatechin, and a benzyl thioether derivative of epicatechin gallate, in addition to two major components (i.e., peak 1 component and peak 2 component) based on a comparison of the results of HPLC analysis of thiol-degraded NBP and those of HPLC analysis of reagents, thiol-degraded procyanidin C1 (an epicatechin trimer), and thiol-degraded grape seed-derived procyanidin composed of epicatechin and epicatechin gallate (Gravinol®, Kikkoman).

A 10 K fraction of NBP-A prepared in Example 3 was degraded by the thiol degradation technique conducted in (1) above, the solution was designated as an analysis sample, and the following analysis was carried out.

(3-1) Objectives

To obtain the mass spectra of the analysis sample via LC-MS assay and confirm the molecular weight thereof (3-2) Analysis Sample A solution of the 10K NBP-A fraction degraded with thiol (3-3) Analysis Item Mass spectrometry (LC-MS)

(3-4) Analysis Method

Assay was carried out under the LC-MS conditions below.

TABLE 13

| Apparatuses used: | Agilent LC1100 System, LC Agilent Technologies QSTAR XL, MS Applied Biosystems |
|---|---|
| Mobile phases: | Solution A: aqueous solution of 0.05% trifluoroacetic acid<br>Solution B: methanol |
| Sample solution: | Solution of 10K NBP-A fraction degraded with thiol |
| Column: | Inertsil ODS-3, GL Science, 4.6 mm × 250 mm, S/N 6J186211 |
| Amount injected: | 2 µl |
| UV wavelength: | 280 nm |
| Column temperature: | Constant temperature at around 25° C. |
| Mobile phase flow rate: | 1 ml/min |
| Method of ionization: | Positive ESI |
| Method of scanning: | TOF-MS scanning |
| Range of measurement: | m/z 100 to 1000 |

| Gradient conditions: | | | | | | |
|---|---|---|---|---|---|---|
| | Time (min) | | | | | |
| | 0.0 | 5.0 | 60 | 70 | 70.1 | 85.0 |
| Solution A (%) | 95 | 95 | 0 | 0 | 95 | 95 |
| Solution B (%) | 5 | 5 | 100 | 100 | 5 | 5 |

(3-5) Results

The results of LC-MS assay are summarized in Table 14.

Elementary compositions of the peaks detected via TIC were computed based on the accurate m/z values of the MS-detected peaks shown in Table 14.

TABLE 14

Results of LC-MS assay

| Peak | HPLC retention time | Major MS detection peak | Corresponding diagram |
|---|---|---|---|
| Peak (1) | 26.28 min | m/z 459.1 | FIGS. 14, 15, and 16-1 to 16-4 |
| Peak (2) | 42.31 min | m/z 413.1 | FIGS. 14, 15, and 17-1 to 17-4 |
| Peak (3) | 43.35 min | m/z 565.1 | FIGS. 14, 15, and 18-1 to 18-4 |

LC-MS analysis involved the use of the same column as used in Example 5 (1) and the use of an apparatus different from the apparatus used therein. Thus, the elution time was somewhat different from that shown in FIG. 2. According to the correlation with other peaks, the peak at 24 min in FIG. 2 was found to correspond to peak (1) at 26 min observed in LC-MS, the peak at 40 min in FIG. 2 was found to correspond to peak (2) at 42 min observed in LC-MS, and the peak at 41 min in FIG. 2 was found to correspond to peak (3) at 43 min observed in LC-MS. Since the mass-to-charge ratio (m/z) of the protonated molecular ions ([M+H]+) is assayed via LC-MS, peak (1) detected via LC-MS was found to correspond to epigallocatechin gallate having a molecular weight of 458, peak (2) was found to correspond to a benzyl thioether derivative of epicatechin having a molecular weight of 412, and peak (3) was found to correspond to a benzyl thioether derivative of epicatechin gallate having a molecular weight of 564.

Peak (2) was found to correspond to a benzyl thioether derivative of epicatechin via a comparison with the results of HPLC analysis of thiol-degraded procyanidin C1. Peak (3) was found to correspond to a benzyl thioether derivative of epicatechin gallate via a comparison with the results of HPLC analysis of thiol-degraded Gravinol®. Also, peak (1) was confirmed to be underivatized epigallocatechin gallate via a comparison of the results of HPLC analysis of epigallocatechin gallate with those of a commercially available reagent.

(4) Summary of Analysis of Constituents

The thiol-degraded product of cashew apple-derived proanthocyanidin of the present invention obtained by allowing benzyl mercaptan to react therewith under acidic conditions encompasses a compound that is deduced to have a structure shown in putative structural formula 1 (i.e., a compound exhibiting the mass peak shown in Table 7 detected via ESI-MS analysis under the conditions shown in Table 5 and peaks at the chemical shifts shown in Tables 8 and 9 detected via $^1$H NMR and $^{13}$C NMR analyses under conditions shown in Table 6), a compound that is deduced to have a structure shown in putative structural formula 2 (i.e., a compound exhibiting the mass peak shown in Table 10 detected via ESI-MS analysis under the conditions shown in Table 5 and peaks at the chemical shifts shown in Tables 11 and 12 detected via $^1$H NMR and $^{13}$C NMR analyses under conditions shown in Table 6), a benzyl thioether derivative of epicatechin, a benzyl thioether derivative of epicatechin gallate, and epigallocatechin gallate. Based thereon, cashew apple-derived prodelphinidin is deduced to be a condensate comprising, as constituents, (epi)gallocatechin, (epi)gallocatechin gallate, epicatechin, epicatechin gallate, and epigallocatechin gallate, and the lower end unit composed of epigallocatechin gallate.

Polymerization via a covalent bond between carbon at position 4 of the chroman ring in the flavonoid backbone as a constitutional unit and another site in the adjacent constitutional unit (deduced to be carbon at position 8 or 6 of the chroman ring, see Non-Patent Document 1, for example) was found based on the fact that a site of binding of benzyl thioether to a thiol-degraded product was carbon at position 4.

The lower end unit was found to be epigallocatechin gallate based on the fact that a component of a thiol-degraded product that was not derivatized by benzyl thioether was limited to epigallocatechin gallate.

Example 6

Degree of Polymerization of Proanthocyanidin Polymers Derived from Cashew Apple

In Example 5, components constituting the proanthocyanidin polymers derived from cashew apple and the lower end unit were deduced. In this example, a degree of polymerization is deduced.

In order to deduce a degree of polymerization of proanthocyanidin, proanthocyanidin was examined by the method described in Non-Patent Document 1 (J. Agric. Food Chem., 2003, 51, 7513-7521) or other documents. In such method, a degree of polymerization is calculated by HPLC analysis of the thiol-degraded product conducted in Example 5 (detection wavelength: 280 nm) based on a comparison of areas of catechins and those of benzyl thioether derivatives of other catechins at the lower end unit.

In the articles such as Non-Patent Document 1, only catechin or epicatechin derivatives were detected in many plants. Accordingly, the calculation formula cannot be applied to other catechins having different structures. Thus, the average degree of polymerization and the proportion of constituents were calculated in accordance with the following procedure.

(1) Procedures of Analysis (i) The 8 ultrafiltration fractions of proanthocyanidin polymers derived from cashew apple prepared in Example 3 were subjected to thiol degradation in accordance with the procedure described in Example 5.

(ii) The thiol-degraded products were analyzed via HPLC under the same conditions as in Example 5 (column: ODS-3, 4.6×250 mm) and the peak areas at 280 nm were measured.

(iii) With the use of epicatechin (purity of 98% or higher), epigallocatechin (purity of 98% or higher), epigallocatechin gallate (purity of 90% or higher), and epicatechin gallate (purity of 98% or higher) of Wako Pure Chemical Industries, Ltd. as the standards, HPLC analysis was carried out at a plurality of concentrations (under the same conditions as in Example 5).

(iv) Calibration curves of the concentration versus peak area ratio of catechin compounds were prepared based on the peak areas of samples at 280 nm.

(v) Concentrations of the epigallocatechin gallate, the (epi) gallocatechin benzyl thioether derivative, the (epi)gallocatechin gallate benzyl thioether derivative, the epicatechin benzyl thioether derivative, and the epicatechin gallate benzyl thioether derivative in the thiol-degraded products were calculated based on the calibration curves of the relevant catechin compounds, and the determined concentrations were converted into molar concentrations in accordance with molecular weights.

(vi) The average degree of polymerization (mDP) was calculated by the following calculation formula based on the ratio of molar concentrations.

Calculation formula: average degree of polymerization={[molar concentration of (epi)gallocatechin derivative]+[molar concentration of (epi)gallocatechin gallate derivative]+[molar concentration of epicatechin derivative]+[molar concentration of epicatechin gallate derivative]}/{molar concentration of epigallocatechin gallate}+1.

(vii) Proportions of components are in terms of molar concentrations.

TABLE 15

Molar concentration (mM), ratio of molar concentration (%), and average degree of polymerization of each component of thiol-degraded NBP-M

| Ultrafiltration fraction | Epigallocatechin gallate | (Epi)gallocatechin derivative | (Epi)gallocatechin gallate derivative | Epicatechin derivative | Epicatechin gallate derivative | Average degree of polymerization (mDP) |
|---|---|---|---|---|---|---|
| 100K or higher | | | | | | |
| Concentration (mM) | 0.012888629 | 0.569583448 | 0.28844653 | 0.061031535 | 0.018164354 | 73.7 |
| Percentage (%) | 1.4 | 59.9 | 30.4 | 6.4 | 1.9 | |

TABLE 15-continued

Molar concentration (mM), ratio of molar concentration (%), and average degree of polymerization of each component of thiol-degraded NBP-M

| Ultrafiltration fraction | Epigallocatechin gallate | (Epi)gallocatechin derivative | (Epi)gallocatechin gallate derivative | Epicatechin derivative | Epicatechin gallate derivative | Average degree of polymerization (mDP) |
|---|---|---|---|---|---|---|
| 100K to 50K | | | | | | |
| Concentration (mM) | 0.013906294 | 0.508731887 | 0.253594636 | 0.052969435 | 0.015602984 | 60.7 |
| Percentage (%) | 1.6 | 60.2 | 30.0 | 6.3 | 1.8 | |
| 50K to 30K | | | | | | |
| Concentration (mM) | 0.017088782 | 0.561601368 | 0.274860634 | 0.056329975 | 0.017487443 | 54.3 |
| Percentage (%) | 1.8 | 60.6 | 29.6 | 6.1 | 1.9 | |
| 30K to 10K | | | | | | |
| Concentration (mM) | 0.020299434 | 0.444887261 | 0.230434707 | 0.049679008 | 0.015114098 | 37.5 |
| Percentage (%) | 2.7 | 58.5 | 30.3 | 6.5 | 2.0 | |

TABLE 16

Molar concentration (mM), ratio of molar concentration (%), and average degree of polymerization of each component of thiol-degraded NBP-A

| Ultrafiltration fraction | Epigallocatechin gallate | (Epi)gallocatechin derivative | (Epi)gallocatechin gallate derivative | Epicatechin derivative | Epicatechin gallate derivative | Average degree of polymerization (mDP) |
|---|---|---|---|---|---|---|
| 100K or higher | | | | | | |
| Concentration (mM) | 0.013646433 | 0.601539228 | 0.302237701 | 0.060483944 | 0.024077231 | 73.4 |
| Percentage (%) | 1.4 | 60.0 | 30.2 | 6.0 | 2.4 | |
| 100K to 50K | | | | | | |
| Concentration (mM) | 0.020523872 | 0.675080425 | 0.338031479 | 0.064325068 | 0.020118723 | 54.5 |
| Percentage (%) | 1.8 | 60.4 | 30.2 | 5.8 | 1.8 | |
| 50K to 30K | | | | | | |
| Concentration (mM) | 0.028299208 | 0.637272379 | 0.294318934 | 0.057375012 | 0.017102298 | 36.6 |
| Percentage (%) | 2.7 | 61.6 | 28.5 | 5.5 | 1.7 | |
| 30K to 10K | | | | | | |
| Concentration (mM) | 0.042659749 | 0.631859462 | 0.323892763 | 0.061289355 | 0.020236252 | 25.3 |
| Percentage (%) | 4.0 | 58.5 | 30.0 | 5.7 | 1.9 | |

The lower end unit of the proanthocyanidin is epigallocatechin gallate, and the proanthocyanidin is a polymerized product of the components described as "derivatives." The average degree of polymerization was found to be 25-mer to 73-mer, and the amounts of major components: i.e., (epi)gallocatechin and (epi)gallocatechin gallate, were found to be 58.5% to 61.6% and 28.5% to 30.4%, respectively. Since such naturally occurring proanthocyanidin polymer has not yet been reported, such polymer is considered to be a proanthocyanidin polymer peculiar to cashew apple.

Example 7

Comparison of Activity of Proanthocyanidin Polymers Derived from Cashew Apple and that of Other Alpha-Amylase Inhibiting Components Alpha-amylase inhibitory activities ($IC_{50}$) (the final specimen concentrations) of proanthocyanidin polymers derived from cashew apple, other alpha-amylase inhibiting components, and Gravinol® (grape seed-derived proanthocyanidin) were assayed, and activities were compared and examined. Assay was carried out in the same manner as in Example 1 (2), and all the specimens were subjected to the assay on the same day.

Methods to prepare the specimens are described below.
(i) Banso Reicha®-Derived C18-Binding Polyphenol Component A tea beverage sample containing polyphenols from guava leaves (500 g, Banso Reicha®, Yakult) was applied to C18 Cartridges (Sep-Pak Vac 35 cc, Waters), and non-adsorbed components were washed with a sufficient amount of purified water. The components bound to the C18 resin were eluted with methanol and dried via vacuum distillation to collect 363 mg of Banso Reicha®-derived C18-binding polyphenol (Banso reicha PP). An aqueous solution of 0.2% Banso reicha PP was prepared and filtered through a 0.22-μm filter (Millex GP, Millipore), and the resulting solution was employed as a specimen.
(ii) Gravinol® (Grape Seed-Derived Proanthocyanidin)

An aqueous solution of 0.2% Gravinol® (a grape seed extract, Kikkoman) was prepared and filtered through a 0.22-μm filter (Millex GP, Millipore), and the resulting solution was employed as a specimen.
(iii) Acarbose Acarbose is used as an inhibitor of elevated blood glucose level having glucosidase inhibitory activity (i.e., a pharmaceutical preparation). Since it has alpha-amylase inhibitory activity, it was used as a control sample. In the experiment, an aqueous solution of 0.4% Acarbose reagent (LKT Laboratories, Inc.) was prepared and filtered through a 0.22-µm filter (Millex GP, Millipore), and the resulting solution was employed as a specimen.

(iv) Proanthocyanidin Polymers Derived from Cashew Apple

An aqueous solution of 0.1% 100 K or greater ultrafiltration fraction of cashew apple-derived NBP-A prepared in Example 3 was prepared and filtered through a 0.22-µm filter (Millex GP, Millipore), and the resulting solution was employed as a specimen.

The results of assay are shown in the table below.

TABLE 17

Comparison of alpha-amylase inhibitory activities ($IC_{50}$) of specimens

| | Specimens | Alpha-amylase inhibitory activity ($IC_{50}$) |
|---|---|---|
| (i) | Banso reicha PP | 40.0 µg/ml |
| (ii) | Gravinol ™ | 3.6 µg/ml |
| (iii) | Acarbose | 64.3 µg/ml |
| (iv) | Cashew apple-derived proanthocyanidin polymer | 1.2 µg/ml |

As a result of assay, the proanthocyanidin polymers derived from cashew apple were found to have potent alpha-amylase inhibitory activity. That is, the activity of the proanthocyanidin polymers derived from cashew apple is 33 times greater than that of Banso reicha PP. Ingestion of 70 mg or more Banso Reicha® (in terms of polyphenols from guava leaves) per meal can yield a certain degree of effects, and Banso Reicha® is approved as a specified health food product by the Ministry of Health, Labour and Welfare, Japan. This indicates that ingestion of 2.2 mg or more proanthocyanidin polymers derived from cashew apple per meal can attain the equivalent effects of suppressing elevation in blood glucose levels. Specifically, incorporation of proanthocyanidin polymers derived from cashew apple in an amount as little as at least 0.0001% or more in 220 g of purified water can provide a food or beverage composition having alpha-amylase inhibitory activity. In addition, influence thereof on the flavor or other properties of the processed food or beverage products into which the proanthocyanidin polymers are incorporated can be insignificant.

As shown in Table 17, the proanthocyanidin polymers derived from cashew apple of the present invention comprising prodelphinidin as a major component had higher alpha-amylase inhibitory activity than procyanidin (Gravinol®). It can be thus concluded that proanthocyanidin polymers containing a prodelphinidin component has higher alpha-amylase inhibitory activity than procyanidin.

Example 8

Comparison of Activity of Proanthocyanidin Polymers Derived from Cashew Apple with that of Other Lipase Inhibitory Component It is known that the suppression of lipid absorption is effective for obesity control, and many lipase activity-inhibitory components have been studied and developed. A tea beverage sample (tradename: Kuro oolong cha, Suntory) contains Oolong tea polyphenols, lipase is inhibited by the action of such Oolong tea polyphenols, and lipid absorption is suppressed. Because of such effects, Kuro oolong cha was approved as a specified health food product by the Ministry of Health, Labor and Welfare, Japan.

In this example, $IC_{50}$s (the final specimen concentration) for the inhibition of the lipase activities of proanthocyanidin polymers derived from cashew apple, the components of the tea beverage sample, and other lipase activity inhibiting components were assayed, and inhibitory activities were compared and examined.

Assay was carried out in accordance with Non-Patent Document 2 (J. Agric. Food Chem., 2007, 55, 4604-4609). A specimen solution was added to a 96-well fluorescence plate at 25 µl/well. A lipase solution (lipase from porcine pancreas Type II, SIGMA) prepared with the use of PBS(−) was added to the plate of the test group at 25 µl/well and PBS(−) was added to the plate of the blind test group at 25 µl/well. A 0.1 mM fluorescent substrate solution (4-methylumbelliferyl oleate, Fluka) prepared with the use of PBS(−) was added thereto at 50 µl/well, and the reaction was then allowed to proceed for 20 minutes. A 0.1 M sodium citrate solution (pH 4.2) was added as a reaction terminator at 100 µl/well, and fluorescence intensity was assayed using a fluorescence plate reader (Ex 365 nm, Em 450 nm). In a blank test, samples of the test group and of the blind test group were prepared and fluorescence intensity was assayed in the same manner as described above, except that the same amount of a solvent used for the preparation of a specimen solution was used instead of "specimen solution." The percentage of lipase inhibition was determined by the following formula.

<Calculation Formula>

Lipase inhibitory activity(%)=(1−(A−B)/(C−D))×100

A: fluorescence intensity in the blind test using a sample solution
B: fluorescence intensity in the test of the present invention using a sample solution
C: fluorescence intensity in the blind test using a blank solution (a dilute solvent)
D: fluorescence intensity in the test of the present invention using a blank solution (a dilute solvent)

Enzyme inhibitory activities of the sample solutions were assayed at a plurality of concentrations, and the concentration at which 50% of the lipase activity is inhibited ($IC_{50}$) was determined.

Types of specimens used in the test of the present invention and a method to prepare specimen solutions are described below.

(i) Kuro Oolong Cha-Derived C18-Binding Polyphenol Component

A commercially available tea beverage sample (500 g, Kuro Oolong cha, Suntory) was applied to C18 Cartridges (Sep-Pak Vac 35 cc, Waters), and non-adsorbed components were washed with a sufficient amount of purified water. The components bound to the C18 resin were eluted with methanol and dried via vacuum distillation to collect 442.9 mg of Kuro Oolong cha-derived C18-binding polyphenol (Kuro Oolong cha PP). It is necessary for such polyphenol to be dissolved in purified water when used for oral application; however, purified Kuro Oolong cha PP is not substantially dissolved in purified water. Accordingly, a 1.0% solution thereof was prepared with the aid of an aqueous solution of 50% (W/W) methanol, the resulting solution was filtered through a 0.22-µm filter (Millex GP, Millipore), and the resulting solution was employed as a specimen. The specimen solution was diluted with purified water. As with the dilution ratio of the specimens, the lipase inhibitory activity of an aqueous 50% methanol solution was also assayed, although no lipase inhibitory activity was observed.

(ii) Epigallocatechin Gallate

Patent Document 5 (JP Patent Publication (Kokai) No. 2006-1909 A) (title of the invention: a novel compound having lipase inhibitory activity) describes that epigallocatechin gallate has lipase inhibitory activity. Accordingly, an aqueous solution of 0.2% epigallocatechin gallate (Wako Pure Chemical Industries, Ltd.) was prepared and filtered through a 0.22-µm filter (Millex GP, Millipore), and the resulting solution was employed as a specimen.

(iii) Gravinol® (Grape Seed-Derived Proanthocyanidin)

An aqueous solution of 0.2% Gravinol® (grape seed extract, Kikkoman) was prepared and filtered through a 0.22-µm filter (Millex GP, Millipore), and the resulting solution was employed as a specimen.

(iv) Chlorogenic Acid

An aqueous solution of 1.0% chlorogenic acid (MP Biomedicals, Inc.) described in Non-Patent Document 2, which describes a method of lipase assay, was prepared and filtered through a 0.22-µm filter (Millex GP, Millipore), and the resulting solution was employed as a specimen.

(v) Proanthocyanidin Polymers Derived from Cashew Apple

An aqueous solution of 0.2% 100 K or greater ultrafiltration fraction of cashew apple-derived NBP-A prepared in Example 3 was prepared and filtered through a 0.22-µm filter (Millex GP, Millipore), and the resulting solution was employed as a specimen.

The results of assay are shown in the table below.

TABLE 18

| | Specimens | Lipase inhibitory activity ($IC_{50}$) |
|---|---|---|
| (i) | Kuro Oolong cha PP | 4.7 µg/ml |
| (ii) | Epigallocatechin gallate | 20.0 µg/ml |
| (iii) | Gravinol ™ | 1.0 µg/ml |
| (iv) | Chlorogenic acid | 77.5 µg/ml |
| (v) | Cashew apple-derived proanthocyanidin polymer | 0.5 µg/ml |

$IC_{50}$ of proanthocyanidin polymers derived from cashew apple was 0.5 µg/ml and that of chlorogenic acid simultaneously assayed was 77.5 µg/ml. In Non-Patent Document 2, lipase inhibitory activity ($IC_{50}$) of 9-mer or greater procyanidin is described to be 0.9 µg/ml and that of chlorogenic acid simultaneously assayed is described to be 59.8 µg/ml. It is thus considered that activity of proanthocyanidin polymers containing a prodelphinidin component is much stronger than that of procyanidin polymers (i.e., catechin and epicatechin polymers).

As shown in Table 18, proanthocyanidin polymers derived from cashew apple of the present invention mainly composed of prodelphinidin had higher lipase inhibitory activity than procyanidin (i.e., Gravinol®). This indicates that proanthocyanidin polymers containing a prodelphinidin component have higher lipase inhibitory activity than procyanidin.

The above results demonstrate that proanthocyanidin polymers derived from cashew apple have very high lipase inhibitory activity. Since Kuro Oolong cha PP is not sufficiently dissolved in purified water, insoluble precipitation may occur with the use of an aqueous solution. Based on the fact that proanthocyanidin polymers derived from cashew apple exhibit the values smaller than the values described in literature, it can be said that proanthocyanidin polymers derived from cashew apple have very high lipase inhibitory activity. The amount of Kuro Oolong cha ingested in the form of a specified health food product is 70 mg. Based on the assay results, the amount of proanthocyanidin polymers derived from cashew apple exhibiting equivalent activity is 7.5 mg. Specifically, proanthocyanidin polymers derived from cashew apple may be incorporated in an amount of at least 0.0075% in 100 g of processed food or beverage, so that a food or beverage composition having lipase inhibitory activity can be provided.

Example 9

Assay of Bacterial Lipase Inhibitory Activity

Bacterial lipase is known to be produced by bacteria existing on the surface layer of the skin, such as *Propionibacterium acnes* (popular name: acne-causing bacteria), bacteria of *Micrococcus* (*Micrococcus* sp.), and bacteria of *Pseudomonas* (*Pseudomonas* sp.). Regarding *Propionibacterium acnes*, in particular, the problems, such as the increased bacterial count and elicitation of dermal inflammation caused by free fatty acids generated by lipase, have been studied, and it is known that a lipase inhibitor is effective to overcome such problems.

In order to extensively evaluate lipase inhibitory activities of the product of the present invention and of a plurality of known components, lipase derived from commercially available bacteria of *Pseudomonas* (*Pseudomonas* sp.) was used. *Pseudomonas* is a family of gram-negative aerobic bacteria. A representative example of well-known bacteria is *P. aeruginosa*. In the experiment, lipase from *Pseudomonas* sp. (type XIII, ≥15 units/solid, L9518, Sigma-Aldrich Japan) was used. This lipase is a very potent enzyme. From the preliminary inquiry to the inhibitory activity test, 0.1 µg/ml of a lipase solution was used. In the experiment, fractions obtained in Examples 2 and 3 containing proanthocyanidin polymers derived from cashew apple of the present invention were subjected to the assay. The following reagent was used as a control sample to assay lipase inhibitory activity.

<Test Material Used in Bacterial Lipase Activity Inhibitory Test: The Product of the Present Invention>

(1) Lyophilized Powder of 10 K Ultrafiltration Concentrate Derived from Cashew Apple Puree of the Present Invention Cashew apple puree (4,773 g) was concentrated via ultrafiltration using an ultrafiltration membrane having a molecular weight cut-off of 10,000 (Hydrosart® 10 KDa, Sartorius) in the manner described in Example 2, and the concentrate was lyophilized to obtain 26.4 g of powder.

(2) Lyophilized Powder of Cashew Apple-Derived HP-20 Resin Purified Product of the Present Invention The lyophilized product (about 26 g) of the 10 K ultrafiltration concentrate obtained in (1) above was used as a sample, the sample was subjected to purification with the use of the HP-20 resin in the manner described in Example 2, and 3.7 g of powder was obtained via lyophilization.

(3) Proanthocyanidin Polymers Derived from Cashew Apple of the Present Invention (an Aqueous NBP-M Solution)

The lyophilization products of the four fractions prepared via fractionation with the LH-20 resin column and elution with methanol in Example 2 and fractionation with an ultrafiltration membrane in the manner described in Example 3 were dissolved in water to prepare 0.1% aqueous solutions, and the solutions were mixed in accordance with the weight ratio of the fractions to form a solution. The solution was designated as an aqueous NBP-M solution.

(4) Proanthocyanidin Polymers Derived from Cashew Apple of the Present Invention (an Aqueous NBP-A Solution)

The lyophilization products of the four fractions prepared via fractionation with the LH-20 resin column and elution with an aqueous solution of 70% acetone in Example 2 and fractionation with an ultrafiltration membrane in the manner described in Example 3 were dissolved in water to prepare 0.1% aqueous solutions, and the solutions were mixed in accordance with the weight ratio of the fractions to form a solution. The solution was designated as an aqueous NBP-A solution.

<Test Material of Bacterial Lipase Activity Inhibition Test: Control Sample>

(5) Tetracycline Hydrochloride (Manufactured by Wako Pure Chemical Industries, Ltd. for Biochemical Use, Purity: 90% or Higher, 205-08591)

It is tetracycline antibiotics. It inhibits protein synthesis of microorganisms and exhibits broad antibacterial spectra. Tetracycline antibiotics are extensively used for internal and external applications with the aid of lipase inhibitory activity. Tetracycline antibiotics are described in Patent Document 7 (JP Patent Publication (Kokai) No. 2008-19180 A) and the like as comparative substances in terms of lipase inhibitory activity.

(6) 3,4-Dihydroxycinnamic Acid (Caffeine Acid, Caffeic Acid: Wako Pure Chemical Industries, Ltd., Wako 1st-Grade, Purity: 98% or Higher)

It is described in Patent Document 8 (JP Patent Publication (Kokai) No. 2005-53891 A) as an active component for bacterial lipase inhibition.

(7) Gallic Acid (Gallic Acid Monohydrate, Wako Pure Chemical Industries, Ltd., Wako 1st-Grade)

It is described in Patent Document 8 (JP Patent Publication (Kokai) No. 2005-53891 A) as an active component for bacterial lipase inhibition.

(8) Chlorogenic Acid (Manufactured by MP Biomedicals Inc., Imported and Sold by Wako Pure Chemical Industries, Ltd. for Industrial Use)

Non-Patent Document 2 (J. Agric. Food Chem., 2007, 55, 4604-4609) describes chlorogenic acid as an active component for inhibiting pancreatic lipase.

(9) (−)-Epigallocatechin Gallate (Manufactured by Wako Pure Chemical Industries, Ltd. for Biochemical Use, Purity: 90% or Higher)

Epigallocatechin gallate is reported as a pancreatic lipase inhibitory activity component. In addition, it is highly likely that a part of a major component of the proanthocyanidin polymers of the present invention.

<Method of Lipase Inhibitory Activity Test>

Assay was carried out in accordance with Non-Patent Document 2 (J. Agric. Food Chem., 2007, 55, 4604-4609). A specimen diluent and a blank solution (a specimen diluent) were added to a 96-well fluorescence plate and then at 25 μl/well. A lipase solution prepared with the use of PBS(−) (lipase from *Pseudomonas* sp. Type XIII, SIGMA) was added to the test of the present invention at 25 μl/well and PBS(−) was added to the blind test group at 25 μl/well. A 0.1 mM fluorescent substrate solution (4-methylumbelliferyl oleate, Fluka) prepared with the use of PBS(−) was added thereto at 50 μl/well, and the reaction was then allowed to proceed for 20 minutes. A 0.1 M sodium citrate solution (pH 4.2) was added as a reaction terminator at 100 μl/well, and fluorescence intensity was assayed using a fluorescence plate reader (Ex 365 nm, Em 450 nm). Lipase inhibitory activity was determined by the following formula. 3,4-Dihydroxycinnamic acid and gallic acid were dissolved in an aqueous solution of 10% methanol, and a blank solvent was subjected to the assay with the use of an aqueous methanol solution at the same concentration.

<Calculation Formula>

Lipase inhibitory activity(%)=(1−(A−B)/(C−D))×100

A: fluorescence intensity in the blind test using a sample solution
B: fluorescence intensity in the test of the present invention using a sample solution
C: fluorescence intensity in the blind test using a blank solution (a dilute solvent)
D: fluorescence intensity in the test of the present invention using a blank solution (a dilute solvent)

Enzyme inhibitory activities of the sample solutions were assayed at a plurality of concentrations, the data were logarithmically plotted, and the concentration at which 50% of lipase activity was inhibited ($IC_{50}$) was determined by the least-square method.

The results of assay of the specimens (1) to (9) are shown in the table below.

TABLE 19

Lipase inhibitory activities ($IC_{50}$) of specimens

| Specimens | Activity of bacterial lipase inhibition ($IC_{50}$) |
|---|---|
| (1) The invention (10K ultrafiltration concentrate) | 39.7 μg/ml |
| (2) The invention (HP-20 resin-purified product) | 5.6 μg/ml |
| (3) The invention (aqueous NBP-M solution) | 2.8 μg/ml |
| (4) The invention (aqueous NBP-A solution) | 1.3 μg/ml |
| (5) Tetracycline hydrochloride | 134.6 μg/ml |
| (6) 3,4-Dihydroxycinnamic acid (caffeic acid) | 42.3 μg/ml |
| (7) Gallic acid monohydrate | 574.2 μg/ml |
| (8) Chlorogenic acid | 69.2 μg/ml |
| (9) (−)-Epigallocatechin gallate | 918.8 μg/ml |

The results demonstrate that aqueous solutions of NBP-M and NBP-A exhibit very high inhibitory activity against bacterial lipase. Since the 10K ultrafiltration concentrate of (1) has higher inhibitory activity than tetracycline hydrochloride or 3,4-dihydroxycinnamic acid, a roughly purified product containing the proanthocyanidin polymers of the present invention was found to be capable of yielding sufficient activity.

Example 10

Bacterial Lipase Inhibitory Activity of Ultrafiltration Fraction of Proanthocyanidin Polymers Derived from Cashew Apple Using the powders prepared by fractionation via ultrafiltration and lyophilization in Example 3, the relationship between the molecular weight and the bacterial lipase inhibitory activity was examined. The lipase inhibitory activity test was carried out in the manner described in Example 9. The results are shown in the table below.

TABLE 20

Molecular weight cut-off and bacterial lipase inhibitory activity of proanthocyanidin polymer derived from cashew apple

| NBP-M | Bacterial lipase ($IC_{50}$) | NBP-A | Bacterial lipase ($IC_{50}$) |
|---|---|---|---|
| 100K NBP-M | 0.9 μg/ml | 100K NBP-A | 0.9 μg/ml |
| 50K NBP-M | 1.4 μg/ml | 50K NBP-A | 1.2 μg/ml |
| 30K NBP-M | 3.0 μg/ml | 30K NBP-A | 1.9 μg/ml |
| 10K NBP-M | 11.4 μg/ml | 10K NBP-A | 3.7 μg/ml |

The results demonstrate that the bacterial lipase inhibitory activity tends to be enhanced as the molecular weight of the proanthocyanidin polymer derived from cashew apple is increased. Thus, the bacterial lipase inhibitory activity of the roughly purified product may be much enhanced by treating the polymer with the use of an ultrafiltration membrane having a molecular weight cut-off of greater than 10,000. This indicates that a type of ultrafiltration membrane can be selected from the viewpoint of the intensity of the lipase inhibitory activity and the production efficiency required for the final product. However, the lipase inhibitor of the present invention is not necessarily subjected to ultrafiltration membrane treatment. The fact that the lipase inhibitor contains a sufficient amount of the proanthocyanidin polymer derived from cashew apple is the most important feature thereof.

A pharmaceutical product (Staderm ointment cream, Torii Pharmaceutical Co., Ltd.) contains ibuprofenpiconol described in Patent Document 7 (JP Patent Publication (Kokai) No. 2008-19180 A) in an amount of 5% therein as a lipase inhibitor. Thus, incorporation of a roughly purified product of the 10 K ultrafiltration concentrate of the present invention in an amount of 5% or less in the pharmaceutical product is deduced to yield sufficient effects. Further, incorporation of at least 0.05% of purified 100 K NBP-A is deduced to be sufficient for the following reasons. That is, it can be said that 100 K NBP-A has 100 times or higher lipase inhibitory activity than that of tetracycline hydrochloride having the lipase inhibitory activity equivalent to that of ibuprofenpiconol as a result of a comparison of lipase inhibitory activities ($IC_{50}$). Therefore, a composition comprising the product of the present invention, i.e., proanthocyanidin polymers derived from cashew apple in an amount of 0.001% to 10%, and preferably 0.01% to 5% therein, can be effective as a lipase inhibitory composition.

Reference Experiment: Assay of Antioxidation Activity Via DPPH Radical Elimination A solution of a stable radical, diphenyl-p-picrylhydradil (DPPH), in ethanol was used to evaluate the antioxidation activity. Ethanol (1,200 µl) and 400 µl of specimens (adjusted at an arbitrary concentration) were mixed with 1,600 µl of 250 mM acetate buffer (pH 5.5), and the mixture was preincubated at 30° C. for 5 minutes. A 500 µM DPPH/ethanol solution (800 µl) was added thereto, the resulting mixture was allowed to stand at 30° C. for 30 minutes, and the absorbance at 517 nm was assayed. When the control sample dissolved in ethanol was used as a specimen, 800 µl of ethanol, 400 µl of a solution of specimens in ethanol, and 400 µl of purified water were mixed, and the resulting mixture was preincubated at 30° C. for 5 minutes. A 500 µM DPPH/ethanol solution (800 µl) was added thereto, the resulting mixture was allowed to stand at 30° C. for 30 minutes, and the absorbance at 517 nm was assayed. A solution prepared in the same manner except for the use of purified water was used as a control sample. Based on the absorbance assayed, the percentage of radical elimination was determined by the following formula.

Radical elimination(%)=(1−[absorbance of sample]/[absorbance of control])×100

The concentration of the sample in the sample solution was gradually changed to determine the percentage of radical elimination, the concentration of the sample solution at which the percentage of DPPH radical elimination became 50% was determined, and the determined value was designated as the 50% elimination concentration of DPPH radicals. As the value is reduced, the capacity for radical elimination is enhanced. The specimens used for the test and the assay results are shown in the table below.

Specimens to be Assayed

<The Product of the Present Invention: the Same Specimens as Prepared in Example 9>

(1) The lyophilized product of the cashew apple puree-derived 10 K ultrafiltration concentrate of the present invention (a 10 K ultrafiltration concentrate)

(2) The lyophilized powder of the cashew apple-derived HP-20 resin-purified product of the present invention (an HP-20 resin-purified product)

(3) The proanthocyanidin polymer derived from cashew apple of the present invention (an aqueous NBP-M solution)

(4) The proanthocyanidin polymer derived from cashew apple of the present invention (an aqueous NBP-A solution)

<Control Sample: the Same Reagent as Used in Example 9>

(5) 3,4-Dihydroxycinnamic acid (caffeine acid, caffeic acid, Wako Pure Chemical Industries, Ltd., Wako 1 st-grade, purity: 98% or higher): dissolved in ethanol and then used for the experiment (6) Gallic acid (gallic acid monohydrate, Wako Pure Chemical Industries, Ltd., Wako 1st-grade): dissolved in ethanol and then used for the experiment (7) (−)-Epigallocatechin gallate (Wako Pure Chemical Industries, Ltd., for biochemical use, purity: 90% or higher): dissolved in purified water and then used for the experiment (8) L(+)-ascorbic acid (Kanto Chemical Co., Inc., special-grade): It was dissolved in purified water and the resulting solution was then used for the experiment.

TABLE 21

DPPH radical elimination activity test

| | Specimens | 50% Elimination concentration of DPPH radicals |
|---|---|---|
| (1) | The invention (10K ultrafiltration concentrate) | 40.2 µg/ml |
| (2) | The invention (HP-20 resin-purified product) | 8.2 µg/ml |
| (3) | The invention (aqueous NBP-M solution) | 3.2 µg/ml |
| (4) | The invention (aqueous NBP-A solution) | 3.4 µg/ml |
| (5) | 3,4-Dihydroxycinnamic acid (caffeic acid) | 2.8 µg/ml |
| (6) | Gallic acid monohydrate | 1.2 µg/ml |
| (7) | (−)-Epigallocatechin gallate | 2.0 µg/ml |
| (8) | L(+)-ascorbic acid | 3.9 µg/ml |

As a result of the assay, the purified products of the present invention; i.e., (3) an aqueous NBP-M solution and (4) an aqueous NBP-A solution, were found to have sufficient antioxidative properties equivalent to those of ascorbic acid, which is an antioxidative component. Also, antioxidative properties were observed in roughly purified products (i.e., the 10 K ultrafiltration concentrate and the HP-20 resin-purified product). According to these results, lipase inhibitory activity is not correlated with radical-eliminating activity. The product of the present invention has the lipase inhibitory capacity independently of the antioxidative capacity.

Example 11

Examination of Various Pectinase Treatments and Amylase Inhibitory Activity (1) Purpose of Experiment In the above examples, pectinase A "Amano" (Amano Enzyme Inc.) was used. This example is intended to confirm whether or not the processed cashew apple puree product having the above activity could be obtained when other pectinase products (pectinase G "Amano" and pectinase PL "Amano" (Amano Enzyme Inc.) were used.

(2) Raw Material of Cashew Apple Puree

Raw materials of cashew apple puree of a lot different from that of the raw materials used in Examples 1 to 10 were used.

(3) Procedure of Experiment (i) Cashew apple puree (20 g each) was fractionated to three 50-ml centrifuge tubes.

(ii) Pectinase A "Amano", pectinase G "Amano", and pectinase PL "Amano" (0.1 g each) were added to 20 g of cashew apple puree, and the resultants were heated in an incubator at 50° C. for 1 hour. The resultants were centrifuged at 3,000 rpm and 20° C. for 20 minutes, the supernatants after treatment were filtered through a 0.22-μm filter (Millex GP, Millipore GP, Millipore), and the resulting filtrates were designated as specimens.

(iii) The specimens were diluted with purified water to prepare aqueous solutions of 20%, 10%, 5%, 2.5%, and 1.25% specimens, and porcine pancreatic alpha-amylase inhibitory activity was assayed.

(4) Results of Experiment

Figure 19:
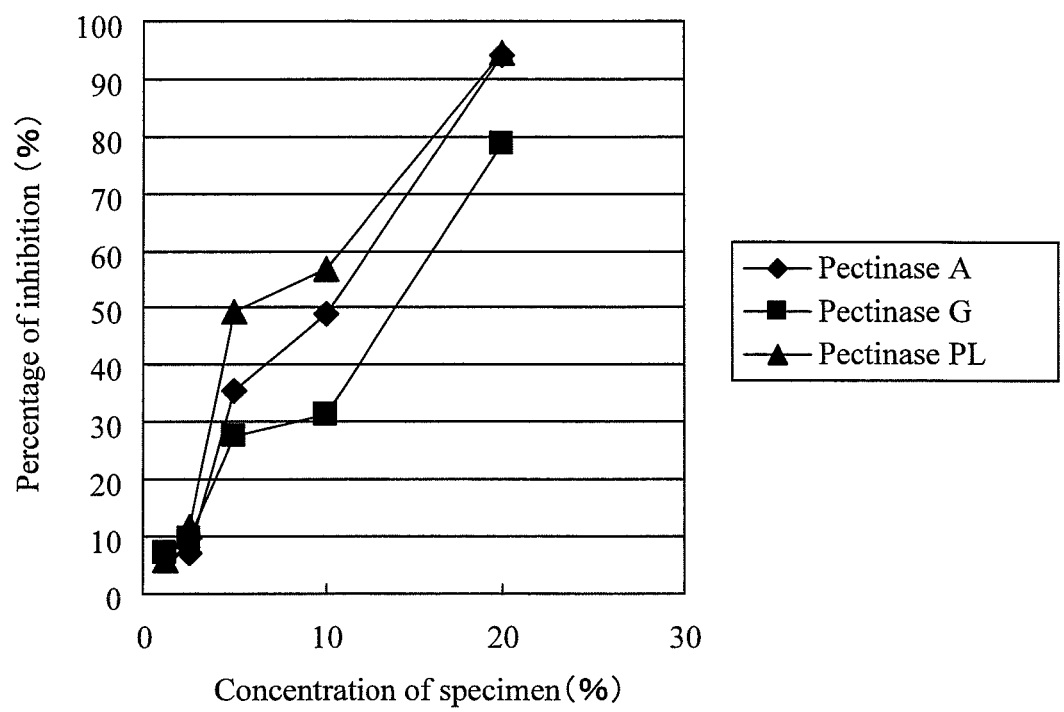
FIG. 19 shows the alpha-amylase inhibitory activity of a puree extract processed with the use of 3 types of pectinase preparations.

FIG. 19 shows the results of alpha-amylase inhibitory activity assay.

Amylase inhibitory activity was observed in all the enzyme-treated solutions.

(5) Observation of Results of Experiment

Pectinase A "Amano" is composed of 45% of pectinase, 25% of beta-amylase, and 30% of diatomaceous earth. Pectinase G "Amano" is composed of 90% of pectinase and 10% of diatomaceous earth. Pectinase PL "Amano" comprises 70% of pectinase as a major component, and it has pectinase activity and fiber digestibility. The processed cashew apple puree product of the present invention was obtained with the use of any of these 3 types of pectinase preparations having different compositions. Accordingly, any pectinase for food industrial use having pectinase activity can be used without problems.

Example 12

(1) Objective

This test is intended to confirm alpha-amylase inhibitory activity when cashew apple puree and a centrifuge residue are used as raw materials.

(2) Procedure

The procedure of experiment is as described below.

(i) Cashew apple puree (40.82 g) was centrifuged at 3,000 rpm and 20° C. for 20 minutes.

(ii) Purified water (14.4 g) was added to 5.6 g of the precipitate resulting from centrifugation of puree to prepare a suspension, 0.1 g of pectinase A "Amano" was added thereto, and the resultant was heated in an incubator at 50° C. for 1 hour. The resultant was centrifuged at 3,000 rpm and 20° C. for 20 minutes, the resulting supernatant was filtered through a 0.22-μm filter (Millex GP, Millipore), and the resulting filtrate was designated as specimen 1.

(iii) Pectinase A "Amano" (0.1 g) was added to 20 g of cashew apple puree, and the resultant was heated in an incubator at 50° C. for 1 hour. The resultant was centrifuged at 3,000 rpm and 20° C. for 20 minutes, the resulting supernatant was filtered through a 0.22-μm filter (Millex GP, Millipore), and the resulting filtrate was designated as specimen 2.

(iv) Specimens 1 to 5 were diluted with purified water to prepare aqueous solutions of 25%, 10%, and 5% specimens, and porcine pancreatic alpha-amylase inhibitory activity was assayed.

(3) Results of Experiment

The results of alpha-amylase inhibitory activity assay are shown in the table below.

TABLE 22

Amylase inhibitory activity of supernatant resulting from centrifugation of cashew apple puree

| | | Percentage of alpha-amylase inhibition | | |
|---|---|---|---|---|
| Specimen No. | Method of Specimen treatment | 25% aqueous solution | 10% aqueous solution | 5% aqueous solution |
| Specimen 1 | Pectinase treatment of residue of centrifugation and filtration thereof | 93.2% | 69.5% | 19.8% |
| Specimen 2 | Pectinase treatment of puree and filtration thereof | 82.5% | 69.4% | 44.0% |

Amylase inhibitory activity was observed in the centrifuge precipitate of puree and the filtrate of pectinase-treated puree.

Example 13

Assay of Antibacterial Activity Against *Propionibacterium acnes*

(1) Objective

The antibacterial activity of proanthocyanidin polymers derived from cashew apple of the present invention against *Propionibacterium acnes* was evaluated. To this end, the minimum inhibitory concentration (MIC) of the test material containing proanthocyanidin polymers derived from cashew apple against *Propionibacterium acnes* was assayed in accordance with the standard method of the Japanese Society of Chemotherapy (revised in 1993).

(2) Test Material

NBP and NBP-A (100K) were used as test materials containing proanthocyanidin polymers derived from cashew apple.

"NBP" refers to the HP-20 resin-purified product obtained by concentrating pectinase-processed cashew apple puree with the use of an ultrafiltration membrane having a molecular weight cut-off of 10,000 and purifying the concentrate with the HP-20 resin in Example 2.

"NBP-A (100K)" refers to a fraction obtained by concentrating a fraction (NBP-A) obtained by further purifying NBP with LH-20 resin in Example 2 with the use of an ultrafiltration membrane having a molecular weight cut-off of 100,000 in Example 3.

(3) Reagent etc

*Propionibacterium acnes* JCM $6425^T$ bacteria were used as the test bacteria.

Modified GAM agar medium (Nissui Pharmaceutical Co., Ltd.) was used for preculture of the test bacteria.

Mueller-Hinton broth, BBL, was used as both a solution for preparing a test bacterial solution and a medium for sensitivity assay.

(4) Test Method

Testing was carried out in accordance with the standard method of the Japanese Society of Chemotherapy.

(4-1) Preparation of Test Bacterial Solution

Cryopreserved bacteria were subjected to anaerobiotic culture at 36° C.±1° C. for 48 hours. The grown colonies were collected, suspended in the solution for preparing a test bacterial solution, and filtered with the use of cotton wool. The solution was adjusted to contain approximately $10^7$ CFU/ml of bacteria and the resultant was designated as the test bacterial solution.

(4-2) Preparation of Dilution Series of Test Material

The test material diluted at 3,200 µg/ml with sterile purified water (0.8 ml) was added to 0.8 ml of sterile ionized water to dilute the test material two-fold. Two-fold dilution was repeated in the same manner to prepare ten serial 2-fold dilutions of test materials in total (concentration of test solution: 1,600, 800, 400, 200, 100, 50, 25, 12.5, 6.25, and 3.125 µg/ml).

(4-3) Mixing of Media

A two-fold-diluted medium for sensitivity assay that had been fractionated in advance was mixed with the same amounts of solutions of the dilution series of test materials. As a result of mixing, the test solution was diluted two-fold (concentration of test solution: 800, 400, 200, 100, 50, 25, 12.5, 6.25, 3.125, and 1.5625 µg/ml), and the medium was also diluted two-fold and adjusted at a normal concentration. The necessary number of dilution series of the test materials mixed with the medium was fractionated to U-shaped wells of a microplate at 0.1 ml/well.

(4-4) Test Procedure

The test bacterial solution was added dropwise to wells of a microplate at 5 µl/well and subjected to anaerobiotic culture at 36° C.±1° C. for 48 hours. The sample to which bacteria were not added was designated as a negative control, the occurrence of bacterial growth (precipitation) was visually inspected, and the minimal concentration at which no bacterial growth was observed was designated as the MIC value.

(5) Test Results

The results of the growth test of the test materials (NBP and NBP-A (100K)) and the MIC values are shown in the table below.

The bacterial count of the test bacterial solution was $2.3 \times 10^7$ CFU/ml, and the number of bacteria added to the wells was $1.1 \times 10^5$ CFU/well.

TABLE 23

Results of growth test of test materials and MIC values

| Test material | Concentration of test material (µg/ml) | | | | | | | | | | MIC (µg/ml) |
|---|---|---|---|---|---|---|---|---|---|---|---|
| | 800 | 400 | 200 | 100 | 50 | 25 | 12.5 | 6.25 | 3.125 | 1.5625 | |
| NBP | − | − | − | − | − | + | + | + | + | + | 50 |
| NBP-A (100K) | − | − | − | − | − | − | − | + | + | + | 12.5 | n = 1
+: bacterial growth occurred
−: bacterial growth did not occur (6) Discussion The MIC value of NBP was 50 ng/ml and that of NBP-A (100K) was 12.5 µg/ml. Thus, a sample containing proanthocyanidin polymers with a higher degree of purification was found to have higher antibacterial activity against *Propionibacterium acnes*.

The *Propionibacterium acnes* JCM $6425^T$ bacteria used in the test are used for the evaluation of *Propionibacterium acnes* growth inhibitory components in Patent Documents 11 and 12. Patent Document 11 describes a method of inhibiting the growth of *Propionibacterium acnes* via the use of 100 µg/ml (0.01%) of isopropyl methylphenol in combination with 100 µg/ml (0.01%) of cis-6-hexadecenoic acid. Patent Document 12 describes a method of blocking the growth of *Propionibacterium acnes* via the use of 1,250 µg/ml of methyl parahydroxybenzoate in combination with 63 µg/ml of sodium dl-alpha-tocopheryl phosphate.

The MIC values of NBP and NBP-A (100K) for *Propionibacterium acnes* JCM $6425^T$ demonstrate that NBP and NBP-A (100K) have higher antibacterial activity than the components described in Patent Documents 11 and 12.

Formulation Example 1

Lotion

A lotion containing a 10K ultrafiltration concentrate derived from cashew apple of the present invention containing proanthocyanidin polymers (prepared in Example 9 (1)) can be prepared to have a composition as shown in Table 24 in a manner shown therein.

TABLE 24

| | Components | (%) |
|---|---|---|
| (1) | Dipotassium glycyrrhizinate | 0.20 |
| (2) | Citric acid | 0.10 |
| (3) | Sodium citrate | 0.30 |
| (4) | 10K ultrafiltration concentrate derived from cashew apple | 5.00 |
| (5) | 1,3-Butylene glycol | 5.00 |
| (6) | Aroma chemical | Adequate amount |
| (7) | Purified water | Balance |
| (8) | Tetraoleic acid-POE (60) sorbitol | 0.90 |
| (9) | Sorbitan monooleic acid | 0.10 |
| (10) | Preservative | Adequate amount |
| (11) | Ethanol | 10.00 |

(Preparation Method)

1) Components (1) to (5) are mixed, the percentage of a total of Components (1) to (5) is adjusted at 80% with the use of Component (7), and the components are dissolved while agitating the solution at 50° C.

2) Components (8) to (11) are mixed and dissolved while agitating the solution at 50° C.

3) Small amounts of Component (2) are gradually added to Component (1) and mixed with agitation at 50° C.

4) The mixture is homogeneously mixed, and the temperature is reduced from 50° C. to 30° C. with agitation.

5) Agitation is stopped when the temperature is reduced to 30° C., Components (6) is added, and Component (7) is added to adjust the total amount of the mixture.

6) The resultant is mixed and agitated again to obtain a homogeneously mixed lotion.

Formulation Example 2

Emulsion

An emulsion containing a 10K ultrafiltration concentrate derived from cashew apple of the present invention containing proanthocyanidin polymers (prepared in Example 9 (1)) can be prepared to have a composition as shown in Table 25 in a manner shown therein.

TABLE 25

| | Components | (%) |
|---|---|---|
| (1) | Squalene | 10.00 |
| (2) | Carboxyvinyl polymer | 0.10 |
| (3) | Xanthan gum | 0.20 |
| (4) | Triethanolamine | 0.10 |
| (5) | 1,3-Butylene glycol | 5.00 |
| (6) | Sodium hyaluronate | 2.00 |
| (7) | 10K ultrafiltration concentrate derived from cashew apple | 5.00 |
| (8) | Preservative | Adequate amount |
| (9) | Purified water | Balance |

(Preparation Method)

1) Components (1) and (8) are mixed, the percentage of a total of components (1) and (8) is adjusted at 70% with the use of Component (9), and the mixture is heated at 80° C.

2) Components (2) and (3) are mixed with Component (9), and these components are dissolved with agitation at room temperature.

3) Components (4) and (5) are mixed with Component (9), and these components are dissolved with agitation at room temperature.

4) Components (6) and (7) are mixed with Component (9), and these components are dissolved with agitation at room temperature.

5) Small amounts of the product of step 1) above are gradually added to Component (9) and mixed with agitation at 80° C.

6) With further agitation, the products of steps 2) and 3) are added in that order to the product of step 5).

7) After homogeneous mixing, the temperature is reduced to 50° C. with agitation.

8) The product of step 4) is added when the temperature is reduced to 50° C., and Component (9) is added to adjust the total amount of the mixture.

9) The temperature is reduced to 30° C. with further agitation.

10) Agitation is stopped when the temperature is reduced to 30° C. to obtain a homogeneously mixed lotion.

Formulation Example 3

Cream

A cream containing a 10K ultrafiltration concentrate derived from cashew apple of the present invention containing proanthocyanidin polymers (prepared in Example 9 (1)) can be prepared to have a composition as shown in Table 26 in a manner shown therein.

TABLE 26

| | Components | (%) |
|---|---|---|
| (1) | Polyoxyethylene (20) sorbitan monostearate | 2.00 |
| (2) | Polyoxyethylene sorbitan tetraoleate | 0.50 |
| (3) | Glyceryl monostearate | 0.50 |
| (4) | Stearic acid | 7.00 |
| (5) | Cetyl alcohol | 3.00 |
| (6) | Cetyl palmitate | 3.00 |
| (7) | Jojoba oil | 7.00 |
| (8) | Paraffin | 3.00 |
| (9) | Preservative | Adequate amount |
| (10) | 10K ultrafiltration concentrate derived from cashew apple | 5.00 |
| (11) | 1,3-Butylene glycol | 7.00 |
| (12) | Purified water | Balance |

(Preparation Method)

1) Components (1) to (9) are mixed and dissolved with agitation at 80° C.

2) Components (10) to (12) are mixed and dissolved with agitation at 80° C.

3) Small amounts of the product of step 1) are gradually added to the product of step 2) to emulsify the mixture.

4) The mixture is cooled to 40° C. with agitation.

5) Agitation is stopped when the temperature is reduced to 40° C. to obtain a homogeneously mixed cream.

All publications, patents, and patent applications cited herein are incorporated herein by reference in their entirety.

The invention claimed is:

1. A proanthocyanidin-containing extract purified from cashew apple, wherein the proanthocyanidins in said extract have an average degree of polymerization of at least 20.

2. The extract according to claim 1, wherein said extract is produced by a method comprising the step of concentrating or separating polyphenol from a cashew apple.

3. The extract according to claim 2, wherein said extract is produced by a method comprising the step of concentrating or separating proanthocyanidin from a cashew apple.

4. The extract according to claim 1, wherein the proanthocyanidin contains prodelphinidin.

5. A food, beverage, cosmetic, or pharmaceutical product, wherein said food, beverage, cosmetic, or pharmaceutical product is produced by adding the extract of claim 1 to a food, a beverage, a cosmetic composition, or a pharmaceutically acceptable carrier, respectively.

6. The extract of claim 1, wherein said proanthocyanidins comprise, as constitutional units, at least (epi)gallocatechin and (epi)gallocatechin gallate.

7. The extract of claim 1, wherein the average degree of polymerization is at least 25.

8. The extract of claim 1, wherein said proanthocyanidins comprise 50% to 80% by mole (epi)gallocatechin and 20% to 50% by mole (epi)gallocatechin gallate as constitutional units.

9. The extract of claim 1, wherein the proanthocyanidins further comprise epicatechin and epicatechin gallate as constitutional units.

10. The extract of claim 1, wherein at least one end of the polymer is epigallocatechin gallate.

* * * * *